US012004834B2

(12) United States Patent
Abbott et al.

(10) Patent No.: US 12,004,834 B2
(45) Date of Patent: Jun. 11, 2024

(54) MEDICAL TOOLS HAVING TENSION BANDS

(71) Applicant: Intuitive Surgical Operations, Inc., Sunnyvale, CA (US)

(72) Inventors: Ryan Abbott, San Jose, CA (US); Isabelle Heye, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 955 days.

(21) Appl. No.: 16/769,119

(22) PCT Filed: Dec. 10, 2018

(86) PCT No.: PCT/US2018/064725
§ 371 (c)(1),
(2) Date: Jun. 2, 2020

(87) PCT Pub. No.: WO2019/118336
PCT Pub. Date: Jun. 20, 2019

(65) Prior Publication Data
US 2020/0383738 A1 Dec. 10, 2020

Related U.S. Application Data

(60) Provisional application No. 62/598,620, filed on Dec. 14, 2017, provisional application No. 62/598,628, (Continued)

(51) Int. Cl.
*A61B 34/00* (2016.01)
*A61B 17/29* (2006.01)
(Continued)

(52) U.S. Cl.
CPC .......... *A61B 34/71* (2016.02); *A61B 17/2909* (2013.01); *A61B 17/320016* (2013.01);
(Continued)

(58) Field of Classification Search
CPC .............. A61B 34/30; A61B 2034/301; A61B 2034/305; A61B 2034/302; A61B 2034/303
See application file for complete search history.

(56) References Cited

U.S. PATENT DOCUMENTS 3,365,966 A * 1/1968 Heyer ...................... F16G 1/28
474/62
4,698,050 A   10/1987 Hattori et al.
(Continued)

FOREIGN PATENT DOCUMENTS

CA    2853431 A1    5/2013
CN    102458551 A   5/2012
(Continued)

OTHER PUBLICATIONS

Halverson P.A., "Multi-stable Compliant Rolling-contact Elements," Brigham Young University, May 3, 2007, 61 pages.
(Continued)

*Primary Examiner* — Tan-Uyen T Ho
*Assistant Examiner* — Osama Nemer

(57) ABSTRACT

A medical device includes a first link, a second link, and a band. A proximal end portion of the first link is coupled to a shaft. A proximal end portion of the second link is rotatably coupled to a distal end portion of first link about a first axis. The distal end portion of the second link includes a connector coupled to a tool member that is rotatable relative to the second link about a second axis that is non-parallel to the first axis. The first link defines a first guide channel and the second link defines a second guide channel. A distal end of the band is disposed within the first guide channel and the second guide channel, and is coupled to the tool member. The second link is rotatable relative to the first link about the first axis when the distal end of the band is moved.

20 Claims, 36 Drawing Sheets

Related U.S. Application Data filed on Dec. 14, 2017, provisional application No. 62/598,626, filed on Dec. 14, 2017.

(51) Int. Cl.
*A61B 17/32* (2006.01)
*A61B 34/30* (2016.01)
*A61B 34/35* (2016.01)
*F16H 7/02* (2006.01)

(52) U.S. Cl.
CPC ............ *A61B 34/30* (2016.02); *A61B 34/35* (2016.02); *F16H 7/02* (2013.01); *A61B 17/29* (2013.01); *A61B 2017/2911* (2013.01); *A61B 2017/2912* (2013.01); *A61B 2017/2916* (2013.01); *A61B 2017/2919* (2013.01); *A61B 2017/292* (2013.01); *A61B 2017/2923* (2013.01); *A61B 2017/2939* (2013.01); *A61B 2034/301* (2016.02); *A61B 2034/305* (2016.02); *A61B 2034/306* (2016.02); *A61B 2034/715* (2016.02)

(56) References Cited

U.S. PATENT DOCUMENTS

| | | |
|---|---|---|
| 5,325,845 A | 7/1994 | Adair |
| 5,487,377 A * | 1/1996 | Smith ................ A61B 17/4241 606/119 |
| 5,624,398 A | 4/1997 | Smith et al. |
| 5,784,542 A | 7/1998 | Ohm et al. |
| 5,792,135 A | 8/1998 | Madhani et al. |
| 5,807,377 A | 9/1998 | Madhani et al. |
| 5,855,583 A | 1/1999 | Wang et al. |
| 5,876,325 A | 3/1999 | Mizuno et al. |
| 5,899,914 A | 5/1999 | Zirps et al. |
| 5,916,146 A | 6/1999 | Allotta et al. |
| 6,007,550 A | 12/1999 | Wang et al. |
| 6,197,017 B1 | 3/2001 | Brock et al. |
| 6,206,903 B1 | 3/2001 | Ramans |
| 6,309,397 B1 | 10/2001 | Julian et al. |
| 6,331,181 B1 | 12/2001 | Tierney et al. |
| 6,371,952 B1 | 4/2002 | Madhani et al. |
| 6,394,998 B1 | 5/2002 | Wallace et al. |
| 6,491,626 B1 | 12/2002 | Stone et al. |
| 6,491,701 B2 | 12/2002 | Tierney et al. |
| 6,554,844 B2 | 4/2003 | Lee et al. |
| 6,676,684 B1 | 1/2004 | Morley et al. |
| 6,685,698 B2 | 2/2004 | Morley et al. |
| 6,767,349 B2 | 7/2004 | Ouchi |
| 6,817,974 B2 | 11/2004 | Cooper et al. |
| 6,840,938 B1 | 1/2005 | Morley et al. |
| 6,843,793 B2 | 1/2005 | Brock et al. |
| 6,949,106 B2 | 9/2005 | Brock et al. |
| 6,969,385 B2 | 11/2005 | Moreyra |
| 6,994,708 B2 | 2/2006 | Manzo |
| 7,083,571 B2 | 8/2006 | Wang et al. |
| 7,090,683 B2 | 8/2006 | Brock et al. |
| 7,125,403 B2 | 10/2006 | Julian et al. |
| 7,147,650 B2 | 12/2006 | Lee |
| 7,169,141 B2 | 1/2007 | Brock et al. |
| 7,214,230 B2 | 5/2007 | Brock et al. |
| 7,316,681 B2 | 1/2008 | Madhani et al. |
| 7,320,700 B2 | 1/2008 | Cooper et al. |
| 7,338,505 B2 | 3/2008 | Belson |
| 7,338,513 B2 | 3/2008 | Lee et al. |
| 7,371,210 B2 | 5/2008 | Brock et al. |
| 7,608,083 B2 | 10/2009 | Lee et al. |
| 7,682,307 B2 | 3/2010 | Danitz et al. |
| 7,699,835 B2 | 4/2010 | Lee et al. |
| 7,780,651 B2 | 8/2010 | Madhani et al. |
| 7,785,252 B2 | 8/2010 | Danitz et al. |
| 7,824,401 B2 | 11/2010 | Manzo et al. |
| 7,935,130 B2 | 5/2011 | Williams |
| 7,963,913 B2 | 6/2011 | Devengenzo et al. |
| 8,075,476 B2 | 12/2011 | Vargas |
| 8,142,421 B2 | 3/2012 | Cooper et al. |
| 8,245,595 B2 | 8/2012 | Milenkovic |
| 8,347,757 B2 | 1/2013 | Duval |
| 8,479,969 B2 | 7/2013 | Shelton, IV |
| 8,540,748 B2 | 9/2013 | Murphy et al. |
| 8,551,115 B2 | 10/2013 | Steger et al. |
| 8,602,288 B2 | 12/2013 | Shelton, IV et al. |
| 8,771,270 B2 | 7/2014 | Burbank |
| 8,800,838 B2 | 8/2014 | Shelton, IV |
| 8,821,480 B2 * | 9/2014 | Burbank ................ A61B 34/30 606/1 |
| 8,939,963 B2 | 1/2015 | Rogers et al. |
| 9,028,494 B2 | 5/2015 | Shelton, IV et al. |
| 9,055,961 B2 | 6/2015 | Manzo et al. |
| 9,078,684 B2 | 7/2015 | Williams |
| 9,198,729 B2 | 12/2015 | Rogers |
| 9,204,923 B2 | 12/2015 | Manzo et al. |
| 9,211,134 B2 * | 12/2015 | Stroup ................ A61B 17/29 |
| 9,232,979 B2 | 1/2016 | Parihar et al. |
| 9,259,275 B2 | 2/2016 | Burbank |
| 9,533,122 B2 | 1/2017 | Weitzner et al. |
| 9,803,727 B2 | 10/2017 | Solomon et al. |
| 10,130,366 B2 | 11/2018 | Shelton, IV et al. |
| 10,285,763 B2 | 5/2019 | Vale et al. |
| 10,299,873 B2 | 5/2019 | Hares et al. |
| 10,335,177 B2 | 7/2019 | Steger |
| 10,524,870 B2 | 1/2020 | Saraliev et al. |
| 10,595,836 B2 | 3/2020 | Smaby et al. |
| 10,595,948 B2 | 3/2020 | Solomon et al. |
| 10,682,141 B2 | 6/2020 | Moore et al. |
| 10,758,298 B2 | 9/2020 | Felder et al. |
| 10,786,320 B2 | 9/2020 | Adams et al. |
| 10,792,116 B2 | 10/2020 | Haraguchi et al. |
| 10,813,706 B2 | 10/2020 | Chaplin et al. |
| 11,020,112 B2 | 6/2021 | Shelton, IV et al. |
| 11,045,270 B2 | 6/2021 | Shelton, IV et al. |
| 11,109,928 B2 | 9/2021 | Schuh |
| 11,129,686 B2 | 9/2021 | Chaplin et al. |
| 2001/0025134 A1 | 9/2001 | Bon et al. |
| 2002/0111621 A1 | 8/2002 | Wallace et al. |
| 2004/0260198 A1 | 12/2004 | Rothberg et al. |
| 2004/0266574 A1 | 12/2004 | Jinno et al. |
| 2006/0074415 A1 | 4/2006 | Scott et al. |
| 2006/0131908 A1 | 6/2006 | Tadano |
| 2006/0190034 A1 | 8/2006 | Nishizawa et al. |
| 2007/0123855 A1 * | 5/2007 | Morley ................ A61B 34/71 606/50 |
| 2007/0158385 A1 | 7/2007 | Hueil et al. |
| 2007/0208375 A1 | 9/2007 | Nishizawa et al. |
| 2007/0246508 A1 | 10/2007 | Green |
| 2008/0046122 A1 | 2/2008 | Manzo et al. |
| 2008/0065102 A1 | 3/2008 | Cooper |
| 2008/0125794 A1 | 5/2008 | Brock et al. |
| 2008/0196533 A1 | 8/2008 | Bergamasco et al. |
| 2008/0255421 A1 | 10/2008 | Hegeman et al. |
| 2009/0088774 A1 | 4/2009 | Swarup et al. |
| 2009/0163929 A1 | 6/2009 | Yeung et al. |
| 2009/0171348 A1 | 7/2009 | Guo et al. |
| 2009/0198272 A1 | 8/2009 | Kerver et al. |
| 2009/0216248 A1 | 8/2009 | Uenohara et al. |
| 2009/0326530 A1 | 12/2009 | Orban, III et al. |
| 2010/0011901 A1 | 1/2010 | Burbank |
| 2010/0030238 A1 | 2/2010 | Viola et al. |
| 2010/0198218 A1 | 8/2010 | Manzo |
| 2010/0198253 A1 | 8/2010 | Jinno et al. |
| 2011/0295269 A1 | 12/2011 | Swensgard et al. |
| 2011/0295270 A1 | 12/2011 | Giordano et al. |
| 2012/0330287 A1 | 12/2012 | Yim |
| 2013/0123783 A1 | 5/2013 | Marczyk et al. |
| 2013/0144395 A1 | 6/2013 | Stefanchik et al. |
| 2013/0239735 A1 | 9/2013 | Solomon et al. |
| 2013/0304084 A1 | 11/2013 | Beira et al. |
| 2013/0345718 A1 | 12/2013 | Crawford et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0073856 A1 | 3/2014 | Stein et al. |
| 2014/0114327 A1 | 4/2014 | Boudreaux et al. |

(56) References Cited

U.S. PATENT DOCUMENTS

| | | |
|---|---|---|
| 2014/0276950 A1 | 9/2014 | Smaby et al. |
| 2014/0276956 A1 | 9/2014 | Crainich et al. |
| 2015/0005786 A1 | 1/2015 | Burbank |
| 2015/0150635 A1 | 6/2015 | Kilroy et al. |
| 2015/0157355 A1 | 6/2015 | Price et al. |
| 2015/0313676 A1 | 11/2015 | Deodhar |
| 2016/0051274 A1 | 2/2016 | Howell et al. |
| 2016/0166342 A1 | 6/2016 | Prisco et al. |
| 2016/0287279 A1 | 10/2016 | Bovay et al. |
| 2016/0287346 A1 | 10/2016 | Hyodo et al. |
| 2016/0296219 A1 | 10/2016 | Srivastava et al. |
| 2016/0302819 A1 | 10/2016 | Stulen et al. |
| 2016/0361123 A1 | 12/2016 | Hares et al. |
| 2017/0007242 A1 | 1/2017 | Shelton, IV et al. |
| 2017/0007345 A1 | 1/2017 | Smith et al. |
| 2017/0095922 A1 | 4/2017 | Licht et al. |
| 2017/0120457 A1 | 5/2017 | Saraliev et al. |
| 2017/0165017 A1 | 6/2017 | Chaplin et al. |
| 2017/0234411 A1 | 8/2017 | Dewaele et al. |
| 2017/0252096 A1 | 9/2017 | Felder et al. |
| 2017/0265954 A1 | 9/2017 | Burbank et al. |
| 2018/0080533 A1 | 3/2018 | Awtar |
| 2018/0206904 A1 | 7/2018 | Felder et al. |
| 2018/0333164 A1 | 11/2018 | Arata et al. |
| 2019/0090940 A1 | 3/2019 | Manzo et al. |
| 2019/0094084 A1 | 3/2019 | Swinehart et al. |
| 2019/0099227 A1 | 4/2019 | Rockrohr |
| 2019/0099231 A1 | 4/2019 | Bruehwiler et al. |
| 2019/0223960 A1 | 7/2019 | Chaplin et al. |
| 2019/0239877 A1 | 8/2019 | Ragosta et al. |
| 2019/0239967 A1 | 8/2019 | Ragosta et al. |
| 2019/0328467 A1 | 10/2019 | Waterbury et al. |
| 2019/0336228 A1 | 11/2019 | Blumenkranz et al. |
| 2019/0380800 A1 | 12/2019 | Jogasaki et al. |
| 2020/0015807 A1* | 1/2020 | Limon ............... A61B 17/062 |
| 2020/0022765 A1 | 1/2020 | Limon et al. |
| 2020/0054405 A1 | 2/2020 | Schuh et al. |
| 2020/0054408 A1 | 2/2020 | Schuh et al. |
| 2020/0093554 A1 | 3/2020 | Schuh et al. |
| 2020/0138531 A1 | 5/2020 | Chaplin |
| 2020/0170734 A1 | 6/2020 | Saraliev et al. |
| 2020/0197112 A1 | 6/2020 | Chin et al. |
| 2020/0352660 A1 | 11/2020 | Prisco |
| 2020/0383739 A1 | 12/2020 | Abbott et al. |
| 2021/0022819 A1 | 1/2021 | Duque et al. |
| 2021/0169597 A1 | 6/2021 | Abbott et al. |
| 2021/0244427 A1 | 8/2021 | Lee et al. |
| 2022/0354474 A1 | 11/2022 | Ratia et al. |

FOREIGN PATENT DOCUMENTS

| | | |
|---|---|---|
| CN | 102488554 A | 6/2012 |
| CN | 104116547 A | 10/2014 |
| CN | 106714721 A | 5/2017 |
| CN | 113262051 A | 8/2021 |
| EP | 1847289 A2 | 10/2007 |
| EP | 2338434 A2 | 6/2011 |
| EP | 2362285 A2 | 8/2011 |
| EP | 2415418 A1 | 2/2012 |
| EP | 2548529 A1 | 1/2013 |
| EP | 2783643 A1 | 10/2014 |
| EP | 3100666 A1 | 12/2016 |
| EP | 3103374 A1 | 12/2016 |
| FR | 3016543 A1 | 7/2015 |
| GB | 191012759 A | 3/1911 |
| GB | 2590881 A | 7/2021 |
| JP | H09164225 A | 6/1997 |
| JP | 2002503131 A | 1/2002 |
| JP | 2004301275 A | 10/2004 |
| JP | 2006061364 A | 3/2006 |
| JP | 2009226194 A | 10/2009 |
| JP | 2014159071 A | 9/2014 |
| JP | 2014534080 A | 12/2014 |
| JP | 2018029468 A | 2/2018 |
| JP | 2018511430 A | 4/2018 |
| KR | 100778387 B1 | 11/2007 |
| WO | WO-2006039092 A2 | 4/2006 |
| WO | WO-2010081050 A1 | 7/2010 |
| WO | WO-2011060315 A2 | 5/2011 |
| WO | WO-2011097095 A1 | 8/2011 |
| WO | WO-2012006306 A2 | 1/2012 |
| WO | WO-2012049623 A1 | 4/2012 |
| WO | WO-2013181522 A1 | 12/2013 |
| WO | WO-2014025204 A1 | 2/2014 |
| WO | WO-2014151952 A1 | 9/2014 |
| WO | WO-2015127231 A1 | 8/2015 |
| WO | WO-2015153111 A1 | 10/2015 |
| WO | WO-2016025132 A1 | 2/2016 |
| WO | WO-2016123139 A2 | 8/2016 |
| WO | WO-2016161449 A1 | 10/2016 |
| WO | WO-2016189284 A1 | 12/2016 |
| WO | WO-2017064301 A1 | 4/2017 |
| WO | WO-2017064303 A1 | 4/2017 |
| WO | WO-2017064306 A1 | 4/2017 |
| WO | WO-2017098273 A1 | 6/2017 |
| WO | WO-2017136710 A2 | 8/2017 |
| WO | WO-2018049211 A1 | 3/2018 |
| WO | WO-2018069679 A1 | 4/2018 |
| WO | WO-2018094191 A1 | 5/2018 |
| WO | WO-2018123024 A1 | 7/2018 |
| WO | WO-2018179140 A1 | 10/2018 |
| WO | WO-2019118334 A1 | 6/2019 |
| WO | WO-2019118336 A1 | 6/2019 |
| WO | WO-2019118337 A1 | 6/2019 |
| WO | WO-2023177565 A1 | 9/2023 |

OTHER PUBLICATIONS

International Search Report and Written Opinion for Application No. PCT/US2018/064721, dated May 22, 2019, 30 pages.
International Search Report and Written Opinion for Application No. PCT/US2018/064725, dated Mar. 28, 2019, 9 pages.
International Search Report and Written Opinion for Application No. PCT/US2018/064728, dated May 14, 2019, 19 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP18887892.0 dated Jul. 20, 2021, 7 pages.
Extended European Search Report for Application No. EP18889541.1 dated Sep. 14, 2021, 7 pages.
Extended European Search Report for Application No. EP20180889370.5 dated Aug. 24, 2021, 7 pages.
Office Action for JP Application No. 2020-532549, dated Jul. 13, 2021.
Office Action for JP Application No. 2020-532725, dated Jul. 13, 2021.
Office Action for JP Application No. 2020-532669, dated Jul. 20, 2021.
Office Action for CN Application No. 201880073669X, dated Sep. 27, 2022, 23 pages.
Office Action for CN Application No. 2018800736810, dated Oct. 10, 2022, 13 pages.
Office Action for CN Application No. 2018800736539, dated Nov. 16, 2022, 39 pages.
Notice of Allowance for KR Application No. 10-2020-7016623, dated Oct. 20, 2021, 4 pages.
Notice of Allowance for KR Application No. 10-2020-7016635, dated Oct. 20, 2021, 4 pages.
Office Action for KR Application No. 10-2020-7016660, dated Oct. 22, 2021, 10 pages.
Office Action for JP Application No. 2020-532725, dated Dec. 14, 2021, 9 pages.
Office Action for U.S. Appl. No. 16/769,116, dated Oct. 5, 2021.
Final Office Action for U.S. Appl. No. 16/769,116, dated Mar. 18, 2022.
International Search Report and Written Opinion for Application No. PCT/US2020/037265, dated Sep. 4, 2020, 12 pages.

(56) References Cited

OTHER PUBLICATIONS

Office Action for CN Application No. 2018800736539, dated Sep. 23, 2023, 40 pages.
Office Action for CN Application No. 201880073669X, dated Mar. 3, 2023, 21 pages.
Office Action for U.S. Appl. No. 16/769,121, mailed Mar. 1, 2024, 07 pages.

* cited by examiner

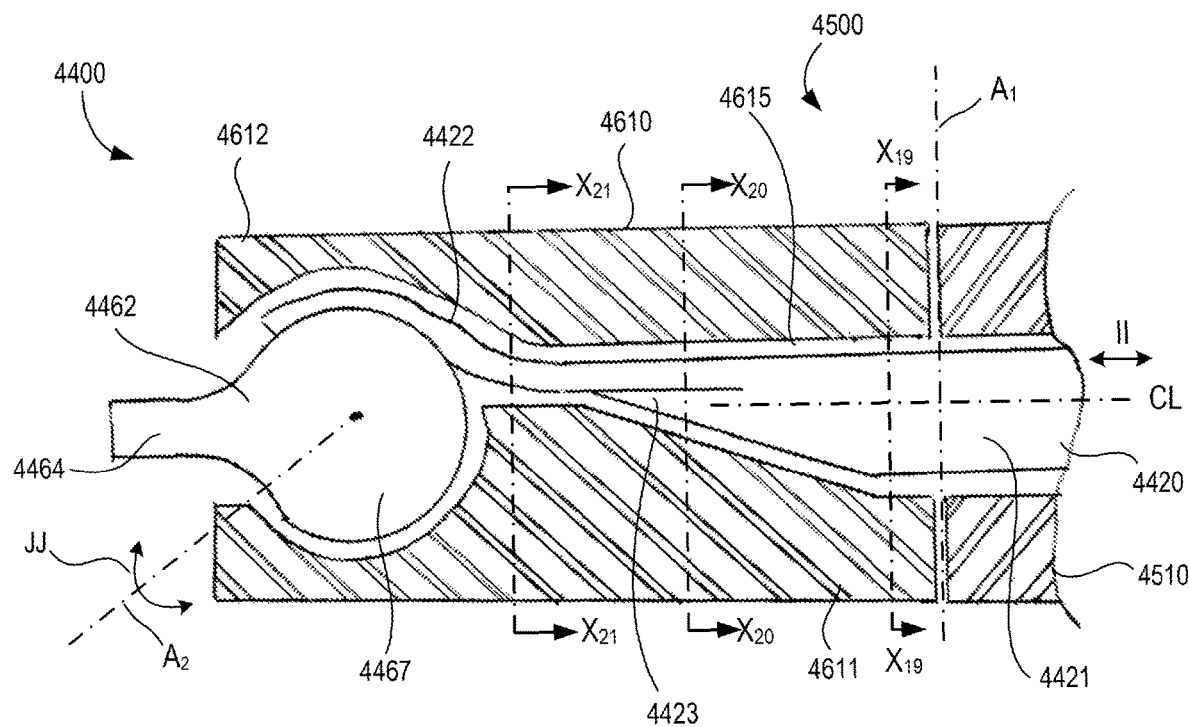
FIG. 18
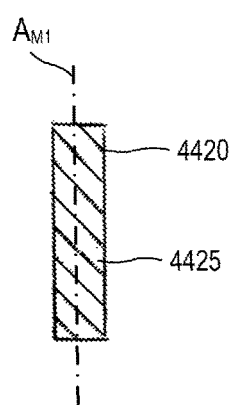
FIG. 19
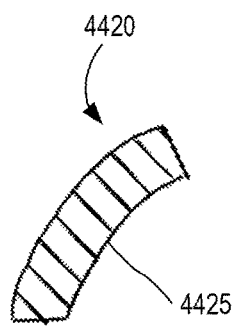
FIG. 20
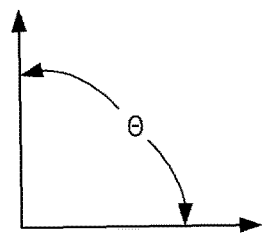
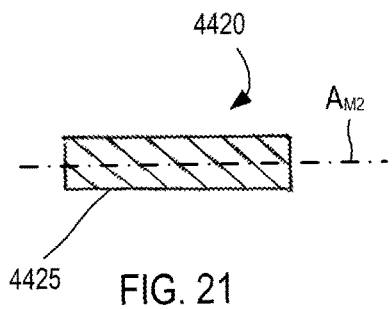
FIG. 21

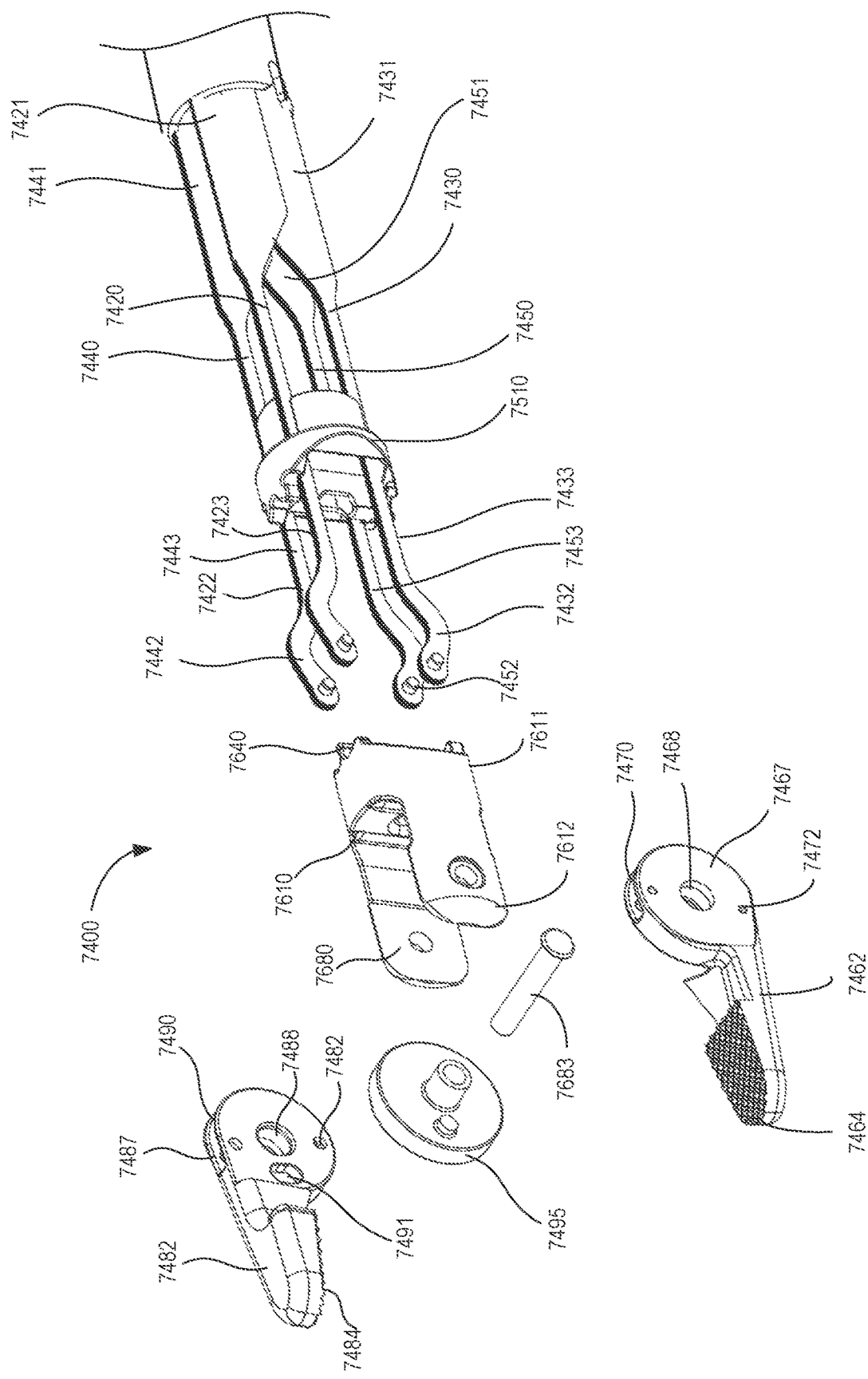

MEDICAL TOOLS HAVING TENSION BANDS

CROSS-REFERENCE TO RELATED APPLICATIONS

This application is a U.S. national stage filing under 35 U.S.C. § 371 of International Application No. PCT/US2018/064725 (filed Dec. 10, 2018)(entitled "MEDICAL TOOLS HAVING TENSIONS BANDS"), which claims benefit of priority to U.S. Provisional Application Ser. No. 62/598,620 (filed on Dec. 14, 2017), entitled "Medical Tools Having Tension Bands," U.S. Provisional Application Ser. No. 62/598,626 (filed on Dec. 14, 2017), entitled "Medical Tools Having Tension Bands," and U.S. Provisional Application Ser. No. 62/598,628 (filed on Dec. 14, 2017), entitled "Medical Tools Having Tension Bands," which are all incorporated herein by reference in their entirety.

BACKGROUND

The embodiments described herein relate to grasping tools, more specifically to medical devices, and still more specifically to endoscopic tools. More particularly, the embodiments described herein relate to devices that include tension bands that can be used, for example, in surgical applications.

Known techniques for Minimally Invasive Surgery (MIS) employ instruments to manipulate tissue that can be either manually controlled or controlled via computer-assisted teleoperation. Many known MIS instruments include a therapeutic or diagnostic end effector (e.g., forceps, a cutting tool, or a cauterizing tool) mounted on a wrist mechanism at the distal end of a shaft. During an MIS procedure, the end effector, wrist mechanism, and the distal end of the shaft can be inserted into a small incision or a natural orifice of a patient to position the end effector at a work site within the patient's body. The optional wrist mechanism can be used to change the end effector's orientation with respect to the shaft to perform the desired procedure at the work site. Known wrist mechanisms generally provide the desired degrees of freedom (DOFs) for movement of the end effector. For example, for forceps or other grasping tools, known wrist mechanisms are often able to change the pitch and yaw of the end effector with reference to the shaft. A wrist may optionally provide a roll DOF for the end effector, or the roll DOF may be implemented by rolling the shaft. An end effector may optionally have additional mechanical DOFs, such as grip or knife blade motion. In some instances, wrist and end effector mechanical DOFs may be combined. For example, U.S. Pat. No. 5,792,135 (filed May 16, 1997) discloses a mechanism in which wrist and end effector grip DOFs are combined.

To enable the desired movement of the wrist mechanism and end effector, known instruments include tension elements (e.g., cables) that extend through the shaft of the instrument and that connect the wrist mechanism to an actuator (also referred to herein as a backend mechanism). The actuator moves the cables to operate the wrist mechanism. For robotic or teleoperated systems, the backend mechanism is motor driven and can be operably coupled to a processing system to provide a user interface for a user to control the instrument.

Patients benefit from continual efforts to improve the effectiveness of MIS methods and tools. For example, reducing the size and/or the operating footprint of the shaft and wrist mechanism can allow for smaller entry incisions, thereby reducing the negative effects of surgery, such as pain, scarring, and undesirable healing time. But, producing small diameter medical instruments that implement the clinically desired functions for minimally invasive procedures can be challenging. Specifically, simply reducing the size of known wrist mechanisms by "scaling down" the components will not result in an effective solution because required component and material properties do not scale. For example, efficient implementation of a wrist mechanism can be complicated because the cables must be carefully routed through the wrist mechanism to maintain cable tension throughout the range of motion of the wrist mechanism and to minimize the interactions (or coupling effects) of one rotation axis upon another. Further, pulleys and/or contoured surfaces are generally needed to reduce cable friction, which extends instrument life and permits operation without excessive forces being applied to the cables or other structures in the wrist mechanism. Increased localized forces that may result from smaller structures (including the cables and other components of the wrist mechanism) can result in undesirable lengthening (e.g., "stretch" or "creep") of the cables during storage and use, reduced cable life, and the like.

Further, some medical instruments have end effectors that require electrical energy for clinical functions such as desiccation, hemostasis, cutting, dissection, fulguration, incisions, tissue destruction, cauterizing, and vessel sealing. Accordingly, known instruments include one more conductors routed through the wrist mechanism to the portion of an end effector to be energized. Fitting all the components of the wrist mechanism, drive cables, and conductive wires into a small diameter, for example, less than about 10 mm, while preserving the necessary strength and function of these components can be difficult.

In addition to reducing the size of instrument, it is also desirable to develop low-cost instruments that are effectively disposable (i.e., that are intended for a single use only at an economic cost). With such instruments, each MIS procedure can be performed with a new, sterilized instrument, which eliminates cumbersome and expensive instrument reuse sterilization procedures. Many current instrument designs are expensive to produce, however, and so for economy these instruments undergo sterile reprocessing for use during multiple surgical procedures. In part the cost of these instruments may be due to multiple-strand tungsten cables and hypotube portions to withstand the operating loads.

Thus, a need exists for improved endoscopic tools, including improved wrist mechanisms having reduced size, reduced part count, lower cost of materials, and including tension members having increased strength.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter. In some embodiments, a medical device includes a first link, a second link, and a band. The first link and the second link each have a proximal end portion and a distal end portion. The proximal end portion of the first link is coupled to a shaft. The proximal end portion of the second link is rotatably coupled to the distal end portion of first link. The second link is rotatable relative to the first link about a first axis. The distal end portion of the second link includes a connector coupled to a tool member that is rotatable relative to the second link about a second axis. The second axis is non-parallel to the first axis. A first guide channel is defined within the first link, and a second guide channel is defined within the second link. A distal end portion of the band is disposed within the first guide channel and the second guide channel, and is coupled to the tool member. The second link is rotatable relative to the first link about the first axis when the distal end portion of the band is moved.

In some embodiments, a medical device includes a first link, a second link, a tool member, and a band. The first link is coupled to a shaft. A proximal end portion of the second link is coupled to the first link such that the second link is rotatable relative to the first link about a first axis. A guide channel is defined with the second link. The tool member has a contact portion and a pulley portion. The contact portion is configured to contact a target tissue. The pulley portion is rotatably coupled to a distal end portion of the second link such that the tool member is rotatable relative to the second link about a second axis. The second axis is non-parallel to the first axis. The band has a first band portion and a second band portion. The first band portion is disposed within the guide channel, and the second band portion is coupled to the tool member. The band is twisted along a longitudinal center line of the band between the first band portion and the second band portion. The tool member is rotatable relative to the second link about the second axis when the band is moved.

BRIEF DESCRIPTION OF THE DRAWINGS

FIG. 18 is a diagrammatic front cross-sectional view of a portion of an instrument of a surgery system, according to an embodiment.

FIGS. 19-21 are diagrammatic side cross-sectional views of a band included within the instrument shown in FIG. 18, taken along the lines $X_{19}$-$X_{19}$ (FIG. 19), $X_{20}$-$X_{20}$ (FIG. 20), and $X_{21}$-$X_{21}$ (FIG. 21).

FIG. 29 is an exploded perspective view of the distal end portion of the instrument shown in FIG. 27.

DETAILED DESCRIPTION

Figure 1:
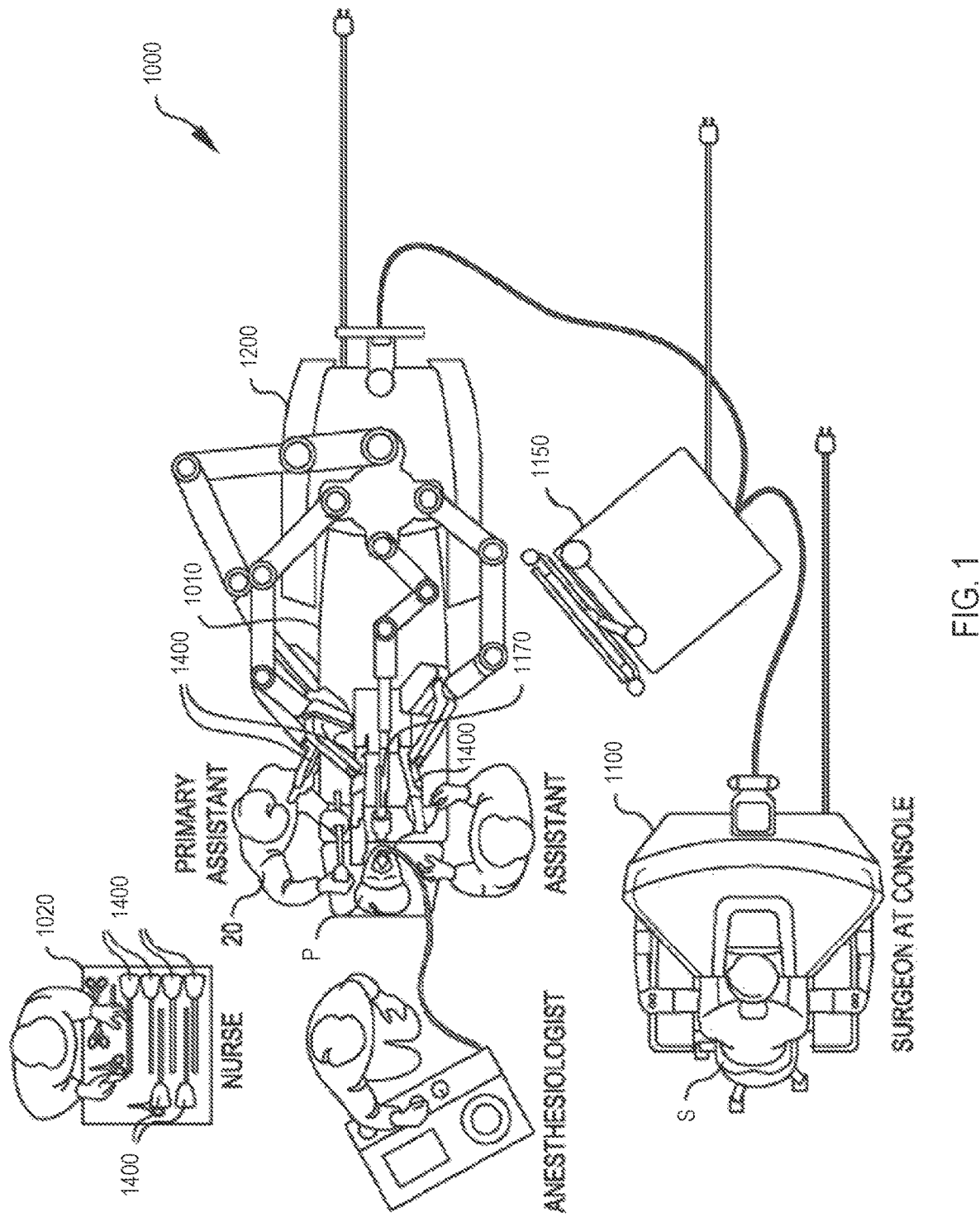
FIG. 1 is a plan view of a teleoperated medical system according to an embodiment, being used to perform a medical procedure such as surgery.

The embodiments described herein can advantageously be used in a wide variety of grasping, cutting, and manipulating operations associated with surgery. In particular, the instruments described herein can be low-cost, disposable instruments that facilitate being used for only one procedure. As described herein, the instruments include one or more bands that can be moved to actuate the end effector with multiple degrees of freedom. Moreover, the bands can include regions having a larger cross-sectional area to promote increased strength, or can be twisted to allow efficient routing within a miniaturized wrist assembly.

In some embodiments, a medical device includes a first link, a second link, and a band. The first link and the second link each have a proximal end portion and a distal end portion. The proximal end portion of the first link is coupled to a shaft. The proximal end portion of the second link is rotatably coupled to the distal end portion of first link. The second link is rotatable relative to the first link about a first axis. The distal end portion of the second link includes a connector coupled to a tool member that is rotatable relative to the second link about a second axis. The second axis is non-parallel to the first axis. A first guide channel is defined within the first link, and a second guide channel is defined within the second link. A distal end portion of the band is disposed within the first guide channel and the second guide channel, and is coupled to the tool member. The second link is rotatable relative to the first link about the first axis when the distal end portion of the band is moved.

In some embodiments, a medical device includes a first link, a second link, and a band. The first link and the second link each have a proximal end portion and a distal end portion. The proximal end portion of the first link is coupled to a shaft. The proximal end portion of the second link is rotatably coupled to the distal end portion of first link. The second link is rotatable relative to the first link about a first axis. The distal end portion of the second link includes a connector coupled to a tool member that is rotatable relative to the second link about a second axis. The second axis is non-parallel to the first axis. A first guide channel is defined within the first link, and a second guide channel is defined within the second link. A distal end portion of the band is disposed within the first guide channel and the second guide channel. The distal end portion of the band is coupled to the tool member. The tool member rotatable relative to the second link about the second axis when the distal end portion of the band is moved.

In some embodiments, a medical device includes a first link, a second link, and a band. The first link and the second link each have a proximal end portion and a distal end portion. The proximal end portion of the first link is coupled to a shaft. The first link includes an inner guide surface and an outer guide surface that collectively define a first guide channel. A portion of the inner guide surface taken within a cross-sectional plane normal to a longitudinal center line of the first guide channel is linear, and a portion of the outer guide surface taken within the cross-sectional plane is linear. The proximal end portion of the second link is rotatably coupled to the distal end portion of first link. The second link is rotatable relative to the first link about a first axis. The distal end portion of the second link includes a connector coupled to a tool member that is rotatable relative to the second link about a second axis. The second axis is non-parallel to the first axis. A distal end portion of the band is disposed within the first guide channel. The distal end portion of the band is coupled to the tool member. The tool member rotatable relative to the second link about the second axis when the distal end portion of the band is moved. An inner contact surface of the band contacts the inner guide surface of the first link when the second link rotates relative to the first link about the first axis in a first direction. An outer contact surface of the band contacts the outer guide surface of the first link when the second link rotates relative to the first link about the first axis in a second direction.

In some embodiments, a medical device includes a joint assembly, a tool member, and a band. The joint assembly has a proximal end portion and a distal end portion. The proximal end portion of the joint assembly is coupled to a shaft. The tool member has a contact portion and a coupling portion. The contact portion is configured to contact a target tissue, and the coupling portion is rotatably coupled to a distal end portion of the joint assembly. The band has a first band portion and a second band portion. The first band portion is within the shaft, and has a first cross-sectional area in a first plane normal to a longitudinal center line of the band. The second band portion is coupled to the tool member, and has a second cross-sectional area in a second plane normal to the longitudinal center line of the band. The second cross-sectional area is different than the first cross-sectional area. The tool member is rotatable relative to the joint assembly about a rotation axis when the band is moved along its longitudinal center line.

In some embodiments, a medical device includes a first link, a second link, a tool member, and a band. The first link is coupled to a shaft. A proximal end portion of the second link is coupled to the first link such that the second link is rotatable relative to the first link about a first axis. The tool member has a contact portion and a pulley portion. The contact portion is configured to contact a target tissue, and the pulley portion is rotatably coupled to the distal end portion of the second link. The band has a first band portion, a second band portion, and a third band portion. The second band portion is between the first band portion and the third band portion. The first band portion and the third band portion are each within the shaft. The first band portion has a first cross-sectional area in a first plane normal to a longitudinal center line of the band. The second band portion is at least partially wrapped about the pulley portion. The second band portion has a second cross-sectional area in a second plane normal to the longitudinal center line of the band. The second cross-sectional area is different than the first cross-sectional area. The tool member is rotatable relative to the second link about a rotation axis when the band is moved along its longitudinal center line.

In some embodiments, a medical device includes a joint assembly, a tool member, and a band. The joint assembly has a proximal end portion and a distal end portion. The proximal end portion of the joint assembly is coupled to a shaft. The joint assembly includes a guide surface. The tool member has a contact portion and a pulley portion. The contact portion is configured to contact a target tissue. The band has a first band portion, a second band portion, and a third band portion. The second band portion is between the first band portion and the third band portion. The first band portion is within the shaft, and has a first cross-sectional area in a first plane normal to a longitudinal center line of the band. The second band portion is coupled to the pulley portion such that the tool member is rotatable relative to the joint assembly about a rotation axis when the second band portion is moved. The second band portion has a second cross-sectional area in a second plane normal to the longitudinal center line of the band. The third band portion transitions from the first cross-sectional area to the second cross-sectional area.

In some embodiments, a medical device includes a first link, a second link, a tool member, and a band. The first link is coupled to a shaft. A proximal end portion of the second link is coupled to the first link such that the second link is rotatable relative to the first link about a first axis. The second link defines a guide channel. The tool member has a contact portion and a pulley portion. The contact portion is configured to contact a target tissue, and the pulley portion is rotatably coupled to a distal end portion of the second link such that the tool member is rotatable relative to the second link about a second axis. The second axis is non-parallel to the first axis. The band has a first band portion and a second band portion. The first band portion is disposed within the guide channel. The second band portion is coupled to the tool member. The band is twisted along a longitudinal center line of the band between the first band portion and the second band portion. The tool member is rotatable relative to the second link about the second axis when the band is moved.

In some embodiments, a medical device includes a first link, a second link, a tool member, and a band. The first link is coupled to a shaft. A proximal end portion of the second link is coupled to the first link such that the second link is rotatable relative to the first link about a first axis. The second link defines a first guide channel and a second guide channel. The tool member has a contact portion and a pulley portion. The contact portion is configured to contact a target tissue, and the pulley portion is rotatably coupled to a distal end portion of the second link such that the tool member is rotatable relative to the second link about a second axis. The second axis is non-parallel to the first axis. The band has a first band portion, a second band portion, and a third band portion. The second band portion is between the first band portion and the third band portion. The first band portion is disposed within the first guide channel, the third band portion is disposed within the second guide channel. The second band portion is at least partially wrapped about the pulley portion. The band is twisted along a longitudinal center line of the band between the first band portion and the second band portion. The tool member is rotatable relative to the second link about the second axis when the band is moved along its longitudinal center line.

In some embodiments, a medical device includes a first link, a second link, a tool member, and a band. The first link is coupled to a shaft. A proximal end portion of the second link is coupled to the first link such that the second link is rotatable relative to the first link about a first axis. The second link includes a guide surface. The tool member has a contact portion and a pulley portion. The contact portion is configured to contact a target tissue, and the pulley portion is rotatably coupled to a distal end portion of the second link such that the tool member is rotatable relative to the second link about a second axis. The second axis is non-parallel to the first axis. The band has a contact surface. A first portion of the contact surface is in sliding contact with the guide surface at a first band location along a longitudinal center line of the band. A second portion of the contact surface is coupled to the pulley portion at a second band location along the longitudinal center line of the band. The first portion of the contact surface is nonparallel to the second portion of the contact surface. The tool member is rotatable relative to the second link about the second axis when the band is moved along its longitudinal center line.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g., a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein.

A flexible part may have infinite degrees of freedom (DOF's). Flexibility is an extensive property of the object being described, and thus is dependent upon the material from which the object is formed as well as certain physical characteristics of the object (e.g., cross-sectional shape, length, boundary conditions, etc.). For example, the flexibility of an object can be increased or decreased by selectively including in the object a material having a desired modulus of elasticity, flexural modulus and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the flexibility of the object can be decreased, for example, by introducing into the object and/or constructing the object of a material having a relatively high modulus of elasticity. Examples of such parts include closed, bendable tubes (made from, e.g., NITINOL®, polymer, soft rubber, and the like), helical coil springs, etc. that can be bent into various simple or compound curves, often without significant cross-sectional deformation.

Other flexible parts may approximate such an infinite-DOF part by using a series of closely spaced components that are similar to a serial arrangement of short, connected links as snake-like "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOFs of relative movement between the links. A short, flexible part may serve as, and be modeled as, a single mechanical constraint (a joint) that provides one or more DOF's between two links in a kinematic chain, even though the flexible part itself may be a kinematic chain made of several coupled links having multiple DOFs, or an infinite-DOF link.

As used in this specification, the word "distal" refers to direction towards a work site, and the word "proximal" refers to a direction away from the work site. Thus, for example, the end of a tool that is closest to the target tissue would be the distal end of the tool, while the end opposite the distal end (i.e., the end manipulated by the user or an actuator) would be the proximal end of the tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a da Vinci® Surgical System, commercialized by Intuitive Surgical, Inc. of Sunnyvale, California. Examples of such surgical systems are the da Vinci Xi® Surgical System (Model IS4000) and the da Vinci Si® Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations.

Implementations on da Vinci® Surgical Systems (e.g., the Model IS4000, the Model IS3000, the Model IS2000, the Model IS1200) are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

FIG. 1 is a plan view illustration of a computer-assisted teleoperation system. Shown is a medical device, which is a Minimally Invasive Robotic Surgical (MIRS) system 1000 (also referred to herein as a minimally invasive teleoperated surgery system), used for performing a minimally invasive diagnostic or surgical procedure on a Patient P who is lying down on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot), and an optional auxiliary unit 1150. The manipulator unit 1200 can manipulate at least one removably coupled tool assembly 1400 (also referred to herein as a "tool") through a minimally invasive incision in the body or natural orifice of the patient P while the surgeon S views the surgical site and controls movement of the tool 1400 through the user control unit 1100. An image of the surgical site is obtained by an endoscope 1170, such as a stereoscopic endoscope, which can be manipulated by the manipulator unit 1200 to orient the endoscope 1170. The auxiliary unit 1150 can be used to process the images of the surgical site for subsequent display to the Surgeon S through the control unit 1100. The number of tools 1400 used at one time will generally depend on the diagnostic or surgical procedure and the space constraints within the operating room, among other factors. If it is necessary to change one or more of the instruments 1400 being used during a procedure, an assistant removes the tool 1400 from the manipulator unit 1200 and replaces it with another tool 1400 from a tray 1020 in the operating room. Although shown as being used with the instruments 1400, any of the instruments described herein can be used with the MIRS 1000.

Figure 2:
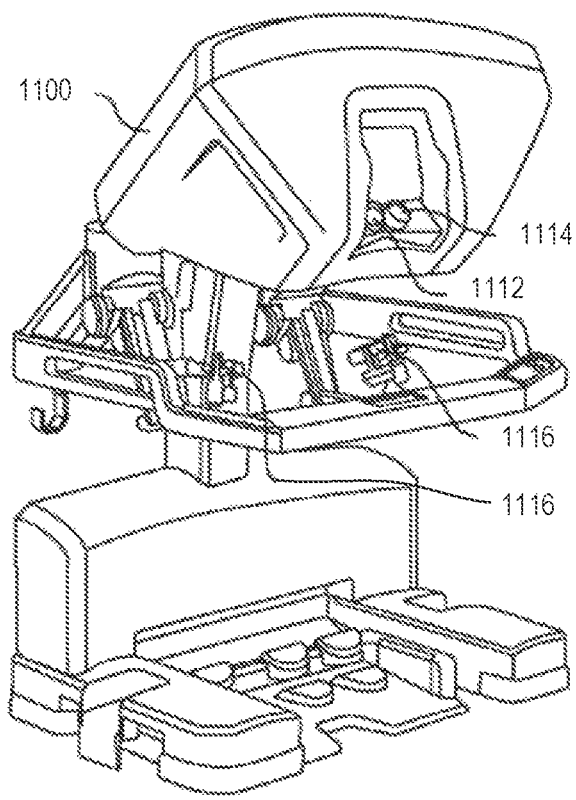
FIG. 2 is a perspective view of a user control console of the teleoperated surgery system shown in FIG. 1.

FIG. 2 is a perspective view of the control unit 1100. The control unit 1100 includes a left eye display 1112 and a right eye display 1114 for presenting the surgeon S with a coordinated stereo view of the surgical site that enables depth perception. The control unit 1100 further includes one or more input control devices 1116, which in turn cause the manipulator unit 1200 (shown in FIG. 1) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the control unit 1100 provides the surgeon S with a strong sense of directly controlling the tools 1400. To this end, position, force, and tactile feedback sensors (not shown) may be employed to transmit position, force, and tactile sensations from the tools 1400 back to the surgeon's hands through the input control devices 1116.

The control unit 1100 is shown in FIG. 1 as being in the same room as the patient so that the surgeon S can directly monitor the procedure, be physically present if necessary, and speak to an assistant directly rather than over the telephone or other communication medium. In other embodiments, however, the control unit 1100 and the surgeon S can be in a different room, a completely different building, or other remote location from the patient allowing for remote surgical procedures.

Figure 3:
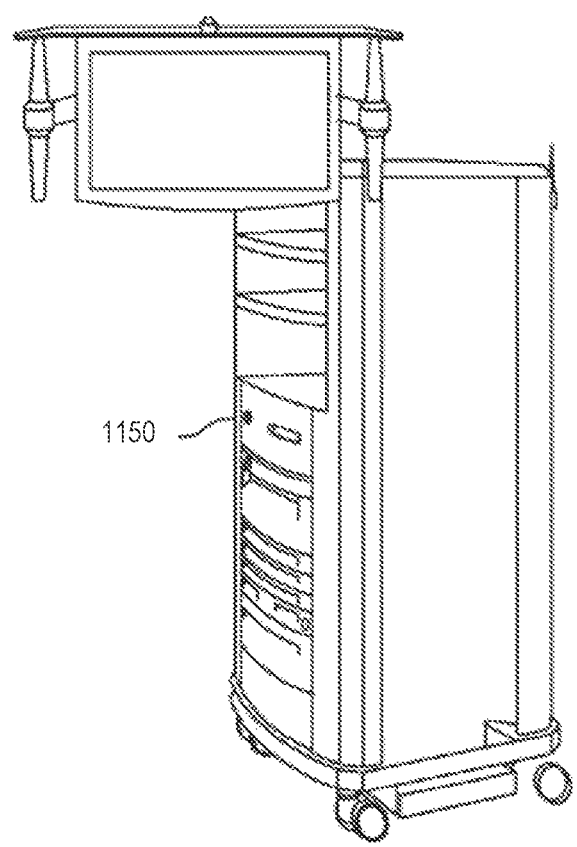
FIG. 3 is a perspective view of an optional auxiliary unit of the teleoperated surgery system shown in FIG. 1.

FIG. 3 is a perspective view of the auxiliary unit 1150. The auxiliary unit 1150 can be coupled with the endoscope 1170, and can include one or more processors to process captured images for subsequent display, such as via the control unit 1100, or on another suitable display located locally and/or remotely. For example, where a stereoscopic endoscope is used, the auxiliary unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
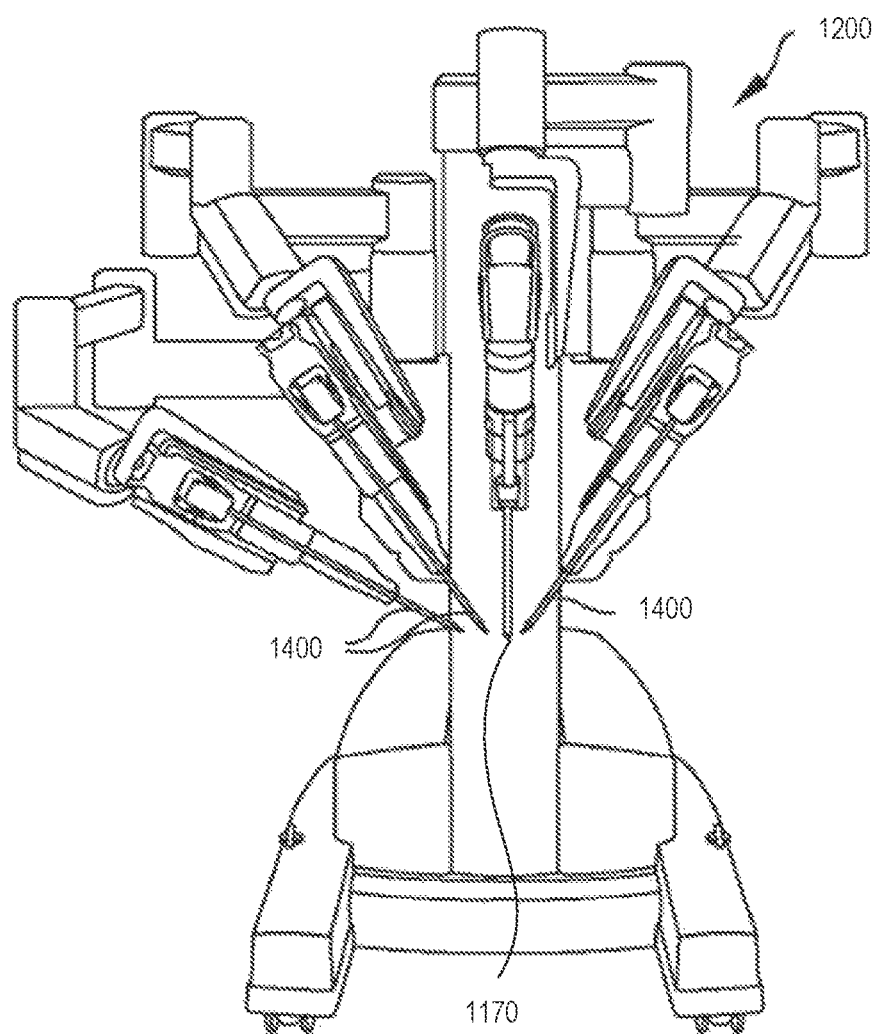
FIG. 4 is a front view of a manipulator unit, including a set of instruments, of the teleoperated surgery system shown in FIG. 1.

FIG. 4 shows a front perspective view of the manipulator unit 1200. The manipulator unit 1200 includes the components (e.g., arms, linkages, motors, sensors, and the like) to provide for the manipulation of the tools 1400 and the imaging device 1170, such as a stereoscopic endoscope, used for the capture of images of the site of the procedure. Specifically, the tools 1400 and the imaging device 1170 can be manipulated by teleoperated mechanisms having a number of joints. Moreover, the tools 1400 and the imaging device 1170 are positioned and manipulated through incisions or natural orifices in the patient P in a manner such that a kinematic remote center is maintained at the incision or orifice. In this manner, the incision size can be minimized.

Figure 5:
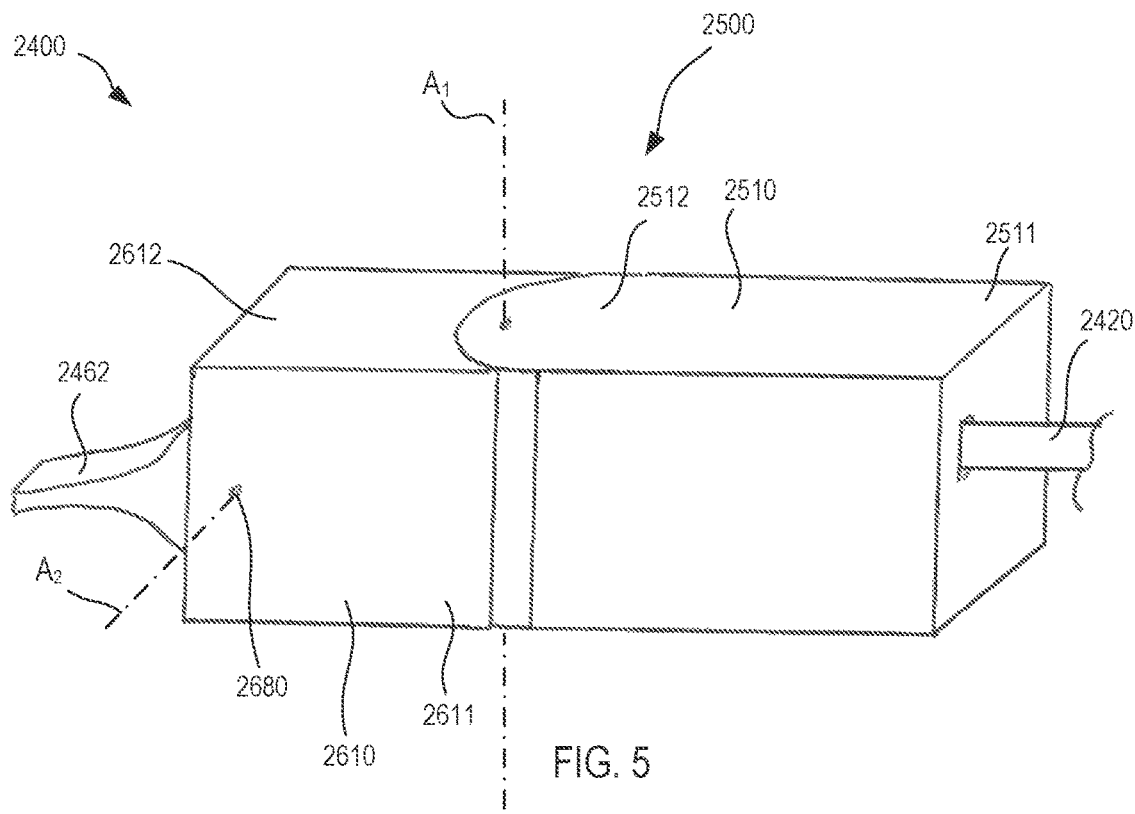
FIG. 5 is a diagrammatic perspective view of a portion of an instrument of a surgery system in a first configuration, according to an embodiment.
Figure 6:
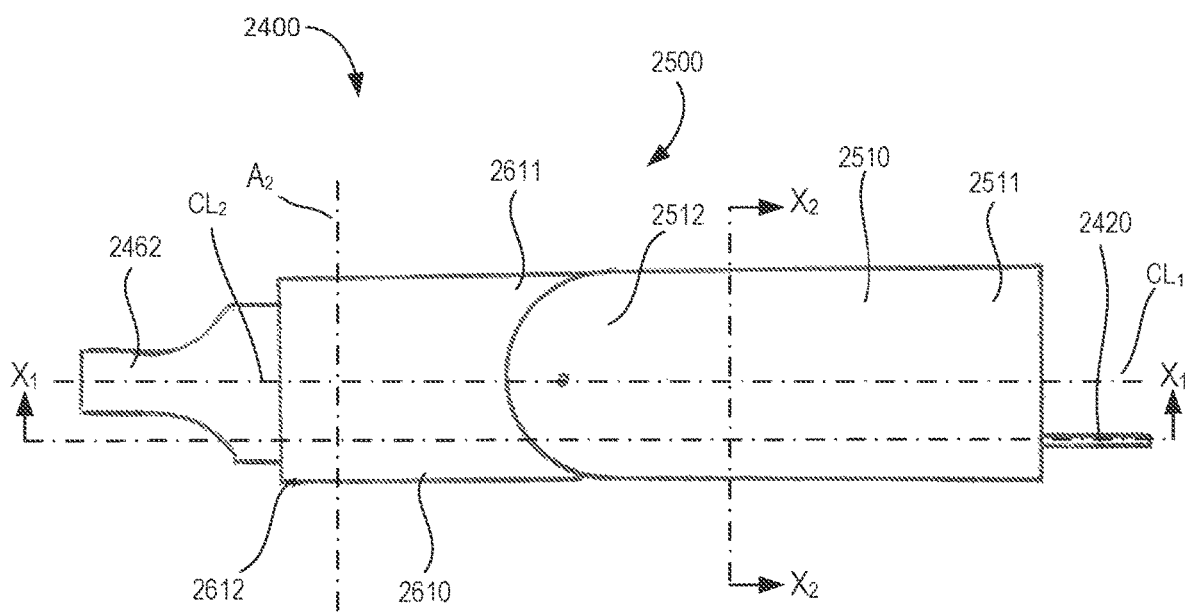
FIGS. 6 and 7 are diagrammatic top views of the portion of the instrument shown in FIG. 5 in the first configuration (FIG. 6) and a second configuration (FIG. 7).
Figure 7:
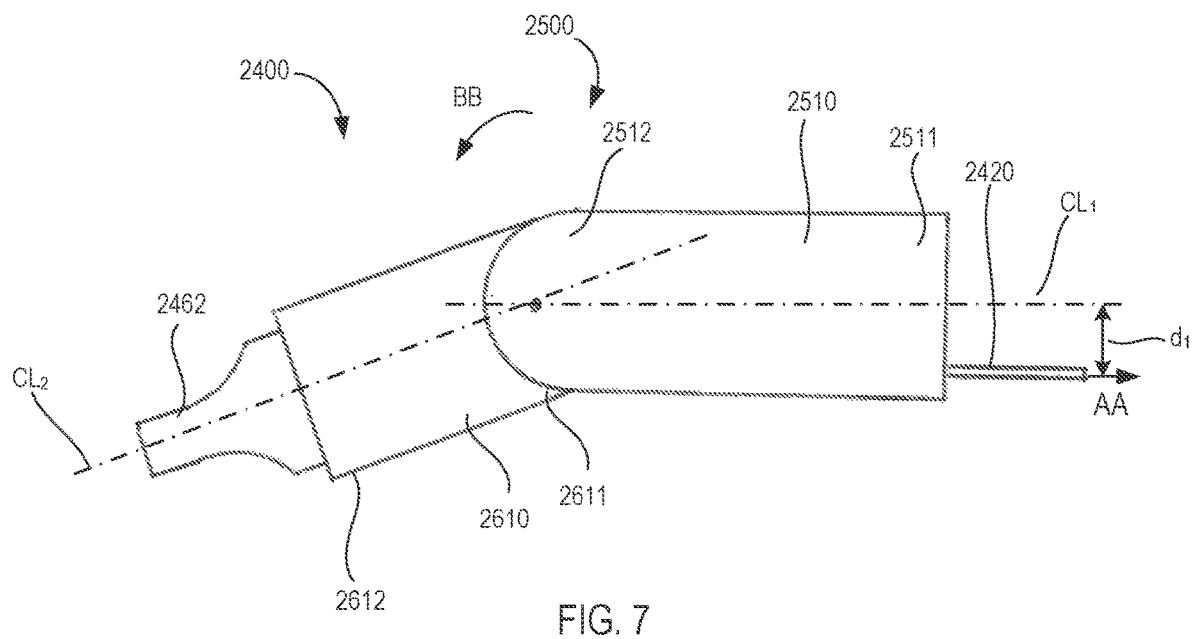
Figure 8:
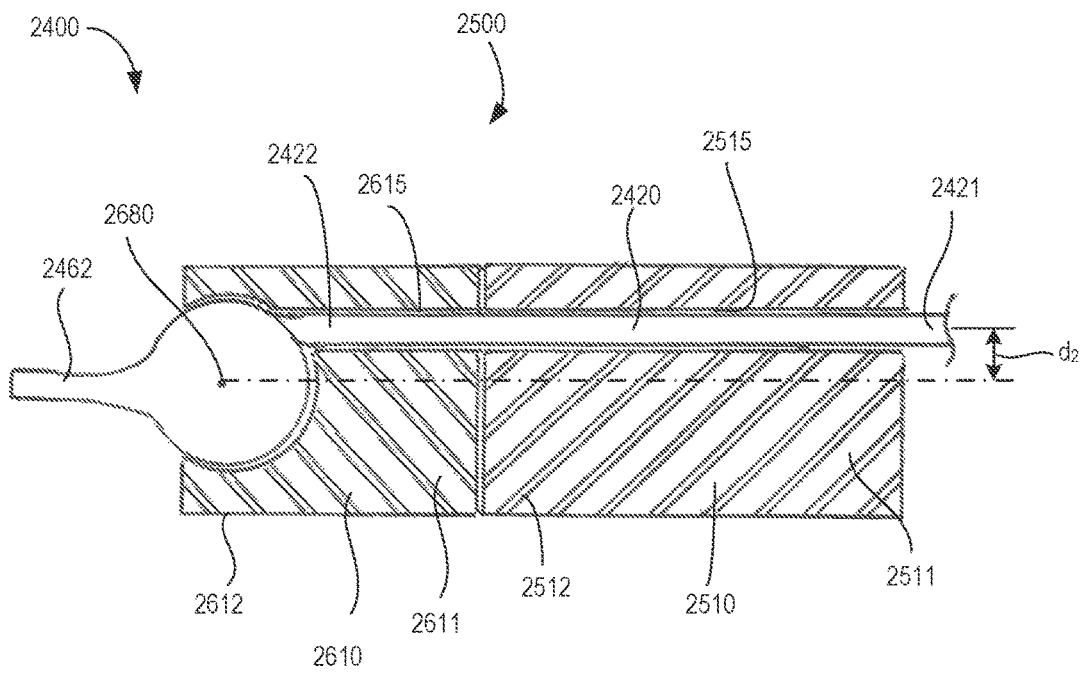
FIGS. 8 and 9 are diagrammatic front cross-sectional views of the portion of the instrument taken along the line $X_1$-$X_1$ shown in FIG. 6, in the first configuration (FIG. 8) and a third configuration (FIG. 9).
Figure 9:
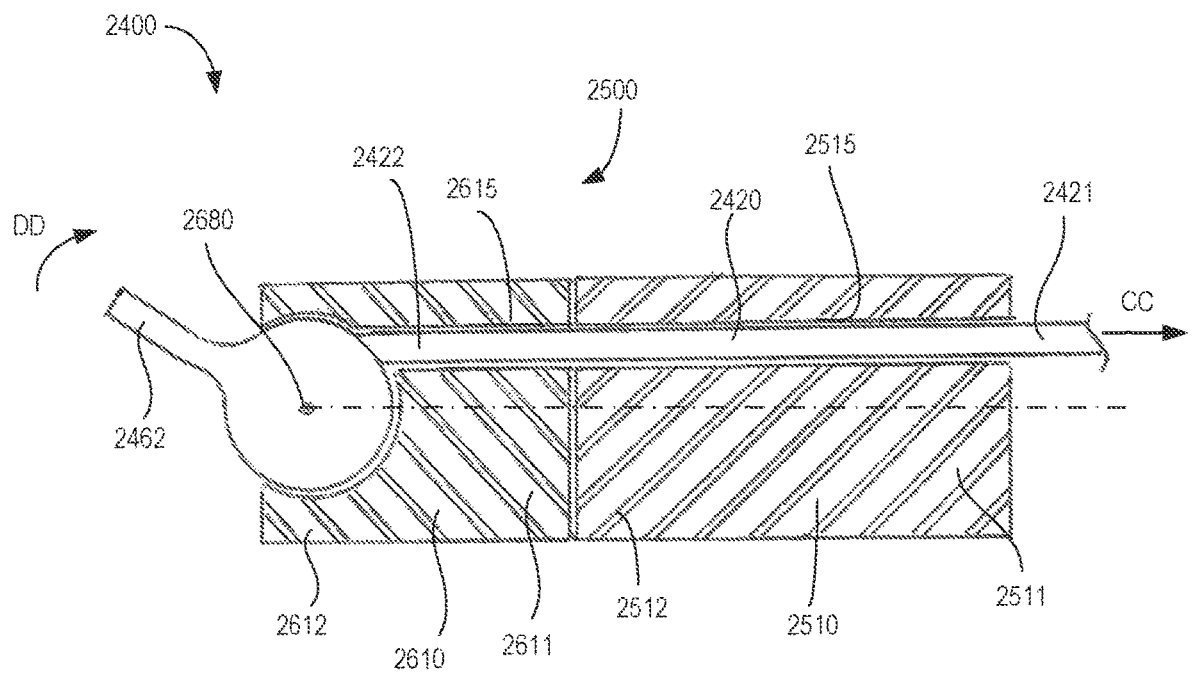

FIGS. 5-10 are diagrammatic illustrations of various portions of an instrument 2400, according to an embodiment. In some embodiments, the instrument 2400 or any of the components therein are optionally parts of a surgical system that performs surgical procedures, and which can include a manipulator unit, a series of kinematic linkages, a series of cannulas, or the like. The instrument 2400 (and any of the instruments described herein) can be used in any suitable surgical system, such as the MIRS system 1000 shown and described above. The instrument 2400 includes a wrist assembly 2500, a band 2420 (which acts as a tension member), and a tool member 2462. As described herein, the instrument 2400 is configured such that movement of the band 2420 produces movement of the wrist assembly 2500 (as shown in FIG. 7), movement of the tool member 2462 (as shown in FIG. 9), or both movement of the wrist assembly 2500 and movement of the tool member 2462.

The wrist assembly 2500 includes a proximal first link 2510 and a distal second link 2610. The first link 2510 has a proximal end portion 2511 and a distal end portion 2512. The proximal end portion 2511 is coupled to a shaft (not shown). Although the shaft is not shown in FIGS. 5-10, the proximal end portion 2511 can be coupled to any suitable shaft, such as the shaft 5410 or the shaft 7410 shown and described herein. Moreover, the proximal end portion 2511 of the first link 2510 can be coupled to the shaft via any suitable mechanism, such as welding, interference fit, adhesive, etc. As described below, the distal end portion 2512 is coupled at a revolute joint to the second link 2610. In this manner, the first link 2510 and the second link 2610 form the wrist assembly 2500 having a first axis of rotation $A_1$ (which functions as the pitch axis, the term pitch is arbitrary) about which the second link can rotate relative to the first link.

Figure 10:
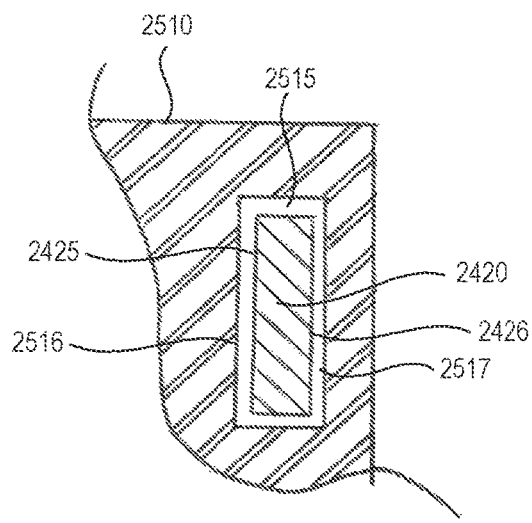
FIG. 10 is a diagrammatic side cross-sectional view of the portion of the instrument taken along the line $X_2$-$X_2$ shown in FIG. 6.

As shown in FIGS. 6 and 7, the first link 2510 defines a longitudinal center line $CL_1$ that intersects the first axis of rotation $A_1$. Referring to FIGS. 8-10, a first guide channel 2515 is defined in the first link 2510. A distal end portion 2422 of the band 2420 moves within the first guide channel 2515. More particularly, the first link 2510 includes an inner guide surface 2516 and an outer guide surface 2517 that each form a portion of the boundary of the first guide channel 2515. As shown in FIG. 10, a portion of the inner guide surface 2516 taken within a cross-sectional plane normal to the longitudinal center line $CL_1$ of the first link 2510 (or a longitudinal center line of the first guide channel 2515) is linear. Similarly, a portion of the outer guide surface 2517 taken within the cross-sectional plane normal to the longitudinal center line $CL_1$ of the first link 2510 (or the longitudinal center line of the first guide channel 2515) is linear. As described below, this arrangement allows the inner guide surface 2516 to contact a corresponding inner contact surface 2425 of the band 2420 along a linear cross-sectional contact surface (as opposed to solely at a single point within the cross section) when the second link 2610 rotates relative to the first link 2510 in a first direction. This arrangement also allows the outer guide surface 2517 to contact a corresponding outer contact surface 2426 of the band 2420 along a linear cross-sectional contact surface when the second link 2610 rotates relative to the first link 2510 in a second direction opposite the first direction.

Referring to FIGS. 6 and 7, the first guide channel 2515 (and therefore the portion of the band 2420 therein) is offset from the longitudinal center line $CL_1$ of the first link 2510 and the first axis of rotation $A_1$ by a distance $d_1$. In this manner, application of a tension force on the band 2420 (indicated by the proximally-directed arrow AA in FIG. 7) produces a torque about the first axis of rotation $A_1$, which results in rotation of the second link 2610 relative to the first link 2510, as shown by the arrow BB in FIG. 7. Referring to FIGS. 8 and 9, the first guide channel 2515 (and therefore the portion of the band 2420 therein) is offset from the second axis of rotation $A_2$ by a distance $d_2$. In this manner, application of a tension force on the band 2420 (indicated by the proximally-directed arrow CC in FIG. 9) produces a torque on the tool member 2462 about the second axis of rotation $A_2$, which results in rotation of the tool member 2462 relative to the second link 2610, as shown by the arrow DD in FIG. 9.

The second link 2610 has a proximal end portion 2611 and a distal end portion 2612. As described above, the proximal end portion 2611 is rotatably coupled to the distal end portion 2512 of the first link 2510 to form a wrist joint. For example, in some embodiments, the proximal end portion 2611 can be coupled to the distal end portion 2512 via a pinned joint, such as the pinned joint between the proximal clevis 220 and the distal clevis 230 shown and described in U.S. Pat. No. 8,821,480 B2 (filed Jul. 16, 2008), entitled "Four-Cable Wrist with Solid Surface Cable Channels," which is incorporated herein by reference in its entirety. In other embodiments, the proximal end portion 2611 can be coupled to the distal end portion 2512 via mating disc surfaces, such as the types shown and described in U.S. Patent Application Publ. No. US 2017/0120457 A1 (filed Feb. 20, 2015), entitled "Mechanical Wrist Joints with Enhanced Range of Motion, and Related Devices and Methods," which is incorporated herein by reference in its entirety.

The distal end portion 2612 of the second link 2610 includes a connector 2680 that is coupled to the tool member 2462 such that the tool member 2462 rotates relative to the wrist assembly 2500 about a second axis of rotation $A_2$. As shown in FIG. 5, the second axis of rotation $A_2$ (also referred to as the yaw axis or the grip axis) is non-parallel to the first axis of rotation $A_1$. Thus, the instrument 2400 provides for up to three degrees of freedom (i.e., a pitch motion about the first axis of rotation $A_1$, a yaw rotation about the second axis of rotation $A_2$, and a grip motion about the second axis of rotation $A_2$). Although the second axis of rotation $A_2$ is shown as being normal to the first axis of rotation $A_1$, in other embodiments, the second axis of rotation $A_2$ can be offset from the first axis of rotation $A_1$ by any suitable angle. The connector 2680 can be any suitable connector to rotatably couple the tool member 2462 to the second link 2610 to form a tool joint. For example, in some embodiments, the connector 2680 can include a clevis and a pin, such as the pinned joints shown and described in U.S. Pat. No. 9,204,923 B2 (filed Jul. 16, 2008), entitled "Medical Instrument Electronically Energized Using Drive Cables," which is incorporated herein by reference in its entirety. In other embodiments, the connector 2680 can include a compliant mechanism, such as the compliant mechanisms shown and described in International Patent Publication No. WO 2016/123139 A2 (filed Jan. 26, 2016), entitled "Rolling-Contact Joint Mechanisms and Methods," which is incorporated herein by reference in its entirety.

As shown in FIG. 7, the second link 2610 defines a longitudinal center line $CL_2$ that intersects the first axis of rotation $A_1$. When the wrist assembly 2500 is in the first configuration (FIGS. 5 and 6), the longitudinal centerline $CL_1$ of the first link 2510 and the longitudinal center line $CL_2$ of the second link 2610 are collinear (and are collectively identified as CL in FIG. 6). When the second link 2610 rotates relative to the first link 2510 (i.e., rotates in pitch), the longitudinal centerline $CL_1$ and the longitudinal center line $CL_2$ form a pitch angle.

Referring to FIGS. 8-9, a second guide channel 2615 is defined in the second link 2610. The distal end portion 2422 of the band 2420 moves within the second guide channel 2615. Although not shown in FIG. 10, the second link 2610 includes an inner guide surface and an outer guide surface (similar to the inner guide surface 2516 and the outer guide surface 2517, respectively) that each form a portion of the boundary of the second guide channel 2615. As described above with reference to the guide surfaces of the first link 2515, the inner guide surface and the outer guide surface of the second link 2610 contact corresponding surfaces of the band 2420 when the second link 2610 rotates relative to the second link 2610. Referring to FIG. 6, the second guide channel 2615 (and therefore the portion of the band 2420 therein) is offset from the longitudinal center line $CL_1$ of the second link 2610 and the first axis of rotation $A_1$ by a distance $d_1$. In this manner, application of a tension force on the band 2420 (indicated by the proximally-directed arrow AA in FIG. 7) produces a torque about the first axis of rotation $A_1$, which results in rotation of the second link 2610 relative to the first link 2510, as shown by the arrow BB in FIG. 7. Referring to FIGS. 8 and 9, the second guide channel 2615 (and therefore the portion of the band 2420 therein) is offset from the second axis of rotation $A_2$ by a distance $d_2$. In this manner, application of a tension force on the band 2420 (indicated by the proximally-directed arrow CC in FIG. 9) produces a torque on the tool member 2462 about the second axis of rotation $A_2$, which results in rotation of the tool member 2462 relative to the second link 2610, as shown by the arrow DD in FIG. 9.

The tool member 2462 is coupled to the wrist assembly 2500 and rotates relative to the wrist assembly about the second axis of rotation $A_2$. In this manner, a distal portion (e.g., an engagement portion) of the tool member 2462 can engage or manipulate a target tissue during a surgical procedure. The tool member 2462 (or any of the tool members described herein) can be any suitable medical tool member. For example, in some embodiments, the tool member 2462 (or any of the tool members described herein) can include an engagement surface that functions as a gripper, cutter, tissue manipulator, or the like. In other embodiments, the tool member 2462 (or any of the tool members described herein) can be an energized tool member that is used for cauterization procedures. Although only one tool member 2462 is shown, in other embodiments, the instrument 2400 includes two moving tool members that cooperatively perform gripping or shearing functions. In this manner, the tool member 2462 can form a portion of an end effector for the instrument 2400.

The band 2420 has a proximal end portion 2421 and a distal end portion 2422. The proximal end portion 2421 extends outside of the wrist assembly 2500, through the shaft (not shown), and is coupled to an actuator (not shown). The actuator can move the proximal end portion 2421 of the band by any suitable mechanism to produce a resulting movement (or force) at the distal end portion 2422 of the band (as shown by arrow AA in FIG. 7 and the arrow CC in FIG. 9). In some embodiments, the backend of the instrument 2400 is motor driven, and is thus suitable for a teleoperated surgical system. The distal end portion 2422 of the band 2420 is within the first guide channel 2515 and the second guide channel 2615, and is coupled to the tool member 2462. In this manner, as described herein, movement of (or a force applied to) the band 2420 produces rotation of the tool member 2462, rotation of the second link 2610, or rotation of both the tool member 2462 and the second link 2610. The distal end portion 2422 of the band 2420 can be coupled to the tool member 2462 by any suitable mechanism. For example, in some embodiments, the distal end portion 2422 is coupled to the tool member 2462 by a pin or protrusion that engages (or is received within) a connection portion of the tool member 2462. In other embodiments, the distal end portion 2422 is coupled to the tool member 2462 via an adhesive. In yet other embodiments, the distal end portion 2422 of the band is wrapped about a pulley portion of the tool member 2462.

The band 2420 (and any of the bands described herein) can have any suitable shape. For example, although FIG. 10 shows the band 2420 as having a rectangular cross-sectional shape (taken within a cross-sectional plane normal to the longitudinal center line of the band 2420), in other embodiments, the band 2420 can have any suitable cross-sectional shape. For example, in some embodiments, the band 2420

(and any of the bands described herein) can have a trapezoidal shape. In other embodiments, the band 2420 (and any of the bands described herein) can include slightly curved surfaces. For example, although the inner contact surface 2425 and the outer contact surface 2426 are shown as being linear (within a cross-sectional plane normal to the longitudinal center line of the band 2420), in other embodiments, either the inner contact surface 2425, the outer contact surface 2426, or both are curved or "crowned." Moreover, the band 2420 (and any of the bands described herein) can be constructed from any suitable materials. For example, in some embodiments, the band 2420 (and any of the bands described herein) can be constructed from a series of laminates that are bonded together (e.g., via an adhesive). In other embodiments, the laminates can be joined by any other suitable method. The laminates can be constructed from any suitable material, including tungsten, steel, or any suitable polymer.

The use of the band 2420 can provide for a low-cost, disposable instrument that is suitable for surgical procedures (including minimally-invasive procedures). In use, the distal end portion of the instrument 2400 provides for up to three degrees of freedom, and can be moved between multiple different configurations to perform a variety of surgical operations. For example, in some situations, movement of the distal end portion 2422 of the band 2420, as shown by the proximally-directed arrow AA in FIG. 7, produces rotation of the second link 2610 about the pitch axis $A_1$ (as shown by the arrow BB in FIG. 7). The amount of rotation, the force needed to produce the desired rotation, and the amount of movement of the band 2420 can be controlled by, among other things, the offset distance $d_1$ between the band 2420 and the pitch axis $A_1$ and the curvature (or routing) of the distal end portion 2422 of the band 2420 within the first guide channel 2515 and the second guide channel 2615. For example, a greater offset distance $d_1$ will produce a greater moment arm, but will, in turn, increase the overall size of the wrist assembly 2500. In other situations, movement of the distal end portion 2422 of the band 2420, as shown by the proximally-directed arrow CC in FIG. 9, produces rotation of the tool member 2462 about the yaw axis $A_2$ (as shown by the arrow DD in FIG. 9). This produces either a gripping motion (e.g., where there are two tool members) or a yaw motion. The amount of rotation, the force needed to produce the desired rotation, and the amount of movement of the band 2420 can be controlled by, among other things, the offset distance $d_2$ between the band 2420 and the yaw axis $A_2$ and the curvature (or routing) of the distal end portion 2422 of the band 2420 within the first guide channel 2515 and the second guide channel 2615. For example, a greater offset distance $d_2$ will produce a greater moment arm, but will, in turn, increase the overall size of the wrist assembly 2500.

Although the first link 2510 and the second link 2610 are shown as having a rectangular cross-sectional shape, in other embodiments, either the first link 2510, the second link 2610, or both the first link 2510 and the second link 2610 can have any suitable cross-sectional shape. For example, in some embodiment, either the first link 2510, the second link 2610, or both the first link 2510 and the second link 2610 can have substantially circular cross-sectional shape (i.e., the wrist assembly 2500 can be substantially cylindrical).

Figure 11:
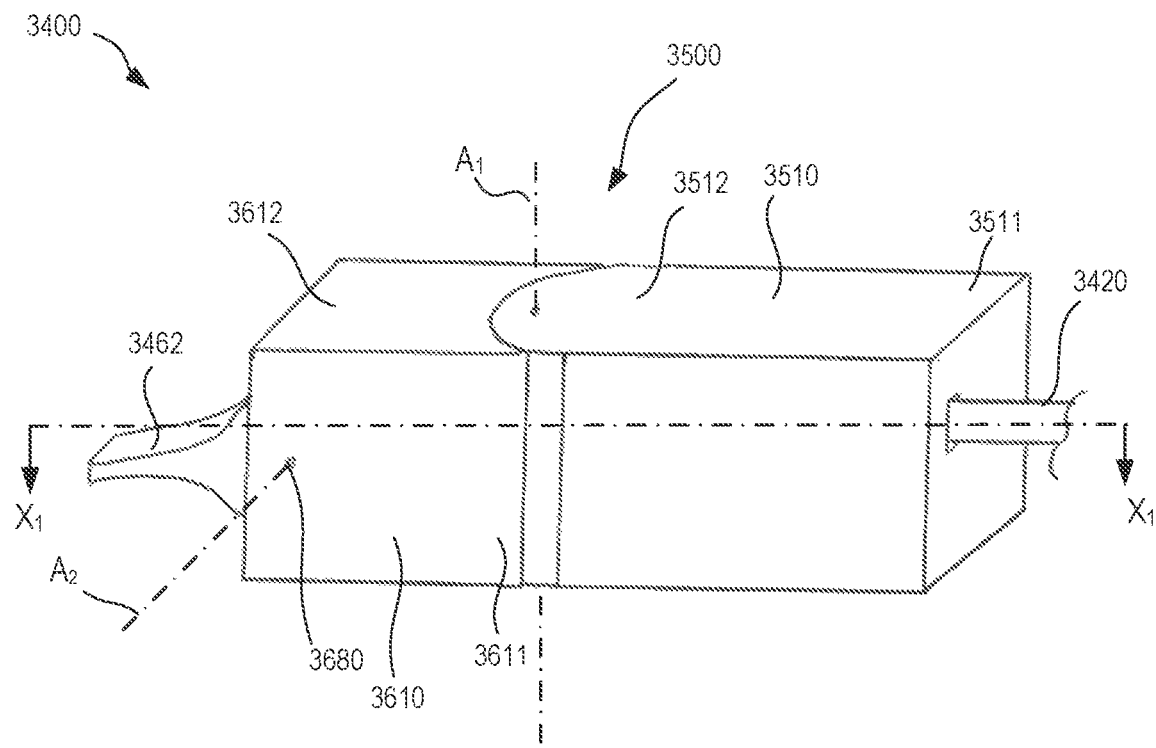
FIG. 11 is a diagrammatic perspective view of a portion of an instrument of a surgery system in a first configuration, according to an embodiment.
Figure 12:
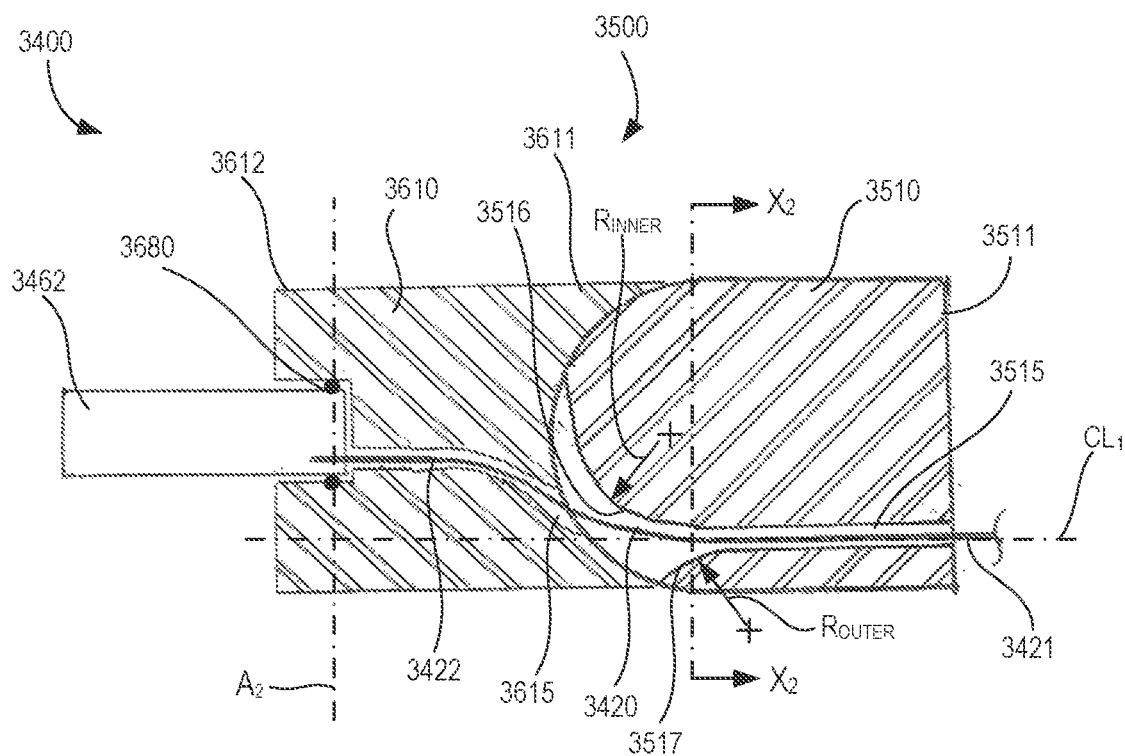
FIGS. 12-14 are diagrammatic top cross-sectional views of the portion of the instrument taken along the line $X_1$-$X_1$ shown in FIG. 11, in a first configuration (FIG. 12), a second configuration (FIG. 13), and a third configuration (FIG. 14).
Figure 13:
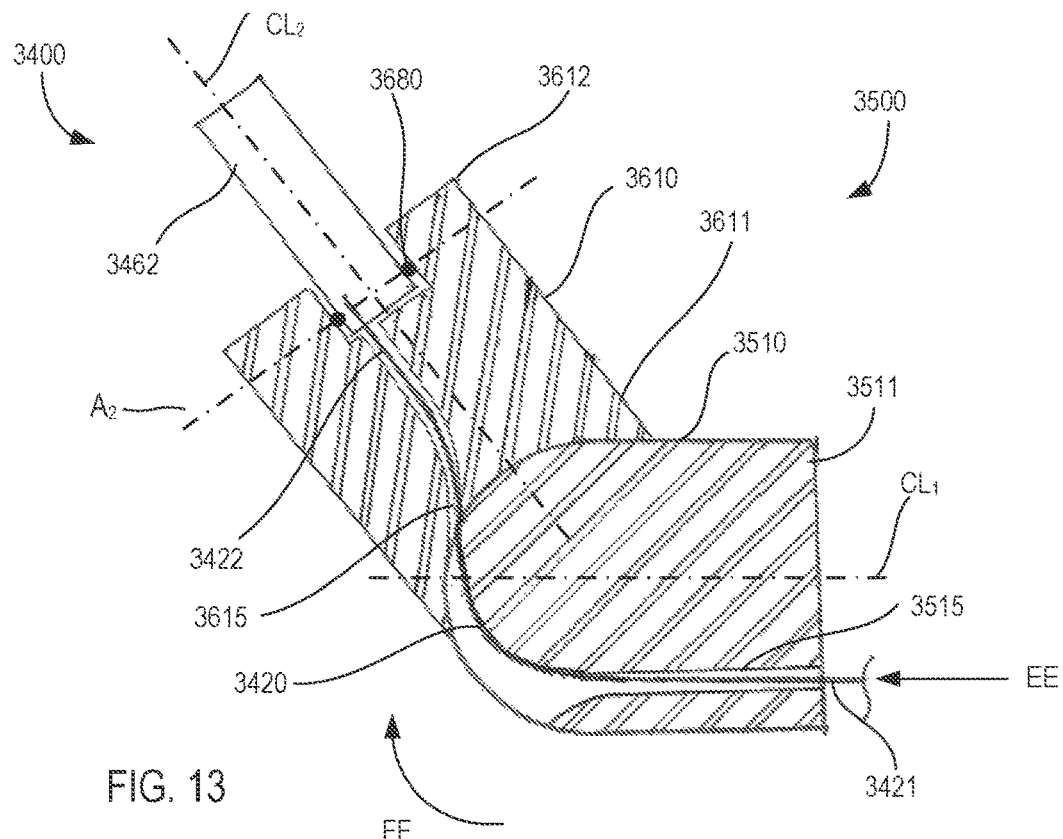
Figure 14:
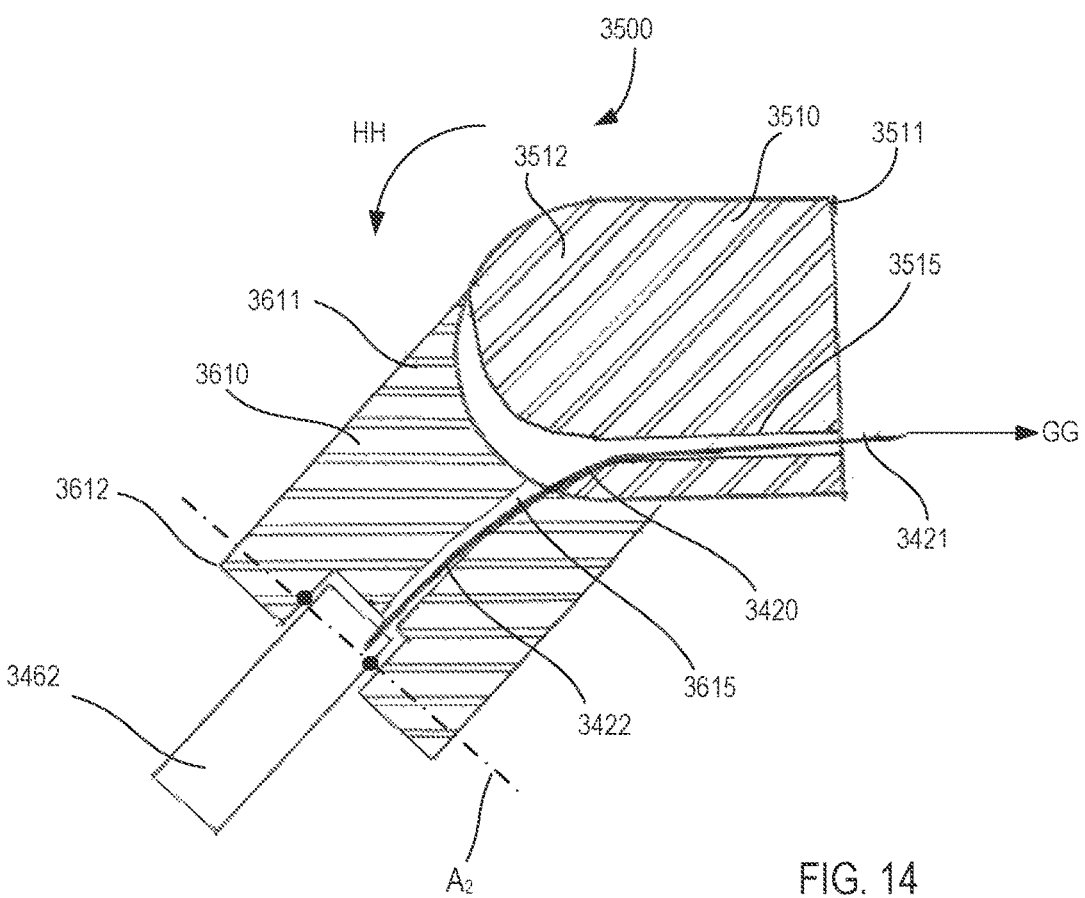

Although the first guide channel 2515 and the second guide channel 2615 are shown as being substantially linear along the longitudinal center line $CL_1$ of the first link 2510 and the longitudinal center line $CL_2$ of the second link 2610, respectively, in other embodiments, the first guide channel 2515, the second guide channel 2615, or both the first guide channel 2515 and the second guide channel 2615 can have any suitable longitudinal shape to ensure that the band 2420 is routed through the wrist assembly 2500 to maintain the desired tension and conservation of length during the entire range of motion of the second link 2610 and the tool member 2462. For example, FIGS. 11-17 are diagrammatic illustrations of various portions of an instrument 3400, according to an embodiment. The instrument 3400 includes a wrist assembly 3500, a band 3420 (which acts as a tension member), and a tool member 3462. As described herein, the instrument 3400 is configured such that movement of the band 3420 produces movement of the wrist assembly 3500 (as shown in FIGS. 13-14), movement of the tool member 3462 (not shown, but similar to the movement describe above with reference to FIG. 9), or both movement of the wrist assembly 3500 and movement of the tool member 3462.

The wrist assembly 3500 includes a proximal first link 3510 and a distal second link 3610. The first link 3510 has a proximal end portion 3511 and a distal end portion 3512. The proximal end portion 3511 is coupled to a shaft (not shown). Although the shaft is not shown in FIGS. 11-17, the proximal end portion 3511 can be coupled to any suitable shaft, such as the shaft 5410 or the shaft 7410 shown and described herein. Moreover, the proximal end portion 3511 of the first link 3510 can be coupled to the shaft via any suitable mechanism, such as welding, interference fit, adhesive, etc. As described below, the distal end portion 3512 is coupled to the second link 3610 at a revolute joint. In this manner, the first link 3510 and the second link 3610 form the wrist assembly 3500 having a first axis of rotation $A_1$ (which functions as the pitch axis, the term pitch is arbitrary) about which the second link 3610 rotates relative to the first link.

Figure 17:
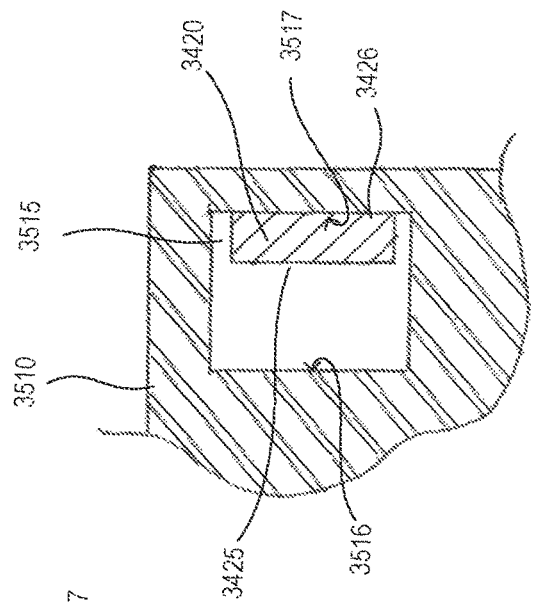
FIGS. 15-17 are diagrammatic side cross-sectional views of the portion of the instrument taken along the line $X_2$-$X_2$ shown in FIG. 12, in the first configuration (FIG. 15), the second configuration (FIG. 16), and the third configuration (FIG. 17).
Figure 16:
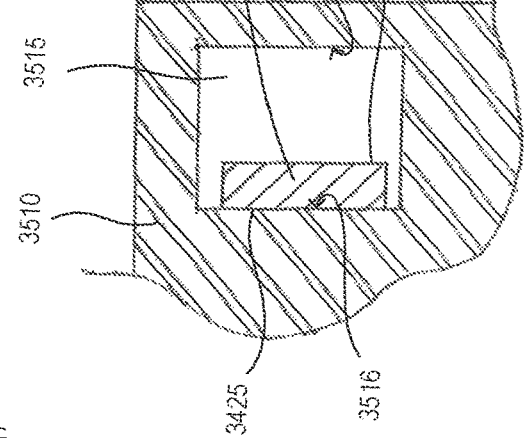
Figure 15:
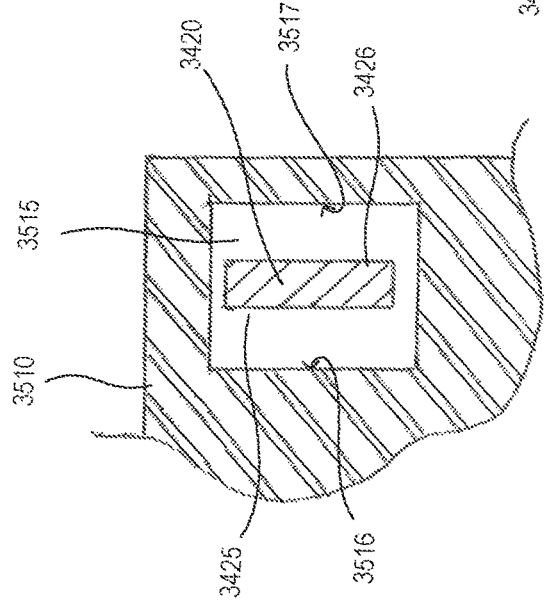

As shown in FIG. 13, the first link 3510 defines a longitudinal center line $CL_1$ that intersects the first axis of rotation $A_1$. A first guide channel 3515 is defined in the first link 3510, and a distal end portion 3422 of the band 3420 is in and moves along the first guide channel 3515. More particularly, as shown in FIGS. 15-17, the first link 3510 includes an inner guide surface 3516 and an outer guide surface 3517 that each form a portion of the boundary of the first guide channel 3515. As shown in FIGS. 12-14, the first guide channel 3515 is curved along the longitudinal center line $CL_1$ of the first link 3510. Specifically, as shown in FIG. 12, the inner guide surface 3516 is curved along and the longitudinal center line $CL_1$ by a radius of curvature $R_{INNER}$, and the outer guide surface 3517 is curved along and the longitudinal center line $CL_1$ by a radius of curvature $R_{OUTER}$. In this manner, when the second link 3610 rotates relative to the first link 3510 about the first axis of rotation $A_1$ (i.e., pitch motion), the band 3420 can contact the curved portions of the inner guide surface 3516 and the outer guide surface 3517 to maintain the desired bend geometry, band tension, and the like during actuation of the instrument 3400. In some embodiments, the radius of curvature $R_{INNER}$ is different from the radius of curvature $R_{OUTER}$. Moreover, although the curvature of the inner guide surface 3516 and the outer guide surface 3517 is shown as being defined by a single radius of curvature ($R_{INNER}$ and $R_{OUTER}$, respectively), in other embodiments, the curvature of the first guide channel (or any of the guide channels described herein) can be defined by multiple different radii of curvature.

As shown in FIGS. 15-17, a portion of the inner guide surface 3516 taken within a cross-sectional plane normal to the longitudinal center line $CL_1$ of the first link 3510 (or a longitudinal center line of the first guide channel 3515) is linear. Similarly, a portion of the outer guide surface 3517 taken within the cross-sectional plane normal to the longitudinal center line $CL_1$ of the first link 3510 (or the longitudinal center line of the first guide channel 3515) is linear. As described below, this arrangement allows the inner guide surface 3516 to contact a corresponding inner contact surface 3425 of the band 3420 along a linear cross-sectional contact surface (as opposed to solely at a single point within the cross section) when the second link 3610 rotates relative to the first link 3510 in a first direction. This arrangement also allows the outer guide surface 3517 to contact a corresponding outer contact surface 3426 of the band 3420 along a linear cross-sectional contact surface when the second link 3610 rotates relative to the first link 3510 in a second direction opposite the first direction.

The first guide channel 3515 (and therefore the portion of the band 3420 therein) is offset from the longitudinal center line $CL_1$ of the first link 3510 and the first axis of rotation $A_1$. In this manner, application of a force on the band 3420 (indicated by the arrow EE in FIG. 13 and the arrow GG in FIG. 14) produces a torque about the first axis of rotation $A_1$, which results in rotation of the second link 3610 relative to the first link 3510, as shown by the arrow FF in FIG. 13 and the arrow HH in FIG. 14. The first guide channel 3515 (and therefore the portion of the band 3420 therein) is also offset from the second axis of rotation $A_2$. In this manner, application of a force on the band 3420 can also produce a torque on the tool member 3462 about the second axis of rotation $A_2$, which results in rotation of the tool member 3462 relative to the second link 3610.

The second link 3610 has a proximal end portion 3611 and a distal end portion 3612. As described above, the proximal end portion 3611 is rotatably coupled to the distal end portion 3512 of the first link 3510 to form a wrist joint. For example, in some embodiments, the proximal end portion 3611 can be coupled to the distal end portion 3512 via a pinned joint, such as the pinned joint between the proximal clevis 220 and the distal clevis 230 shown and described in U.S. Pat. No. 8,821,480 B2 (filed Jul. 16, 2008), entitled "Four-Cable Wrist with Solid Surface Cable Channels," which is incorporated herein by reference in its entirety. In other embodiments, the proximal end portion 3611 can be coupled to the distal end portion 3512 via mating disc surfaces, such as the types shown and described in U.S. Patent Application Pub. No. US 2017/0120457 A1 (filed Feb. 20, 2015), entitled "Mechanical Wrist Joints with Enhanced Range of Motion, and Related Devices and Methods," which is incorporated herein by reference in its entirety.

The distal end portion 3612 of the second link 3610 includes a connector 3680 that is coupled to the tool member 3462 such that the tool member 3462 rotates relative to the wrist assembly 3500 about a second axis of rotation $A_2$. As shown in FIG. 11, the second axis of rotation $A_2$ is non-parallel to the first axis of rotation $A_1$. The axis $A_2$ functions both as a yaw axis (the term yaw is arbitrary) as tool members rotate together and as a grip axis as tool members rotate in opposition to each other. Thus, the instrument 3400 provides for up to three degrees of freedom (i.e., a pitch rotation about the first axis of rotation $A_1$, a yaw rotation about the second axis of rotation $A_2$, and a grip motion about the second axis of rotation $A_2$). The connector 3680 can be any suitable connector to rotatably couple the tool member 3462 to the second link 3610 to form a tool joint. For example, in some embodiments, the connector 3680 can include a clevis and a pin, such as the pinned joints shown and described in U.S. Pat. No. 9,204,923 B2 (filed Jul. 16, 2008), entitled "Medical Instrument Electronically Energized Using Drive Cables," which is incorporated herein by reference in its entirety. In other embodiments, the connector 3680 can include a compliant mechanism, such as the compliant mechanisms shown and described in International Patent Publication No. WO 2016/123139 A2 (filed Jan. 26, 2016), entitled "Rolling-Contact Joint Mechanisms and Methods," which is incorporated herein by reference in its entirety. The use of compliant mechanisms for attachment of the tool member 3462 can allow the tool member to have enhanced range of motion with fewer parts as compared with that available with a pinned joint.

As shown in FIG. 13, the second link 3610 defines a longitudinal center line $CL_2$ that intersects the first axis of rotation $A_1$. When the wrist assembly 3500 is in the first configuration (FIGS. 11 and 12), the longitudinal centerline $CL_1$ of the first link 3510 and the longitudinal center line $CL_2$ of the second link 3610 are collinear. When the second link 3610 rotates relative to the first link 3510 (i.e., pitch motion), the longitudinal centerline $CL_1$ and the longitudinal center line $CL_2$ form a pitch angle (as shown in FIGS. 13 and 14).

Referring to FIGS. 12-14, a second guide channel 3615 is defined in the second link 3610. The distal end portion 3422 of the band 3420 moves within the second guide channel 3615. Although not identified, the second link 3610 includes an inner guide surface and an outer guide surface (similar to the inner guide surface 3516 and the outer guide surface 3517, respectively) that each form a portion of the boundary of the second guide channel 3615. The second guide channel 3615 is curved along the longitudinal center line $CL_2$ of the second link 3610. Specifically, although not identified, the inner guide surface is curved along and the longitudinal center line $CL_2$ by a radius of curvature, and the outer guide surface is curved along and the longitudinal center line $CL_2$ by a radius of curvature. In this manner, when the second link 3610 rotates relative to the first link 3510 about the first axis of rotation $A_1$ (i.e., pitch motion), the band 3420 can contact the curved portions of the inner guide surface and the outer guide surface of the second link 3610 to maintain the desired bend geometry, band tension, and the like during actuation of the instrument 3400.

As described above with reference to the guide surfaces of the first link 3515, the inner guide surface and the outer guide surface of the second link 3610 contact corresponding surfaces of the band 3420 when the second link 3610 rotates relative to the second link 3610. Moreover, the second guide channel 3615 (and therefore the portion of the band 3420 therein) is offset from the longitudinal center line $CL_2$ of the second link 3610 and the first axis of rotation $A_1$. In this manner, application of a force on the band 3420 produces a torque about the first axis of rotation $A_1$, which results in rotation of the second link 3610 relative to the first link 3510. The second guide channel 3615 (and therefore the portion of the band 3420 therein) is also offset from the second axis of rotation $A_2$. In this manner, application of a force on the band 3420 can also produces a torque on the tool member 3462 about the second axis of rotation $A_2$, which results in rotation of the tool member 3462 relative to the second link 3610.

The tool member 3462 is coupled to the wrist assembly 3500 and rotates relative to the wrist assembly about the second axis of rotation $A_2$. In this manner, a distal portion (e.g., an engagement portion) of the tool member 3462 can engage or manipulate a target tissue during a surgical procedure. The tool member 3462 (or any of the tool members described herein) can be any suitable medical tool member. For example, in some embodiments, the tool member 3462 (or any of the tool members described herein) can include an engagement surface that functions as a gripper, cutter, tissue manipulator, or the like. In other embodiments, the tool member 3462 (or any of the tool members described herein) can be an energized tool member that is used for cauterization procedures. Although only one tool member 3462 is shown, in other embodiments, the instrument 3400 includes two moving tool members that cooperatively perform gripping or shearing functions. In this manner, the tool member 3462 can form a portion of an end effector for the instrument 3400.

The band 3420 has a proximal end portion 3421 and a distal end portion 3422. The proximal end portion 3421 extends outside of the wrist assembly 3500, through the shaft (not shown), and is coupled to an actuator (not shown). The actuator can move the proximal end portion 3421 of the band by any suitable mechanism to produce a resulting movement (or force) at the distal end portion 3422 of the band (as shown by arrow EE in FIG. 13 and the arrow GG in FIG. 14). The distal end portion 3422 of the band 3420 is within the first guide channel 3515 and the second guide channel 3615, and is coupled to the tool member 3462. In this manner, as described herein, movement of (or a force applied to) the band 3420 produces rotation of the tool member 3462, rotation of the second link 3610, or rotation of both the tool member 3462 and the second link 3610. The distal end portion 3422 of the band 3420 can be coupled to the tool member 3462 by any suitable mechanism. For example, in some embodiments, the distal end portion 3422 can be coupled to the tool member 3462 by a pin or protrusion that engages (or is received within) a connection portion of the tool member 3462. In other embodiments, the distal end portion 3422 can be coupled to the tool member 3462 via an adhesive. In yet other embodiments, the distal end portion 3422 of the band can be wrapped about a pulley portion of the tool member 3462.

The band 3420 (and any of the bands described herein) can have any suitable shape. Moreover, the band 3420 (and any of the bands described herein) can be constructed from any suitable materials. For example, in some embodiments, the band 3420 (and any of the bands described herein) can be constructed from a series of laminates that are bonded together (e.g., via an adhesive). In other embodiments, the laminates can be joined by any other suitable method. The laminates can be constructed from any suitable material, including tungsten, steel, or any suitable polymer.

The use of the band 3420 can provide for a low-cost, disposable instrument that is suitable for surgical procedures. In use, the distal end portion of the instrument 3400 provides for up to three degrees of freedom, and can be moved between multiple different configurations to perform a variety of surgical operations. For example, in some situations, the second link 3610 can be rotated about the pitch axis $A_1$ in a first direction. As shown in FIG. 13, movement of (or application of a force to) the band 3420 as shown by the arrow EE produces rotation of the second link 3610 relative to the first link 3510 in the first direction shown by the arrow FF. Referring to FIG. 16, during rotation, the inner contact surface 3425 of the band 3420 contacts the inner guide surface 3516 of the first link 3510. Specifically, the inner contact surface 3425 can be wrapped about the curved inner guide surface 3516 (i.e., contact between the inner contact surface 3425 and the inner guide surface 3516 can be maintained) to ensure that the desired tension is maintained within the band 3420, and that motion between the distal end portion 3422 and the proximal end portion 3421 (i.e., coupled to the actuator) is conserved during the entire range of motion of the second link 3610 and the tool member 3462. As shown in FIG. 14, movement of (or application of a force to) the band 3420 as shown by the arrow GG produces rotation of the second link 3610 relative to the first link 3510 in the first direction shown by the arrow HH. Referring to FIG. 17, the outer contact surface 3426 of the band 3420 contacts the outer guide surface 3517 of the first link 3510. Specifically, the outer contact surface 3417 can be wrapped about the curved outer guide surface 3517 (i.e., contact between the outer contact surface 3426 and the outer guide surface 3517 can be maintained) to ensure that the desired tension is maintained within the band 3420, and that motion between the distal end portion 3422 and the proximal end portion 3421 (i.e., coupled to the actuator) is conserved during the entire range of motion of the second link 3610 and the tool member 3462.

In use, in some embodiments, a first portion of a band (e.g., the band 3420) is wrapped about one or more guide surfaces (e.g., the inner guide surface 3516) of a wrist assembly and a second portion of the band is wrapped about a portion (e.g., a pulley portion) of a tool member (e.g., the tool member 3462). In such embodiments, the band is constructed to have sufficient strength to exert the desired torque or force on the wrist assembly or tool member, while also having sufficient flexibility to conform to (or be wrapped about) various structures within the instrument. The flexibility (or stiffness) of the bands described herein is an extensive property of the band, and thus is dependent upon both the material from which the band is formed and certain physical characteristics of the band (e.g., cross-sectional shape, length, boundary conditions, etc.). For example, the flexibility of any of the bands described herein can be increased or decreased by selectively constructing the band from a material having a desired modulus of elasticity, flexural modulus and/or hardness. For example, the flexibility of a band can be increased, for example, by constructing the band of a material having a relatively low modulus of elasticity. In some embodiments, the flexibility of a band can be increased, for example, by constructing the bands of thinner laminates. The flexibility of any of the bands described herein can also be increased or decreased by changing a physical characteristic of the object, such as the shape or cross-sectional area of the object. For example, a band having a length and a cross-sectional area may have a greater stiffness than another band having an identical length but a smaller cross-sectional area. Thus, the flexibility of the band can be increased by decreasing the size and/or changing the shape or orientation of the band. Also, the band stiffness can be changed by changing the number of laminates used.

The stiffness (or inversely, the flexibility) of an elongated object, such as any of the bands described herein, can be characterized by its flexural stiffness. The flexural stiffness of a band can be used to characterize the ease with which the band deflects under a given force (e.g., the ease with which the band deflects when wrapped or moved along a tortuous path within the instruments described herein). The flexural stiffness can be mathematically expressed as shown below:

$$k = \frac{3EI}{L^3} \qquad (1)$$

where k is the flexural stiffness of the band, E is the modulus of elasticity of the material from which the band is constructed, I is the area moment of inertia of the band (defined below), and L is the length of the band. Thus, for a given band length, the stiffness can be decreased (i.e., the flexibility can be increased) by reducing both the modulus of elasticity and the area moment of inertia of the band. The area moment of inertia for a rectangular cross-sectional shape is expressed below as:

$$Ix = \frac{bh^3}{12} \quad (2)$$

where x is the axis about which the band is being bent, b is the length of the side of the rectangle that is parallel to the x-axis (i.e., the "base" of the rectangle), and h is the length of the side of the rectangle that is normal to the x-axis (i.e., the "height" of the rectangle). As evident from this equation, the area moment of inertia for a rectangle is the lowest when the base is the longer of the two sides. Said another way, the flexibility of any of the bands described herein can be maximized by ensuring that cross-sectional shape is oriented to produce the lowest possible area moment of inertia about the desired bend axis. Also, the flexibility of a band can be increased without reducing strength, by constructing it of additional thinner laminates.

Accordingly, in some embodiments, an instrument can include a band that is twisted along its longitudinal center line such that the cross-sectional shape (at various positions along the longitudinal center line) is in a first orientation to produce a low area moment of inertia about a first axis and is in a second orientation to produce a low area moment of inertia about a second axis. This arrangement can allow a single band to be deformed to maintain the desired flexibility about two or more different axes (e.g., a pitch axis and a yaw axis). For example, FIG. 18 shows a cross-sectional view of a portions of an instrument 4400, according to an embodiment. The instrument 4400 includes a wrist assembly 4500, a band 4420, and a tool member 4462. FIGS. 19-21 are cross-sectional views of various portions of the band 4420 taken within a plane normal to the longitudinal center line CL of the band 4420. The instrument 4400 is configured such that movement of the band 4420 produces movement of the wrist assembly 4500 about the pitch axis $A_1$, movement of the tool member 4462 about the yaw axis $A_2$, or both movement of the wrist assembly 4500 and movement of the tool member 4462.

The wrist assembly 4500 includes a proximal first link 4510 and a distal second link 4610. The first link 4510 has a proximal end portion and a distal end portion. The proximal end portion of the first link 4510 is coupled to a shaft (not shown, but similar to any of the shafts described herein), in a similar manner as that described above with reference to the wrist assembly 2500 and the wrist assembly 3500. The distal end portion is coupled to the second link 4610 at a revolute joint. In this manner, the first link 4510 and the second link 4610 form the wrist assembly 4500 having a first axis of rotation $A_1$ (which functions as the pitch axis, the term pitch is arbitrary) about which the second link 4610 rotates relative to the first link.

The second link 4610 has a proximal end portion 4611 and a distal end portion 4612. As described above, the proximal end portion 4611 is rotatably coupled to the first link 4510. The proximal end portion 4611 of the second link 4610 and the distal end portion of the first link 4510 can be coupled together to form any suitable wrist joint. For example, in some embodiments, the second link 4610 can be coupled to the first link 4510 via a pinned joint of the types shown and described herein. In other embodiments, the second link 4610 can be coupled to the first link 4510 via mating disc surfaces of the types shown and described herein. The distal end portion 4612 of the second link 4610 is coupled to a pulley portion 4467 of the tool member 4462 such that the tool member 4462 rotates relative to the wrist assembly 4500 about a second axis of rotation $A_2$. As shown in FIG. 18, the second axis of rotation $A_2$ is non-parallel to the first axis of rotation $A_1$. The axis $A_2$ functions both as a yaw axis (the term yaw is arbitrary) as tool members rotate together and as a grip axis as tool members rotate in opposition to each other. Thus, the instrument 4400 provides for up to three degrees of freedom (i.e., a pitch motion about the first axis of rotation $A_1$, a yaw rotation about the second axis of rotation $A_2$, and a grip motion about the second axis of rotation $A_2$). The tool member 4462 can be rotatably coupled to the second link 4610 via any suitable joint. For example, in some embodiments, the second link 4610 can include a clevis and a pin, such as the pinned joints shown and described in U.S. Pat. No. 9,204,923 B2 (filed Jul. 16, 2008), entitled "Medical Instrument Electronically Energized Using Drive Cables," which is incorporated herein by reference in its entirety. In other embodiments, the second link 4610 can include a compliant mechanism, such as the compliant mechanisms shown and described in International Patent Publication No. WO 2016/123139 A2 (filed Jan. 26, 2016), entitled "Rolling-Contact Joint Mechanisms and Methods," which is incorporated herein by reference in its entirety.

As shown, the second link 4610 defines a guide channel 4615 within which a portion 4422 of the band 4420 is movably disposed. In some embodiments, the second link 4610 includes an inner guide surface and an outer guide surface (similar to the inner guide surface 3516 and the outer guide surface 3517, respectively) that each form a portion of the boundary of the guide channel 4615. Moreover, in some embodiments, the guide channel 4615 is curved along the longitudinal center line of the second link 4610. In this manner, when the second link 4610 rotates relative to the first link 4510 about the first axis of rotation $A_1$ (i.e., pitch motion), the band 4420 can contact the curved portions of the inner guide surface and the outer guide surface of the second link 4610 to maintain the desired bend geometry, band tension, and the like during actuation of the instrument 4400.

The tool member 4462 is coupled to the wrist assembly 4500 and includes a contact portion 4464 and a pulley portion 4467. The contact portion 4464 is configured engage or manipulate a target tissue during a surgical procedure. For example, in some embodiments, the contact portion 4464 can include an engagement surface that functions as a gripper, cutter, tissue manipulator, or the like. In other embodiments, the contact portion 4464 can be an energized tool member that is used for cauterization procedures. As described above, the pulley portion 4467 is rotatably coupled to the second link 4610 such that the tool member 4462 rotates relative to the wrist assembly 4500 about the second axis of rotation $A_2$, as shown by the arrow JJ. In this manner, the contact portion 4464 of the tool member 4462 can engage or manipulate a target tissue during a surgical procedure. The tool member 4462 (or any of the tool members described herein) can be any suitable medical tool member. Moreover, although only one tool member 4462 is shown, in other embodiments, the instrument 4400 includes two moving tool members that cooperatively perform gripping or shearing functions. In this manner, the tool member 4462 can form a portion of an end effector for the instrument 4400.

The band 4420 (which acts as a tension member) defines a longitudinal center line CL, and has a first band portion 4421, a second band portion 4422, and a third band portion 4423. The third band portion 4423 is between the second band portion 4422 and the first band portion 4421. The first band portion 4421 is within the guide channel 4615, and extends into the first link member 4510. In some embodiments, the band 4420 can include a fourth band portion (i.e., a proximal end portion) that extends outside of the wrist assembly 4500, through the shaft (not shown), and is coupled to an actuator (not shown). The actuator can move the band 4420 by any suitable mechanism to produce a resulting movement (or force) at the first band portion 4421 (as shown by arrow II in FIG. 18). The second band portion 4422 is coupled to the tool member 4462. Specifically, the second band portion 4422 is coupled to (or wrapped about a portion of) the pulley portion 4467 of the tool member 4462. In this manner, as described herein, movement of (or a force applied to) the band 4420 produces rotation of the tool member 4462 (as shown by the arrow JJ), rotation of the second link 4610, or rotation of both the tool member 4462 and the second link 4610. The second band portion 4422 of the band 4420 can be coupled to the tool member 4462 by any suitable mechanism. For example, in some embodiments, the second band portion 4422 can be coupled to the tool member 4462 by a pin or protrusion that engages (or is received within) a connection portion of the pulley portion 4467. In other embodiments, the second band portion 4422 can be coupled to the pulley portion 4467 via an adhesive.

As shown, the band 4420 is twisted along its longitudinal center line CL between the first band portion 4421 and the second band portion 4422. Similarly stated, referring to FIGS. 19-21, the band 4420 is angularly deformed along its longitudinal center line CL such that the orientation of a contact surface 4425 at the first band portion 4421 is different than an orientation of the contact surface 4425 at the second band portion 4422. As shown in FIG. 20, both the orientation and the shape of the contact surface 4425 is different at the third band portion 4423 than at the first band portion 4421 or the second band portion 4422. As yet another way to describe the twist of the band 4420, the cross-sectional shape of the band 4420 within a plane normal to the longitudinal center line CL is characterized by a major axis. Although the term major axis is often used in the context of an elliptical shape, as used herein in the context of rectangular (or trapezoidal) shape, the term "major axis" is the longer axis of the cross-sectional shape that passes through the center point of opposing sides. Referring to FIGS. 19-21, the major axis AM1 within the first band portion 4421 is at a different angular orientation than the major axis AM2 within the second band portion 4422. In this manner, the contact surface 4425 at the first band portion 4421 can be in contact with a guide surface or can be curved about the first axis of rotation $A_1$, and the contact surface 4425 at the second band portion 4422 can be wrapped about the pulley portion 4467 or curved about the second axis of rotation $A_2$. By being twisted, the area moment of inertia of the band 4420 about the desired axis of deformation is minimized Thus, the flexibility of the band 4420 is maximized at both the first band portion 4421 (to facilitate rotation of the second link member 4610 about the pitch axis $A_1$) and the second band portion 4422 (to facilitate rotation of the tool member 4462 about the yaw axis $A_2$).

Referring to FIG. 21, the band 4420 can be twisted by any suitable twist angle Θ along its longitudinal center line CL between the first band portion 4421 and the second band portion 4422. In some embodiments, the twist angle Θ can be the same as the angle defined between the first axis of rotation $A_1$ and the second axis of rotation $A_2$ (referred to as the "rotation offset angle"). In some embodiments, the twist angle Θ can be approximately 90 degrees.

The band 4420 (and any of the bands described herein) can have any suitable shape. Moreover, the band 4420 (and any of the bands described herein) can be constructed from any suitable materials. For example, in some embodiments, the band 4420 (and any of the bands described herein) can be constructed from a series of laminates that are bonded together (e.g., via an adhesive). In other embodiments, the laminates can be joined by any other suitable method. The laminates can be constructed from any suitable material, including tungsten, steel, or any suitable polymer.

The use of the band 4420 can provide for a low-cost, disposable instrument that is suitable for surgical procedures. In use, the distal end portion of the instrument 4400 provides for up to three degrees of freedom, and can be moved between multiple different configurations to perform a variety of surgical operations. For example, in some situations, the second link 4610 can be rotated about the pitch axis $A_1$, thereby bending or curving the band 4420 about an axis parallel to the major axis AM1 within the first band portion 4421. In other situations, the tool member 4462 can be rotated about the yaw axis $A_2$, thereby bending or curving the band 4420 about an axis parallel to the major axis AM2 within the second band portion 4422.

Figure 22:
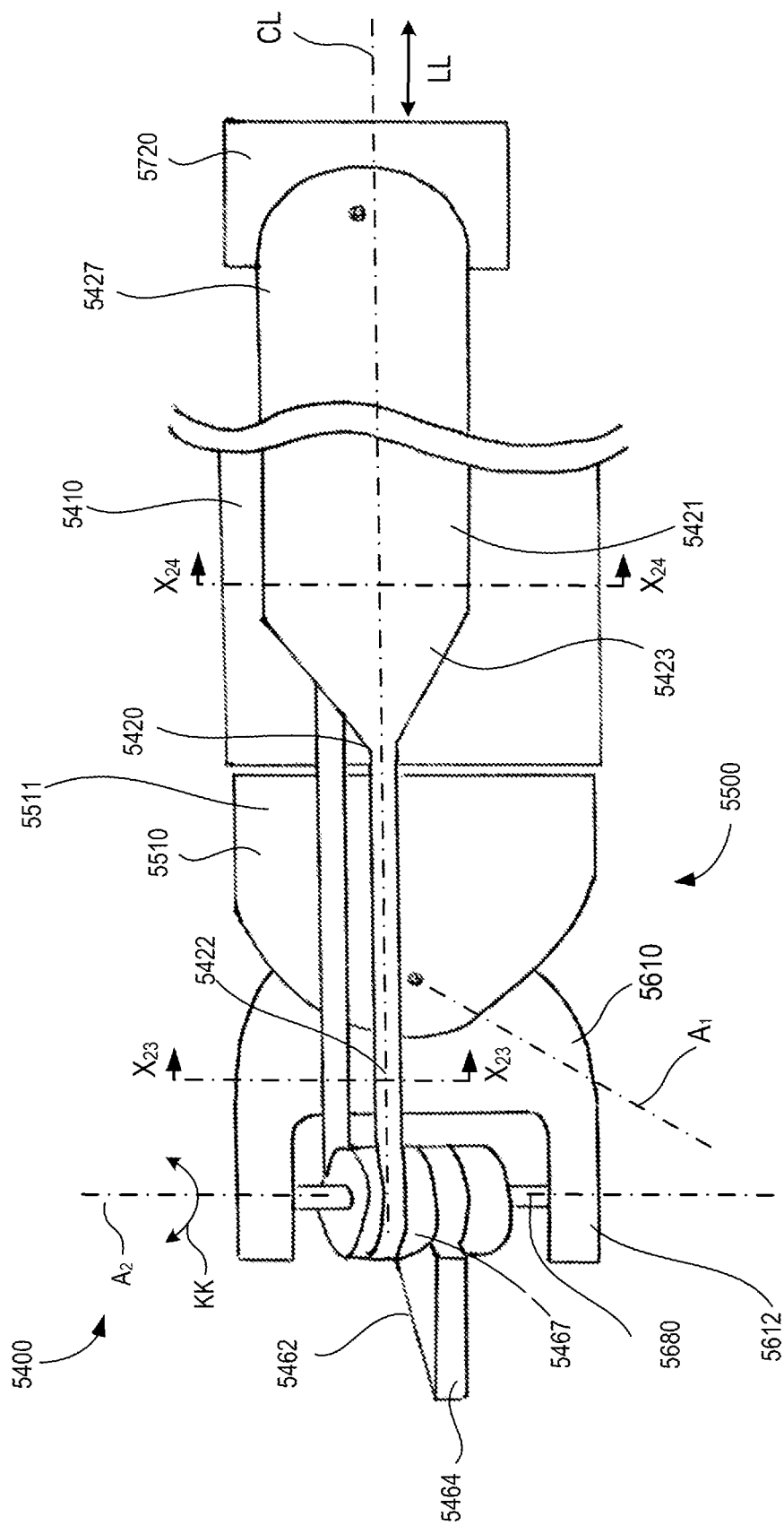
FIG. 22 is a diagrammatic illustration of a portion of an instrument of a surgery system, according to an embodiment.
Figure 23:
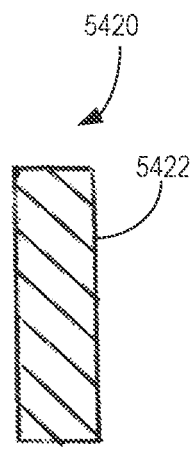
FIGS. 23-24 are diagrammatic side cross-sectional views of a band included within the instrument shown in FIG. 22, taken along the lines $X_{23}$-$X_{23}$ (FIG. 23) and $X_{24}$-$X_{24}$ (FIG. 24).
Figure 24:
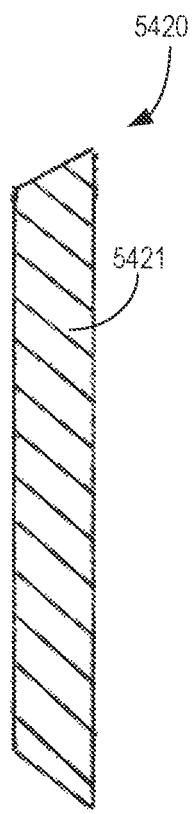

Although the bands described above (e.g., the band 4420) are shown as having a constant cross-sectional area along the longitudinal center line of the band, in other embodiments, any of the bands shown and described herein can have a variable cross-sectional area, shape, or size. For example, in some embodiments, an instrument can include one or more bands having a smaller cross-sectional area in regions within the wrist (or where the band is coupled to the end effector) and a larger cross-sectional area within the shaft (or at the actuator). In this manner, the portions of the band having the larger cross-sectional area can have a greater strength, which can, in turn, minimize the amount of band stretch (deformation) during use. For example, FIG. 22 is a diagrammatic illustration of a portion of an instrument 5400, according to an embodiment. The instrument 5400 includes a wrist assembly 5500, a band 5420, and a tool member 5462. FIGS. 23 and 24 are cross-sectional views of the band 5420 taken within a plane normal to the longitudinal center line CL of the band 5420. The instrument 5400 is configured such that movement of the band 5420 produces movement of the wrist assembly 5500 about the pitch axis $A_1$, movement of the tool member 5462 about the yaw axis $A_2$, or both movement of the wrist assembly 5500 and movement of the tool member 5462.

The wrist assembly 5500 (also referred to as a joint assembly) includes a proximal first link 5510 and a distal second link 5610. The first link 5510 has a proximal end portion 5511 that is coupled to a shaft 5410. The shaft 5410 can be any suitable elongated shaft that couples the wrist assembly 5500 to the actuator 5700. For example, in some embodiments, the shaft 5410 can be a cylindrical shaft within which the band 5420 and other components routed from the actuator 5700 to the wrist assembly 5500 are disposed (e.g., electrical wires, ground wires, or the like). The proximal end portion 5511 can be coupled to the shaft 5410 via any suitable mechanism. For example, in some embodiments, the proximal end portion 5511 can be matingly disposed within a portion of the shaft 5410 (e.g., via an interference fit). In some embodiments, the proximal end portion 5511 can include one or more protrusions, recesses, openings, or connectors that couple the proximal end portion 5511 to the shaft 5410.

The second link 5610 has a proximal end portion and a distal end portion 5612. The proximal end portion is rotatably coupled to the first link 5510 to form the wrist assembly 5500 having a first axis of rotation $A_1$ (which functions as the pitch axis, the term pitch is arbitrary) about which the second link 5610 rotates relative to the first link. The wrist assembly 5500 can include any suitable coupling mechanism. For example, in some embodiments, the second link 5610 can be coupled to the first link 5510 via a pinned joint of the types shown and described herein. In other embodiments, the second link 5610 can be coupled to the first link 5510 via mating disc surfaces of the types shown and described herein.

The distal end portion 5612 of the second link 5610 includes a connector 5680 that is coupled to a pulley portion 5467 of the tool member 5462 such that the tool member 5462 rotates relative to the wrist assembly 5500 about a second axis of rotation $A_2$. The second axis of rotation $A_2$ is non-parallel to the first axis of rotation $A_1$. The axis $A_2$ functions both as a yaw axis (the term yaw is arbitrary) as tool members rotate together and as a grip axis as tool members rotate in opposition to each other. Thus, the instrument 5400 provides for up to three degrees of freedom (i.e., a pitch motion about the first axis of rotation $A_1$, a yaw rotation about the second axis of rotation $A_2$, and a grip motion about the second axis of rotation $A_2$). The connector 5680 can be any suitable connector to rotatably couple the tool member 5462 to the wrist assembly 5500. For example, in some embodiments, the second link 5610 can include a clevis and a pin, such as the pinned joints shown and described in U.S. Pat. No. 9,204,923 B2 (filed Jul. 16, 2008), entitled "Medical Instrument Electronically Energized Using Drive Cables," which is incorporated herein by reference in its entirety. In other embodiments, the second link 5610 can include a compliant mechanism, such as the compliant mechanisms shown and described in International Patent Publication No. WO 2016/123139 A2 (filed Jan. 26, 2016), entitled "Rolling-Contact Joint Mechanisms and Methods," which is incorporated herein by reference in its entirety.

The tool member 5462 is coupled to the wrist assembly 5500 and includes a contact portion 5464 and a pulley portion 5467. The contact portion 5464 is configured to engage or manipulate a target tissue during a surgical procedure. For example, in some embodiments, the contact portion 5464 can include an engagement surface that functions as a gripper, cutter, tissue manipulator, or the like. In other embodiments, the contact portion 5464 can be an energized tool member that is used for cauterization procedures. As described above, the pulley portion 5467 is rotatably coupled to the second link 5610 such that the tool member 5462 rotates relative to the wrist assembly 5500 via the second axis of rotation $A_2$, as shown by the arrow KK. In this manner, the contact portion 5464 of the tool member 5462 can engage or manipulate a target tissue during a surgical procedure. The tool member 5462 (or any of the tool members described herein) can be any suitable medical tool member. Moreover, although only one tool member 5462 is shown, in other embodiments, the instrument 5400 includes two moving tool members that cooperatively perform gripping or shearing functions. In this manner, the tool member 5462 can form a portion of an end effector for the instrument 5400.

The band 5420 (which acts as a tension member) defines a longitudinal center line CL, and has a first band portion 5421, a second band portion 5422, a third band portion 5423, a fourth band portion 5431 and a fifth (or proximal-most) band portion 5427. The first band portion 5421 is disposed within the shaft 5410 and, as shown in FIG. 24, has a first cross-sectional area in a first plane normal to the longitudinal center line CL. The second band portion 5422 is coupled to the tool member 5462. As shown in FIG. 23, the second band portion 5422 has a second cross-sectional area in a second plane normal to the longitudinal center line CL. Specifically, the second cross-sectional area is less than the first cross-sectional area. In this manner, the band 5420 can have a larger (and therefore higher strength) portion within the shaft 5410 and a smaller, more flexible portion within the wrist assembly 5500 (and being coupled to the tool member 5462). The third band portion 5423 is between the second band portion 5422 and the first band portion 5421, and is a transition portion between the smaller second band portion 5422 and the larger first band portion 5421. Although the third band portion 5423 is shown as transitioning between the first band portion 5421 and the second band portion 5422 symmetrically about the longitudinal center line CL, in other embodiments, the third band portion 5423 can transition (or taper) asymmetrically along the longitudinal center line CL. Moreover, although the third band portion 5423 is shown as transitioning continuously and linearly between the first band portion 5421 and the second band portion 5422, in other embodiments, the third band portion 5423 can transition (or taper) discontinuously or non-linearly along the longitudinal center line CL.

As shown, the second band portion 5422 is wrapped about the pulley portion 5467 of the tool member 5462. In this manner, the fourth band portion 5431 extends into the shaft 5410 and is opposite the first band portion 5421. In some embodiments, the band is monolithically constructed such that the first band portion 5421, the second band portion 5422, the third band portion 5423 and the fourth band portion 5431 are all within a single element. In other embodiments, however, the fourth band portion 5431 can be constructed separately from (or can be a different element as) the first band portion 5421. The second band portion 5422 can be coupled to the tool member 5462 by any suitable mechanism. For example, in some embodiments, the second band portion 5422 can be coupled to the tool member 5462 by a pin or protrusion that engages (or is received within) a connection portion of the pulley portion 5467. In other embodiments, the second band portion 5422 can be coupled to the pulley portion 5467 via an adhesive.

The fifth (or proximal-most) band portion 5427 is coupled to an actuator 5700. The actuator can be a motor-driven actuator that produces movement of the fifth band portion 5427, as shown by the arrow KK. The band movement at the fifth band portion 5427 produces rotation of the tool member 5462 (as shown by the arrow KK), rotation of the second link 5610, or rotation of both the tool member 5462 and the second link 5610. By increasing the cross-sectional area of the first band portion 5421, the stiffness or rigidity of the band 5420 within the shaft 5410 is increased, thereby increasing the conservation of motion of the band 5420 between the proximal-most band portion 5427 and the distal-most (or second) band portion 5422.

As shown, the actuator 5700 can include a linear actuator that translates relative to the shaft 5410 to move the fifth band portion 5427. In other embodiments, however, the actuator 5700 can include a capstan or other motor-driven roller that rotates or "winds" the fifth band portion 5427 to produce movement. For example, in some embodiments, the actuator 5700 can include any of the backend assemblies or components described in U.S. Pat. No. 9,204,923 B2 (filed Jul. 16, 2008), entitled "Medical Instrument Electronically Energized Using Drive Cables," which is incorporated herein by reference in its entirety.

The band 5420 (and any of the bands described herein) can have any suitable shape. For example, in some embodiments, the shape of the first band portion 5421 can be trapezoidal (see FIG. 24) and the shape of the second band portion 5422 can be rectangular. Moreover, the band 5420 (and any of the bands described herein) can be constructed from any suitable materials. For example, in some embodiments, the band 5420 (and any of the bands described herein) can be constructed from a series of laminates that are bonded together (e.g., via an adhesive). In other embodiments, the laminates can be joined by any other suitable method. The laminates can be constructed from any suitable material, including tungsten, steel, or any suitable polymer.

Figure 25:
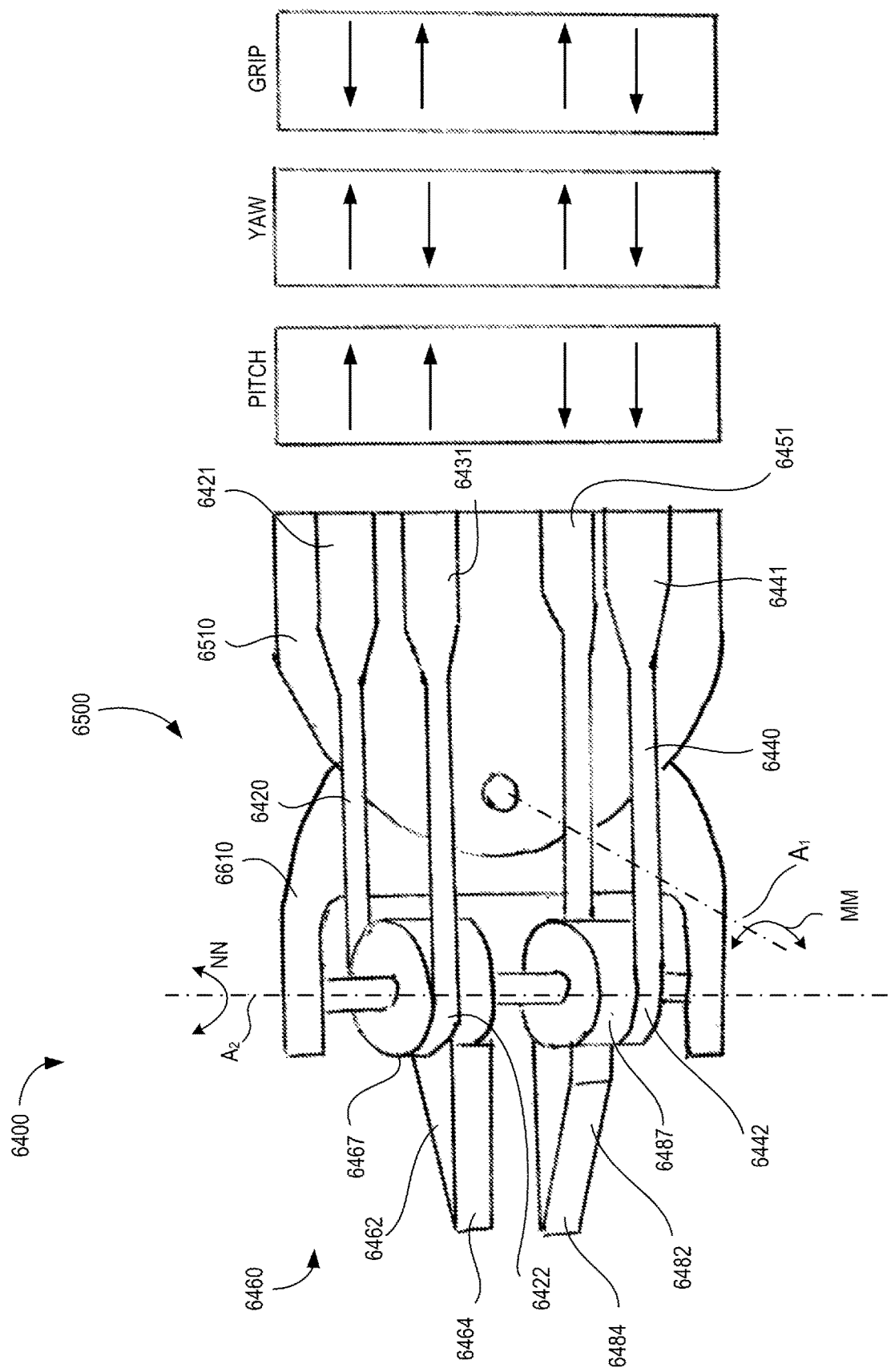
FIG. 25 is a diagrammatic illustration of a portion of an instrument of a surgery system, according to an embodiment.
Figure 26:
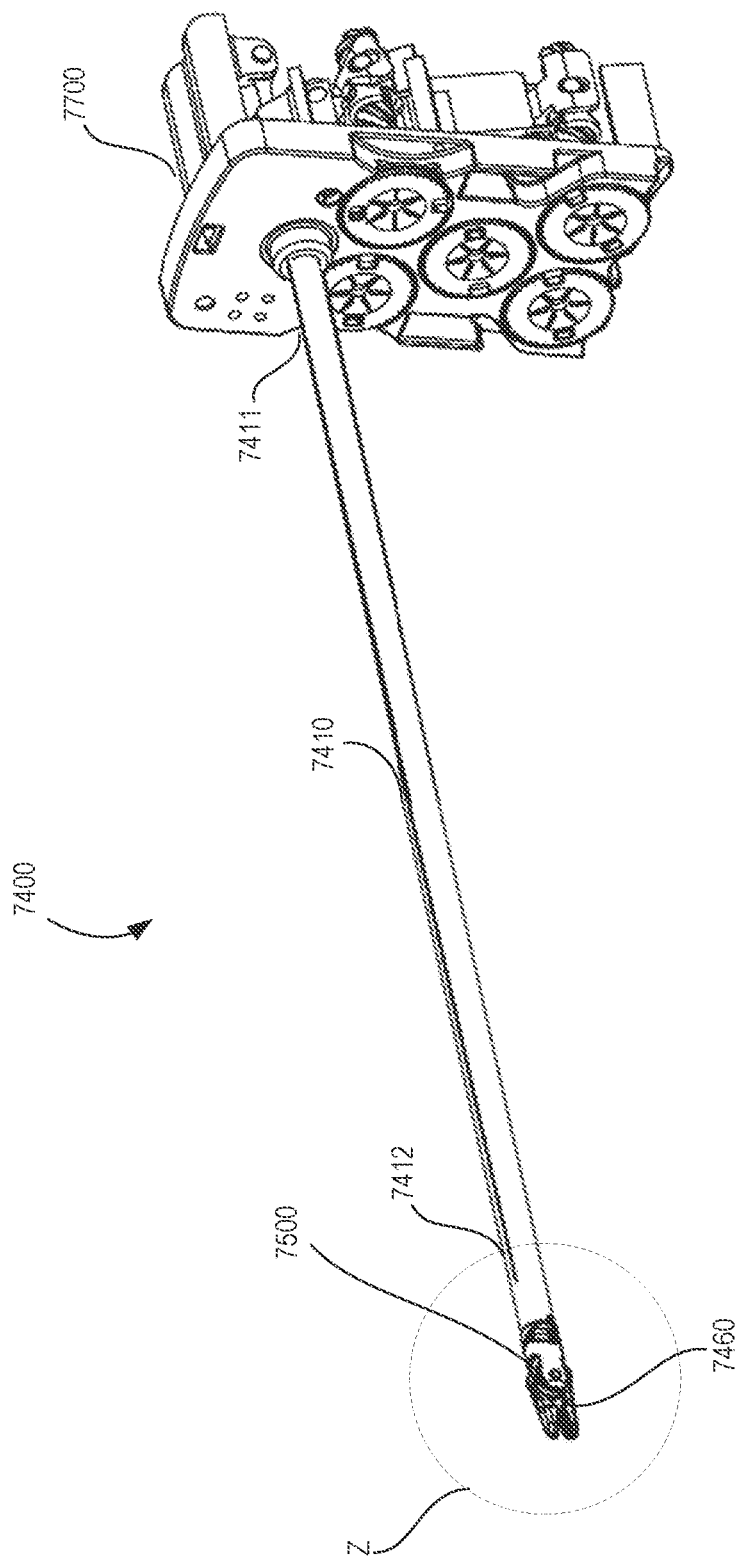
FIG. 26 is a perspective view of an instrument of a surgery system in a first configuration, according to an embodiment.

Although the instruments shown above (e.g., the instrument 4400 and the instrument 5400) include a single tool member, in other embodiments, an instrument can include any suitable number of tool members (e.g., to form the desired end effector). Moreover, although the instruments are shown above as including a single band either with a single connection point to a tool member (e.g., the instrument 2400) or wrapped about a pulley portion of a tool member (e.g., the instrument 5400) in other embodiments, an instrument can include any suitable number of bands to actuate the wrist assembly and end effector. For example, FIG. 25 is a diagrammatic illustration of a portion of an instrument 6400, according to an embodiment. The instrument 6400 includes a wrist assembly 6500, a first band 6420, a second band 6440, and an end effector 6460. The instrument 6400 is configured such that movement of various portions of the first band 6420 and the second band 6440 produces movement of the wrist assembly 6500 about the pitch axis $A_1$, movement of the end effector 6460 about the yaw axis $A_2$, gripping motion of the end effector 6460, or any combination of these motions.

The wrist assembly 6500 includes a proximal first link 6510 and a distal second link 6610. The first link 6510 is coupled to a shaft (not shown) of the types shown and described herein. The second link 6610 has a proximal end portion and a distal end portion. The proximal end portion is rotatably coupled to the first link 6510 to form the wrist assembly 6500 having a first axis of rotation $A_1$ (which functions as the pitch axis, the term pitch is arbitrary) about which the second link 6610 rotates relative to the first link 6510. The wrist assembly 6500 can include any suitable coupling mechanism. For example, in some embodiments, the second link 6610 can be coupled to the first link 6510 via a pinned joint of the types shown and described herein. In other embodiments, the second link 6610 can be coupled to the first link 6510 via mating disc surfaces of the types shown and described herein.

The distal end portion of the second link 6610 is coupled to the end effector 6460. More specifically, the distal end portion of the second link 6610 is coupled to a pulley portion 6467 of a first tool member 6462 and a pulley portion 6487 of a second tool member 6482. This arrangement allows each of the tool member 6462 and the tool member 6482 to rotate relative to the wrist assembly 6500 about a second axis of rotation $A_2$. The second axis of rotation $A_2$ is non-parallel to the first axis of rotation $A_1$ and functions both as a yaw axis (the term yaw is arbitrary) as tool members rotate together and as a grip axis as tool members rotate in opposition to each other. Thus, the instrument 6400 provides for up to three degrees of freedom (i.e., a pitch motion about the first axis of rotation $A_1$, a yaw rotation about the second axis of rotation $A_2$, and a grip motion about the second axis of rotation $A_2$). Although the end effector 6460 is shown as being coupled to the second link 6610 via a pin connector, in other embodiments, the end effector 6460 can be coupled to the wrist assembly 6500 by any suitable mechanism.

The end effector includes the first tool member 6462 and the second tool member 6482. The first tool member 6462 includes a contact portion 6464 and a pulley portion 6467, and the second tool member 6482 includes a contact portion 6484 and a pulley portion 6487. The contact portion 6464 and the contact portion 6484 are each configured to engage or manipulate a target tissue during a surgical procedure. For example, in some embodiments, the contact portions can include an engagement surfaces that function as a gripper, cutter, tissue manipulator, or the like. In other embodiments, the contact portions can be an energized tool member that is used for cauterization procedures. As described above, the pulley portion 6467 and the pulley portion 6487 are each rotatably coupled to the second link 6610 such that the tool member 6462 rotates relative to the wrist assembly 6500 about the second axis of rotation $A_2$. The pulley portions can include a contact surface about which the corresponding bands (i.e., the first band 6420 and the second band 6440) are wrapped. The first tool member 6462 and the second tool member 6482 (or any of the tool members described herein) can be any suitable medical tool member.

The first band 6420 (which acts as a tension member) has a first proximal end portion 6421, a second proximal end portion 6431, and a distal end portion 6422. As shown, the distal end portion 6422 is wrapped about the pulley portion 6467 of the first tool member 6462. In this manner, the first proximal end portion 6421 and the second proximal end portion 6431 each extend through the first link 6510 and into the shaft (not shown). Additionally, the first proximal end portion 6421 and the second proximal end portion 6431 are each coupled to an actuator (not shown, but similar to the actuator 5700 described above) that can move each of the proximal end portions (as shown by the series of arrows labeled as PITCH, YAW, and GRIP). The second band 6440 (which also acts as a tension member) has a third proximal end portion 6441, a fourth proximal end portion 6451, and a distal end portion 6442. As shown, the distal end portion 6442 is wrapped about the pulley portion 6487 of the second tool member 6482. In this manner, the third proximal end portion 6441 and the fourth proximal end portion 6451 each extend through the first link 6510 and into the shaft (not shown). Additionally, the third proximal end portion 6441 and the fourth proximal end portion 6451 are each coupled to an actuator (not shown, but similar to the actuator 5700 described above) that can move each of the proximal end portions (as shown by the series of arrows labeled as PITCH, YAW, and GRIP).

In some embodiments, the first band 6420 or the second band 6440 (or both) can be monolithically constructed such that the first proximal end portion, the second proximal end portion, and the distal end portion are all within a single element. In other embodiments, however, the first band 6420 or the second band 6440 (or both) can include multiple separately constructed components (e.g., the first proximal end portion 6421 can be separately constructed from the second proximal end portion 6431). Moreover, the first band 6420 or the second band 6440 (or both) can have any suitable shape as described herein. In some embodiments, the first band 6420 or the second band 6440 (or both) can have varying cross-sectional areas (as described above with reference to the band 5420) or can be twisted along its longitudinal center line (as described above with reference to the band 4420). In some embodiments, the first band 6420 or the second band 6440 (or both) can be constructed from a series of laminates that are bonded together (e.g., via an adhesive). In other embodiments, the laminates can be joined by any other suitable method. The laminates can be constructed from any suitable material, including tungsten, steel, or any suitable polymer.

Changing the pitch, yaw, or grip of the instrument 6400 generally requires movements or actions respectively applied to each of the four proximal end portions (the first proximal end portion 6421, the second proximal end portion, the third proximal end portion 6441, and the fourth proximal end portion 6451). The movement of the band portions can generally be performed one at a time or simultaneously in any desired combination to change the pitch, yaw, and grip of instrument 6400. For example, pitch axis rotations rotate the second link 6610 about the first axis of rotation $A_1$ (pitch axis), as shown by the arrow MM. For clockwise rotation about the pitch axis $A_1$, the actuators (not shown) pull in (i.e., move proximally) identical lengths of the first proximal end portion 6421 and the second proximal end portion 6431 while releasing (i.e., allowing to move distally) the same lengths of the third proximal end portion 6441 and the fourth proximal end portion 6451. This is illustrated by the arrows labeled as PITCH. The first proximal end portion 6421 and the second proximal end portion 6431 apply forces to the second link 6610 at moment arms defined by the guide channels through the wrist assembly 6500. Similarly stated, the first link 6510 and the second link 6610 can define one or more guide channels that are offset from the pitch axis $A_1$ to produce a torque about the pitch axis $A_1$. The guide channels can be any of the guide channels described herein (e.g., the guide channels shown and described in connection with the wrist assembly 2500 or the wrist assembly 3500). Similarly, for counterclockwise rotation of the second link 6610 about the pitch axis $A_1$, the actuators pull in (i.e., move proximally) identical lengths of the third proximal end portion 6441 and the fourth proximal end portion 6451 while releasing (i.e., allowing to move distally) the same lengths of the first proximal end portion 6421 and the second proximal end portion 6431.

Yaw rotations are the rotation of the first tool member 6462 and the second tool member 6482 about the second axis of rotation $A_2$ (yaw axis) in the same direction and through the same angle. In particular, when the actuators pull in (i.e., move proximally) a length of the first proximal end portion 6421 and release (i.e., allow to move distally) an equal length of the second proximal end portion 6431, the first tool member 6462 will rotate in a clockwise direction about the yaw axis $A_2$ (see the arrow NN). For this rotation, the guide channel or pulley surface of the pulley portion 6467 defines the moment arm at which force transmitted via the first band 6420 is applied. The resulting torque causes the first tool member 6462 to rotate clockwise. During this movement, the first proximal end portion 6421 and the second proximal end portion 6431 each slide within the guide channels of the second link 6610. If, at the same time, the actuators pull in a length of the fourth proximal end portion 6451 and release the same length of the third proximal end portion 6441, the second tool member 6482 will rotate clockwise through an angle that is the same as the angle through which the first tool member 6462 rotates. Accordingly, the first tool member 6462 and the second tool member 6482 maintain their positions relative to each other and rotate as a unit through a yaw angle. Counterclockwise rotation of the end effector 6460 is similarly accomplished when the actuators pull in equal lengths of the second proximal end portion 6431 and the third proximal end portion 6441 while releasing the same lengths of the first proximal end portion 6421 and the fourth proximal end portion 6451. This is illustrated by the arrows labeled as YAW.

Grip rotations are rotations of the first tool member 6462 and the second tool member 6482 about the yaw axis $A_2$ in opposite directions and through the same angle. To open the grip of the end effector 6460, the actuators pull in equal lengths of the first proximal end portion 6421 and the third proximal end portion 6441 while releasing the same lengths of the second proximal end portion 6431 and the fourth proximal end portion 6451. This causes the first tool member 6562 to rotate in an opposite direction from the second tool member 6482. To close the grip of the end effector, the actuators pull in equal lengths of the second proximal end portion 6431 and the fourth proximal end portion 6451 while releasing the same lengths of the first proximal end portion 6421 and the third proximal end portion 6441. This causes the first tool member 6562 to rotate towards the second tool member 6482. When contact portion of the tool members come into contact, the tension in the second proximal end portion 6431 and the fourth proximal end portion 6451 can be kept greater than the tension in the first proximal end portion 6421 and the third proximal end portion 6441 to maintain the desired gripping forces.

FIGS. 26-36 are various views of an instrument 7400, according to an embodiment. In some embodiments, the instrument 7400 or any of the components therein are optionally parts of a surgical system that performs surgical procedures, and which can include a manipulator unit, a series of kinematic linkages, a series of cannulas, or the like. The instrument 7400 (and any of the instruments described herein) can be used in any suitable surgical system, such as the MIRS system 1000 shown and described above. The instrument 7400 includes an actuator assembly 7700, a shaft 7410, a wrist assembly 7500, and an end effector 7460. Referring to FIG. 29, the instrument 7400 also includes a series of bands (specifically, a first band 7420, a second band 7430, a third band 7440, and a fourth band 7450) that couple the backend mechanism 7700 to the wrist assembly 7500. The instrument 7400 is configured such that movement of the bands produces rotation of the wrist assembly 7500 (i.e., pitch rotation) about a first axis of rotation $A_1$ (see FIG. 27, which functions as the pitch axis, the term pitch is arbitrary), yaw rotation of the end effector 7460 about a second axis of rotation $A_2$ (see FIGS. 27 and 28, which functions as the yaw axis), grip rotation of the tool members of the end effector 7460 about the second axis of rotation $A_2$, or any combination of these movements. Changing the pitch, yaw, or grip of the instrument 7400 can be performed by manipulating the four bands in similar manner as that described above for the instrument 6400. Thus, the specific movement of each of the four bands to accomplish the desired motion is not described below.

The backend mechanism 7700 produces movement of each of the first band 7420, the second band 7430, the third band 7440, and the fourth band 7450 to produce the desired movement (pitch, yaw, or grip) at the wrist assembly 7500. Specifically, the backend mechanism 7700 includes components and controls to move some of the bands in a proximal direction (i.e., to pull in certain bands) while simultaneously allowing the distal movement (i.e., releasing or "paying out") of other of the bands in equal lengths. In this manner, the backend mechanism 7700 can maintain the desired tension within the bands, and in some embodiments, can ensure that the lengths of the bands are conserved (i.e., moved in equal amounts) during the entire range of motion of the wrist assembly 7500. In other embodiments, however, conservation of the lengths of the bands is not required.

In some embodiments, the backend mechanism 7700 can include one or more linear actuators that produce translation (linear motion) of a portion of the bands. Such backend mechanisms can include, for example, a gimbal, a lever, or any other suitable mechanism to directly pull (or release) an end portion of any of the bands. For example, in some embodiments, the backend mechanism 7700 can include any of the backend assemblies or components described in U.S. Patent Application Pub. No. US 20157/0047454 A1 (filed Aug. 15, 2014), entitled "Lever Actuated Gimbal Plate," or U.S. Pat. No. 6,817,974 B2 (filed Jun. 28, 2001), entitled "Surgical Tool Having Positively Positionable Tendon-Actuated Multi-Disk Wrist Joint," each of which is incorporated herein by reference in its entirety. In other embodiments, however, the backend mechanism 7700 can include a capstan or other motor-driven roller that rotates or "winds" a portion of any of the bands to produce the desired band movement. For example, in some embodiments, the backend mechanism 7700 can include any of the backend assemblies or components described in U.S. Pat. No. 9,204,923 B2 (filed Jul. 16, 2008), entitled "Medical Instrument Electronically Energized Using Drive Cables," which is incorporated herein by reference in its entirety.

The shaft 7410 can be any suitable elongated shaft that couples the wrist assembly 7500 to the backend mechanism 7700. Specifically, the shaft 7410 includes a proximal end portion 7411 that is coupled to a housing of the backend mechanism 7700, and a distal end portion 7412 that is coupled to the wrist assembly 7500. The shaft 7410 defines a passageway or series of passageways through which the bands and other components (e.g., electrical wires, ground wires, or the like) can be routed from the backend mechanism 7700 to the wrist assembly 7500. Although shown as being cylindrical, in other embodiments, the shaft 7410 can have any suitable shape.

Figure 27:
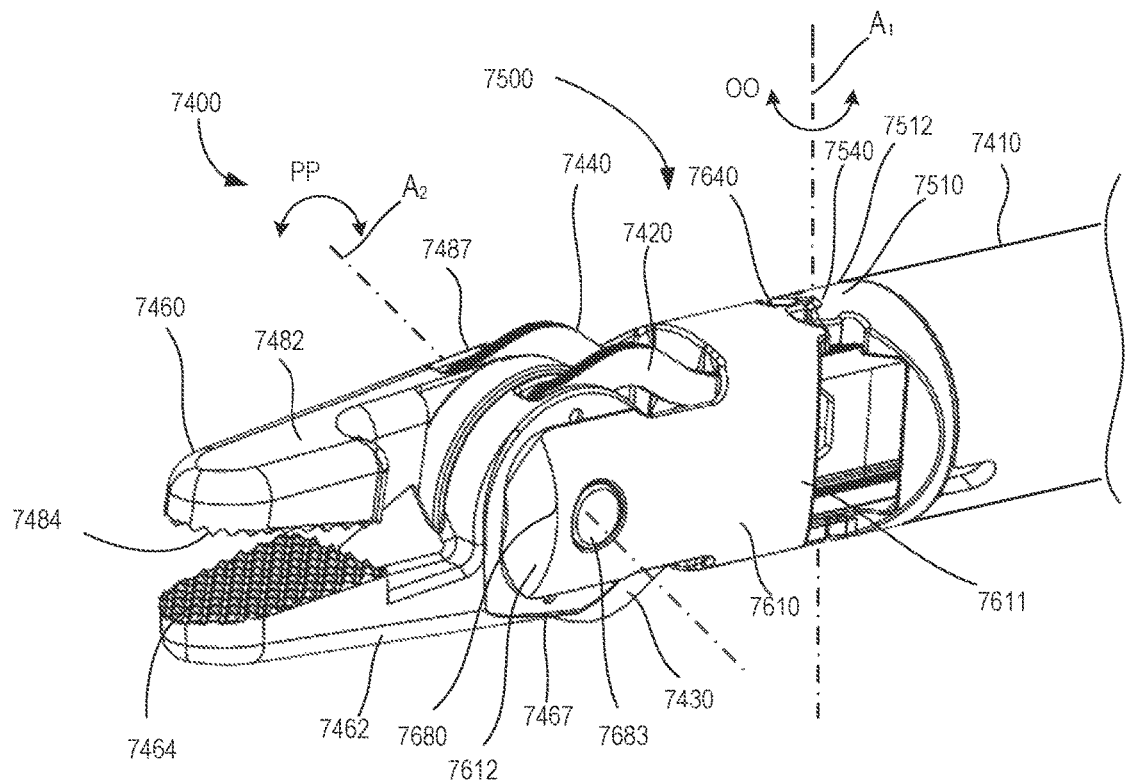
FIG. 27 is an enlarged perspective view of a distal end portion of the instrument indicated by the region Z shown in FIG. 26.
Figure 28:
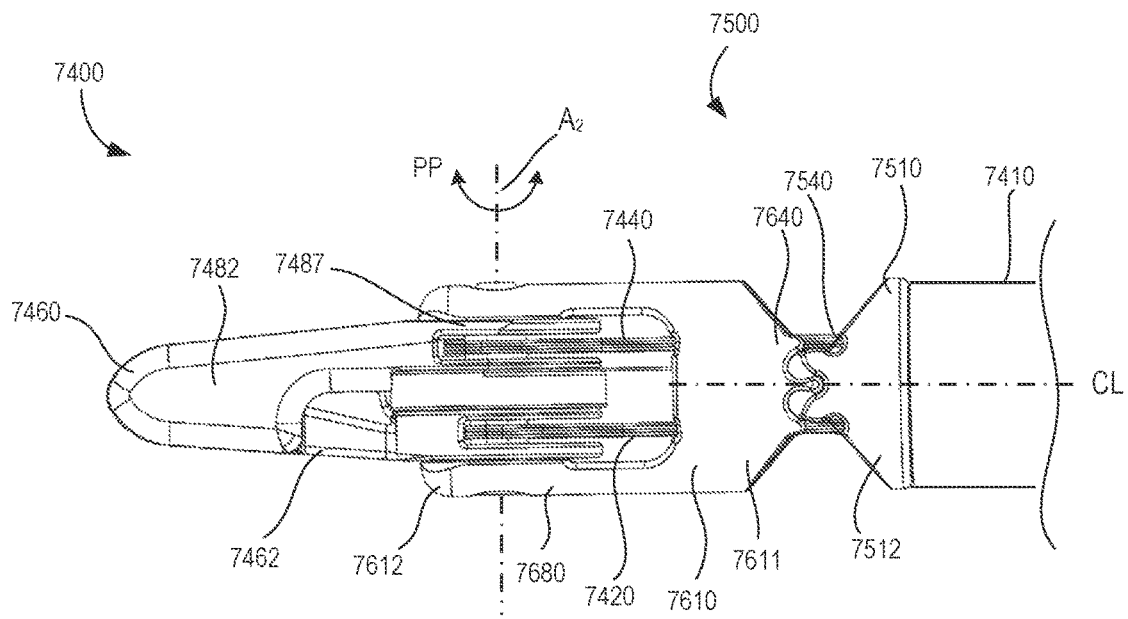
FIG. 28 is a top view.

Referring to FIGS. 27 and 28, the wrist assembly 7500 includes a proximal first link 7510 and a distal second link 7610. The first link 7510 has a proximal end portion 7511 and a distal end portion 7512. The proximal end portion 7511 is coupled to the distal end portion 7412 of the shaft 7410. The proximal end portion 7511 can be coupled to the shaft 7410 via any suitable mechanism. For example, in some embodiments, the proximal end portion 7511 can be matingly disposed within a portion of the shaft (e.g., via an interference fit). As shown, the proximal end portion 7511 can include one or more protrusions, recesses, openings, or connectors that couple the proximal end portion 7511 to the shaft. The proximal end portion 7511 can be fixedly coupled to the shaft 7410 via an adhesive bond, a weld, or any other permanent coupling mechanism (i.e., a coupling mechanism that is not intended to be removed during normal use).

The distal end portion 7512 includes a joint portion 7540 that is rotatably coupled to a mating joint portion 7640 of the second link 7610. In this manner, the first link 7510 and the second link 7610 form the wrist assembly 7500 having a first axis of rotation $A_1$ (which functions as the pitch axis, the term pitch is arbitrary) about which the second link 7610 rotates relative to the first link 7510. Specifically, the joint portion 7540 includes a series of teeth 7544 that are spaced apart by recesses. Because the wrist joint is not a pinned joint, the pitch axis $A_1$ will move relative to the first link 7510 during rotation of the second link 7610. The series of teeth 7544 and recesses can be similar to those shown and described in U.S. Patent Application Pub. No. US 2017/0120457 A1 (filed Feb. 20, 2015), entitled "Mechanical Wrist Joints with Enhanced Range of Motion, and Related Devices and Methods," which is incorporated herein by reference in its entirety.

Figure 31:
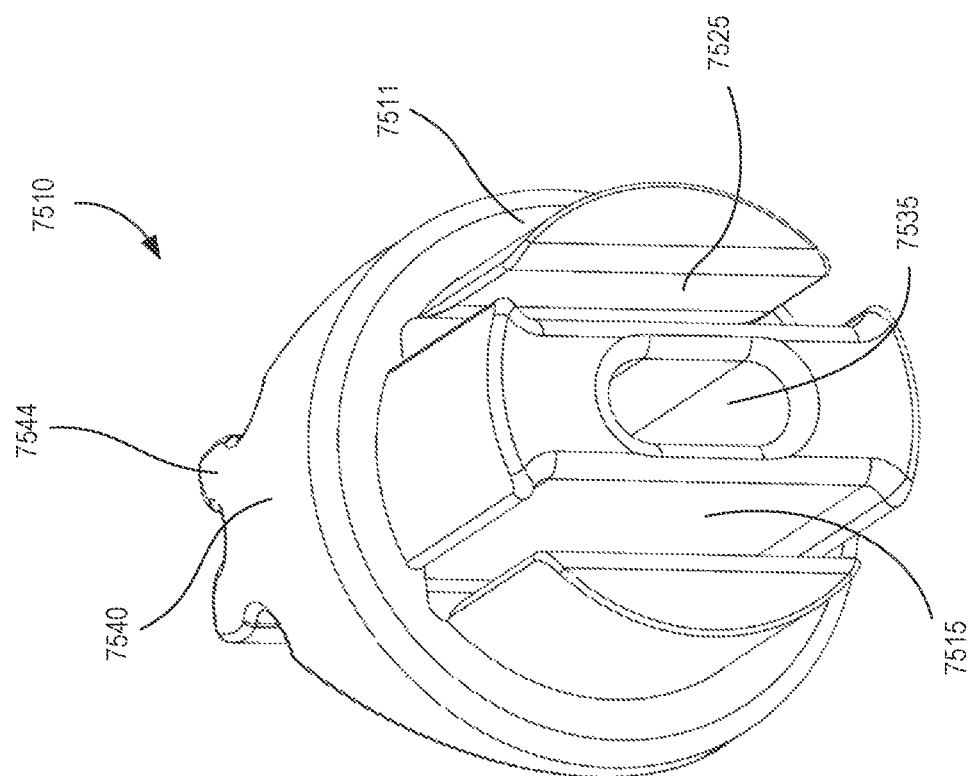
FIG. 31 is a right side perspective view of a first link of a wrist assembly of the instrument shown in FIG. 27.
Figure 30:
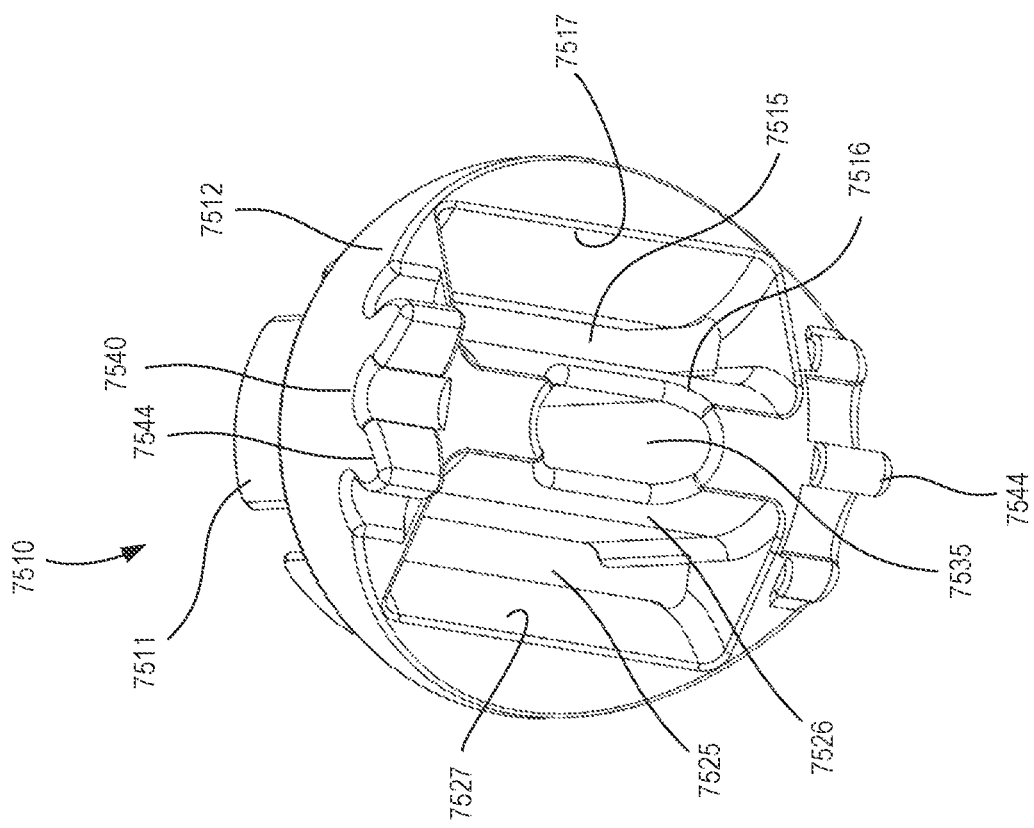
FIG. 30 is a left side perspective view.

Referring to FIGS. 30 and 31, a first guide channel 7515, a second guide channel 7525, and a central bore 7535 are defined in the first link 7510. The central bore 7535 can contain (or allow passage of) various components of the wrist assembly, such as, for example, electrical wires. The first link 7510 includes an inner guide surface 7516 and an outer guide surface 7517 that each form a portion of the boundary of the first guide channel 7515, and an inner guide surface 7526 and an outer guide surface 7527 that each form a portion of the boundary of the second guide channel 7525. The first band 7420 and the second band 7430 are movably disposed within the first guide channel 7515. The third band 7440 and the fourth band 7450 are movably disposed within the second guide channel 7525. Thus, each of the first guide channel 7515 and the second guide channel 7525 contain two bands.

As shown in FIG. 28, the first link 7510 and the second link 7610 define a longitudinal center line CL that intersects the pitch axis $A_1$ when the instrument is in an initial (or "straight" configuration). As noted above, when the second link 7610 rotates about the pitch axis $A_1$, the rolling interface between the joint portion 7540 and the joint portion 7640 is such that the pitch axis $A_1$ will move slightly and no longer be aligned with the longitudinal center line CL. As shown in FIGS. 30 and 31, at least a portion of the inner guide surface 7516 and at least a portion of the outer guide surface 7517 is curved along the longitudinal center line CL. Similarly, at least a portion of the inner guide surface 7526 and at least a portion of the outer guide surface 7527 is curved along the longitudinal center line CL. The inner guide surfaces 7516, 7526 and the outer guide surface 7517, 7527 can define any suitable radius of curvature, and can have different curve shapes, similar to the shapes described above with respect to the instrument 3400. In this manner, when the second link 7610 rotates relative to the first link 7510 about the pitch axis $A_1$ (see the arrow OO in FIG. 27) the first band 7420 can contact the curved portions of the inner guide surface 7516 and the outer guide surface 7517 to maintain the desired bend geometry, band tension, and the like during actuation of the instrument 7400. Similarly, when the second link 7610 rotates relative to the first link 7510 about the pitch axis $A_1$, the second band 7440 can contact the curved portions of the inner guide surface 7526 and the outer guide surface 7527 to maintain the desired bend geometry, band tension, and the like during actuation of the instrument 7400.

Although the first guide channel 7515 and the second guide channel 7525 are curved along the longitudinal center line CL, a portion of each of the inner guide surfaces 7516, 7526 and the outer guide surfaces 7517, 7527 taken within a cross-sectional plane normal to the longitudinal center line CL is linear. As described above with reference to the actuation of the instrument 3400, this arrangement allows the inner guide surface 7516 and the outer guide surface 7517 to contact corresponding inner contact surfaces and outer contact surfaces, respectively, of the first band 7420 and the second band 7430 along a linear cross-sectional contact surface (as opposed to solely at a single point within the cross section) when the second link 7610 rotates relative to the first link 7510. This arrangement also allows the inner guide surface 7526 and the outer guide surface 7527 to contact corresponding inner contact surface and outer contact surface, respectively, of the third band 7440 and the fourth band 7450 along a linear cross-sectional contact surface when the second link 7610 rotates relative to the first link 7510.

The first guide channel 7515 (and therefore the portions of the first band 7420 and the second band 7430 therein) is offset from the longitudinal center line CL and the first axis of rotation $A_1$. In this manner, application of a force on the second link 7610 via the first band 7420 or the second band 7430 produces a torque about the first axis of rotation $A_1$. This can result in rotation of the second link 7610 relative to the first link 7510, as shown by the arrow OO in FIG. 27. The second guide channel 7525 (and therefore the portions of the third band 7440 and the fourth band 7450 therein) is offset from the longitudinal center line CL and the first axis of rotation $A_1$. In this manner, application of a force on the second link 7610 via the third band 7440 or the fourth band 7450 produces a torque about the first axis of rotation $A_1$. This can result in rotation of the second link 7610 relative to the first link 7510, as shown by the arrow OO in FIG. 27.

The second link 7610 has a proximal end portion 7611 and a distal end portion 7612. As described above, the proximal end portion 7611 includes a joint portion 7640 that is rotatably coupled to the joint portion 7540 of the first link 7510. Specifically, the joint portion 7640 includes a series of teeth 7644 that are spaced apart by recesses. The series of teeth 7644 intermesh with the series of teeth 7544 (or pins) of the first link 7510. The series of teeth 7644 and recesses can be similar to those shown and described in U.S. Patent Application Pub. No. US 2017/0120457 A1 (filed Feb. 20, 2015), entitled "Mechanical Wrist Joints with Enhanced Range of Motion, and Related Devices and Methods," which is incorporated herein by reference in its entirety.

Figure 36:
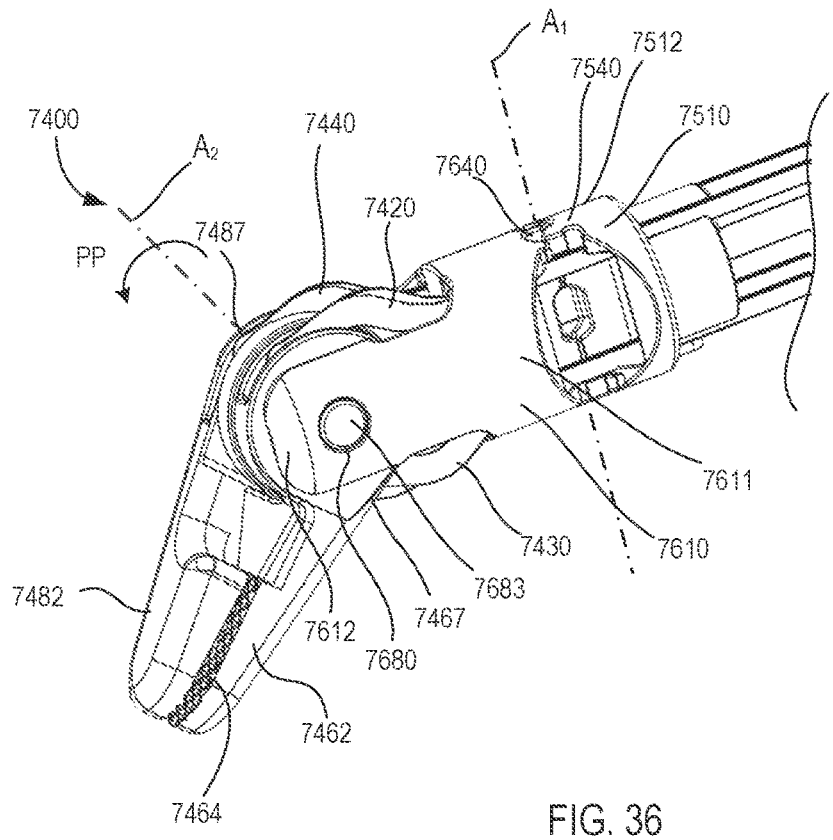
FIG. 36 is an enlarged perspective view of the distal end portion of the instrument indicated by the region Z shown in FIG. 26, with the instrument being in a second configuration.

The distal end portion 7612 of the second link 7610 includes a connector 7680 that is coupled to the end effector 7460. In this manner, the first tool member 7462 and the second tool member 7482 rotate relative to the second link 7610 about a second axis of rotation) $A_2$. The connector 7680 is a pin-type connector and includes the pin 7683 which is supported by (and placed within) the pin openings 7682. In some embodiments, the connector 7680 can include any of the structure and features of the pinned joints shown and described in U.S. Pat. No. 9,204,923 B2 (filed Jul. 16, 2008), entitled "Medical Instrument Electronically Energized Using Drive Cables," which is incorporated herein by reference in its entirety. As shown in FIG. 27, the second axis of rotation $A_2$ is non-parallel to the pitch axis $A_1$. Thus, the instrument 7400 provides for up to three degrees of freedom (i.e., a pitch motion about the first axis of rotation $A_1$, a yaw rotation about the second axis of rotation $A_2$, and a grip motion about the second axis of rotation $A_2$). For example, FIG. 36 shows the end effector 7460 transitioned to a second yaw configuration as compared to that shown in FIG. 27.

Figure 32:
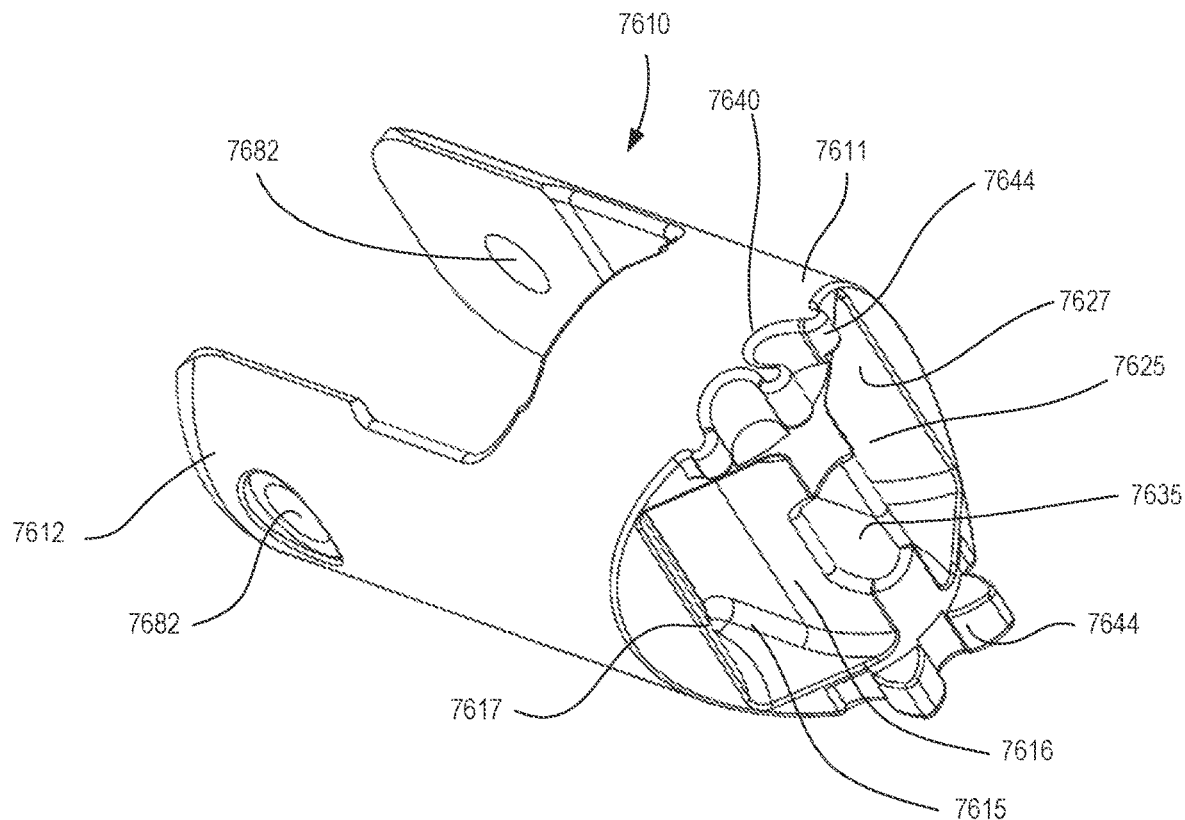
FIGS. 32 and 33 are perspective views of a second link of the wrist assembly of the instrument shown in FIG. 27.
Figure 33:
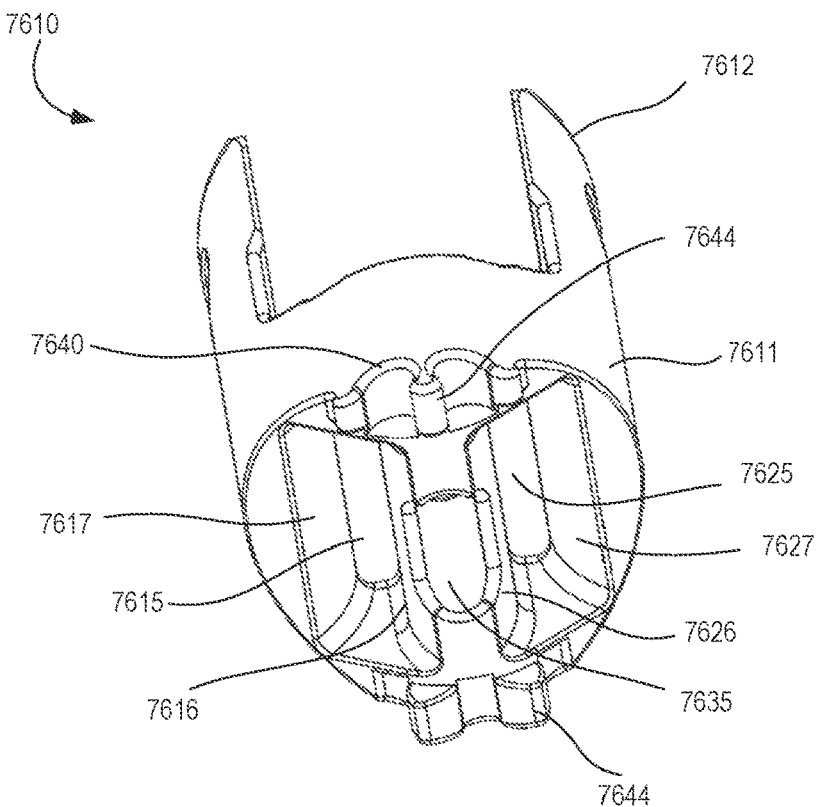

Referring to FIGS. 32 and 33, a first guide channel 7615, a second guide channel 7625, and a central bore 7635 are defined in the second link 7610. The central bore 7635 is aligned with the central bore 7535, and can contain (or allow passage of) various components of the wrist assembly, such as, for example, electrical wires. In this manner, electrical current from the backend assembly 7700 can be supplied to the end effector 7460 via components routed through the central bores 7535, 7635. The second link 7610 includes an inner guide surface 7616 and an outer guide surface 7617 that each form a portion of the boundary of the first guide channel 7615, and an inner guide surface 7626 and an outer guide surface 7627 that each form a portion of the boundary of the second guide channel 7625. The first guide channel 7615 is aligned with the first guide channel 7515 (of the first link 7510), and the second guide channel 7625 is aligned with the second guide channel 7525 (of the first link 7510). In this manner, the first band 7420 and the second band 7430 can be routed from the shaft 7410 and through the first guide channel 7515 and the first guide channel 7615 to be coupled to the first tool member 7462. The third band 7440 and the fourth band 7450 can be routed from the shaft 7410 and through the second guide channel 7525 and the second guide channel 7625 to be coupled to the second tool member 7482.

As shown in FIGS. 32 and 33, at least a portion of the inner guide surface 7616 and at least a portion of the outer guide surface 7617 is curved along the longitudinal center line CL. Similarly, at least a portion of the inner guide surface 7626 and at least a portion of the outer guide surface 7627 is curved along the longitudinal center line CL. The inner guide surfaces 7616, 7626 and the outer guide surface 7617, 7627 can define any suitable radius of curvature, and can have different curve shapes, similar to the shapes described above with respect to the instrument 3400. In this manner, when the second link 7610 rotates relative to the first link 7510 about the pitch axis $A_1$ (see the arrow OO in FIG. 27) the first band 7420 can contact the curved portions of the inner guide surface 7616 and the outer guide surface 7617 to maintain the desired bend geometry, band tension, and the like during actuation of the instrument 7400. Similarly, when the second link 7610 rotates relative to the first link 7510 about the pitch axis $A_1$, the second band 7440 can contact the curved portions of the inner guide surface 7626 and the outer guide surface 7627 to maintain the desired bend geometry, band tension, and the like during actuation of the instrument 7400.

Although the first guide channel 7615 and the second guide channel 7625 are curved along the longitudinal center line CL, a portion of each of the inner guide surfaces 7616, 7626 and the outer guide surfaces 7617, 7627 taken within a cross-sectional plane normal to the longitudinal center line CL is linear. As described above with reference to the actuation of the instrument 3400, this arrangement allows the inner guide surface 7616 and the outer guide surface 7617 to contact corresponding inner contact surfaces and outer contact surfaces, respectively, of the first band 7420 and the second band 7430 along a linear cross-sectional contact surface (as opposed to solely at a single point within the cross section) when the second link 7610 rotates relative to the first link 7510. This arrangement also allows the inner guide surface 7626 and the outer guide surface 7627 to contact corresponding inner contact surface and outer contact surface, respectively, of the third band 7440 and the fourth band 7450 along a linear cross-sectional contact surface when the second link 7610 rotates relative to the first link 7510.

The first guide channel 7615 (and therefore the portions of the first band 7420 and the second band 7430 therein) is offset from the longitudinal center line CL and the first axis of rotation $A_1$. In this manner, application of a force on the second link 7610 via the first band 7420 or the second band 7430 produces a torque about the first axis of rotation $A_1$. This results in rotation of the second link 7610 relative to the first link 7510, as shown by the arrow OO in FIG. 27. The second guide channel 7625 (and therefore the portions of the third band 7440 and the fourth band 7450 therein) is offset from the longitudinal center line CL and the first axis of rotation $A_1$. In this manner, application of a force on the second link 7610 via the third band 7440 or the fourth band 7450 produces a torque about the first axis of rotation $A_1$. This results in rotation of the second link 7610 relative to the first link 7510, as shown by the arrow OO in FIG. 27.

Figure 34:
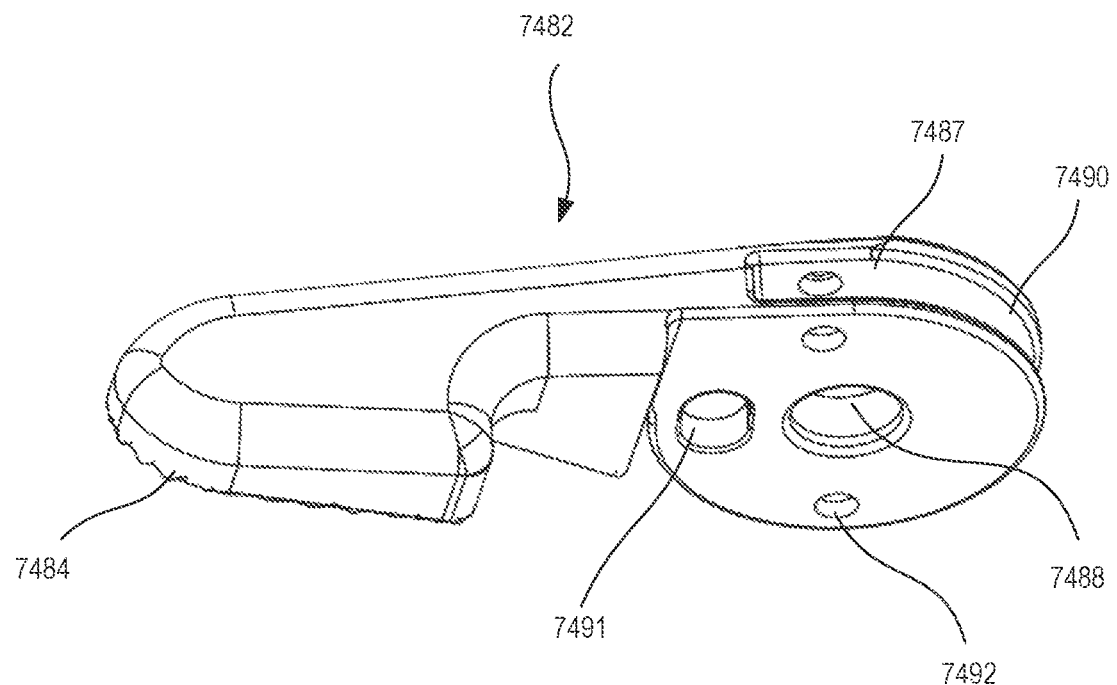
FIG. 34 is a perspective view of a first tool member of an end effector of the instrument shown in FIG. 27.
Figure 35:
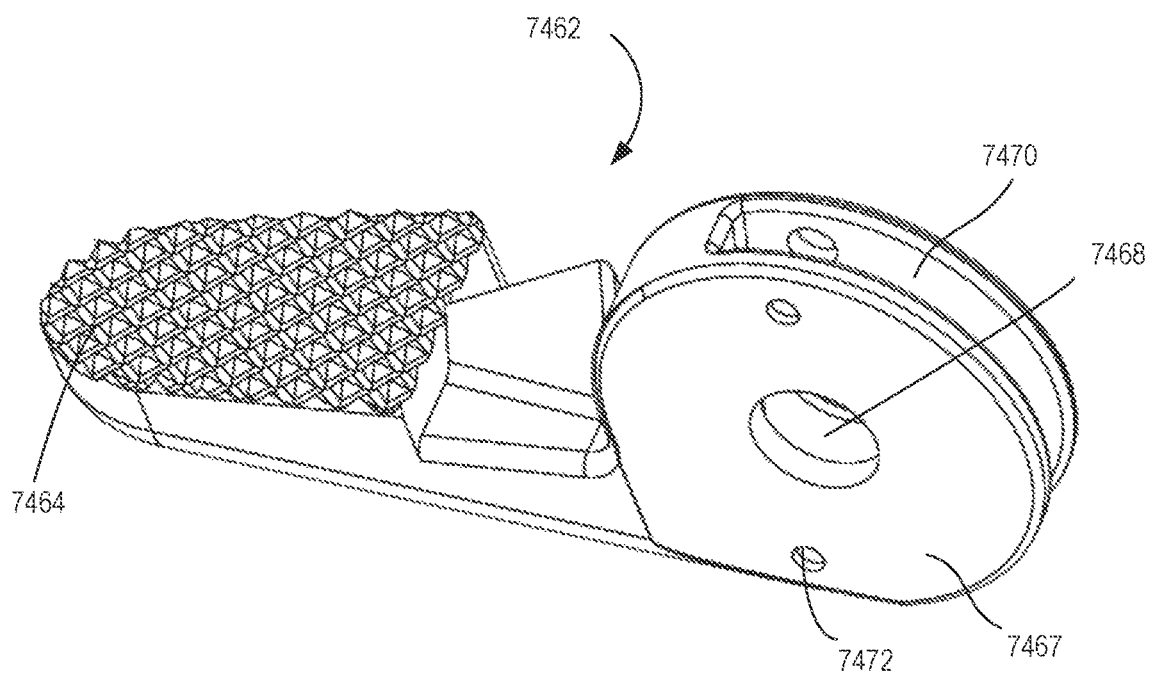
FIG. 35 is a perspective view of a second tool member of the end effector of the instrument shown in FIG. 27.

As shown in FIGS. 29, 34 and 35, the end effector 7460 includes a first tool member 7462, a second tool member 7482, and an insulator 7495. The first tool member 7462 includes a contact portion 7464 and a pulley portion 7467. The contact portion 7464 is configured to engage or manipulate a target tissue during a surgical procedure. Although shown as being a gripping surface, in other embodiments, the contact portion 7464 can be any suitable surface of the types shown and described herein (e.g., a cutter, a tissue manipulator, a cauterizing surface, or the like). The pulley portion 7467 defines a guide channel 7470, a central opening 7468, a pair of coupling openings 7472 and a guide slot (not shown, but similar to the guide slot 7491). The guide channel 7470 receives the distal end portion 7422 of the first band 7420 and the distal end portion 7432 of the second band 7430. As shown in FIG. 29, the distal end portion 7422 of the first band 7420 includes a pin that is coupled within one of the coupling openings 7472. The distal end portion 7432 of the second band 7430 includes a pin that is coupled within the second of the coupling openings 7472. The guide slot (not shown) receives a protrusion of the insulator 7495 to limit the angle through which the first tool member 7462 rotates relative to the second tool member 7482. The pulley portion 7467 is rotatably coupled to the second link 7610 via the pin 7683, which is disposed within the central opening 7468. In this manner, the first tool member 7462 rotates about the pin 7683 and relative to the second link 7610 about the second axis of rotation $A_2$, as shown by the arrow PP in FIGS. 27 and 28. Moreover, the coupling openings 7472 are offset from the yaw axis $A_2$. In this manner, application of a force by the first band 7420 or the second band 7430 on the pulley portion 7467 produces a torque on the first tool member 7462 about the yaw axis $A_2$, which results in rotation of the first tool member 7462 or the application of a gripping force.

The second tool member 7482 includes a contact portion 7484 and a pulley portion 7487. The contact portion 7484 is configured engage or manipulate a target tissue during a surgical procedure. Although shown as being a gripping surface, in other embodiments, the contact portion 7484 can be any suitable surface of the types shown and described herein (e.g., a cutter, a tissue manipulator, a cauterizing surface, or the like). The pulley portion 7487 defines a guide channel 7490, a central opening 7488, a pair of coupling openings 7492 and a guide slot 7491. The guide channel 7490 receives the distal end portion 7442 of the third band 7440 and the distal end portion 7452 of the fourth band 7450. As shown in FIG. 29, the distal end portion 7442 of the third band 7440 includes a pin that is coupled within one of the coupling openings 7492. The distal end portion 7452 of the fourth band 7450 includes a pin that is coupled within the second of the coupling openings 7492. The guide slot 7491 receives a protrusion of the insulator 7495 to limit the angle through which the first tool member 7462 rotates relative to the second tool member 7482. The pulley portion 7487 is rotatably coupled to the second link 7610 via the pin 7683, which is disposed within the central opening 7488. In this manner, the second tool member 4482 rotates about the pin 7683 and relative to the second link 7610 about the second axis of rotation $A_2$, as shown by the arrow PP in FIGS. 27 and 28. Moreover, the coupling openings 7492 are offset from the yaw axis $A_2$. In this manner, application of a force by the third band 7440 or the fourth band 7450 on the pulley portion 7487 produces a torque on the second tool member 7482 about the yaw axis $A_2$, which results in rotation of the second tool member 7482 or the application of a gripping force.

The first band 7420 has a proximal end portion 7421, a central portion 7423, and a distal end portion 7422. The second band 7430 has a proximal end portion 7431, a central portion 7433, and a distal end portion 7432. The third band 7440 has a proximal end portion 7441, a central portion 7443, and a distal end portion 7442. The fourth band 7450 has a proximal end portion 7451, a central portion 7453, and a distal end portion 7452. The proximal end portions 7421, 7431, 7441, 7451 each extend outside of the wrist assembly 7500, through the shaft 7410, and into the backend mechanism 7700. As described above, the backend mechanism 7700 can move the proximal end portions 7421, 7431, 7441, 7451 to produce a resulting movement (or force) at the respective distal end portions 7422, 7432, 7442, 7452 of the bands. The central portion 7423 of the first band 7420 and the central portion 7433 of the second band 7430 are within the first guide channels 7515, 7615, as described above. The shape of the first guide channels 7515, 7615 is such that the first band 7420 and the second band 7430 are routed through the wrist assembly 7500 in a manner that maintains the desired bend geometry, band tension, and the like during actuation of the instrument 7400. Similarly, the central portion 7443 of the third band 7440 and the central portion 7453 of the fourth band 7450 are within the second guide channels 7525, 7625, as described above. The shape of the second guide channels 7525, 7625 is such that the third band 7440 and the fourth band 7450 are routed through the wrist assembly 7500 in a manner that maintains the desired bend geometry, band tension, and the like during actuation of the instrument 7400. As described above, the distal end portions 7422, 7432, 7442, 7452 are each coupled to their respective tool members via a pin coupling. In this manner, as described herein, movement of (or a force applied to) the bands produces pitch, yaw, grip or any combination of these motions.

The bands 7420, 7430, 7440, 7450 can have any suitable shape. For example, although the bands are shown as having a rectangular cross-sectional shape (taken within a cross-sectional plane normal to the longitudinal center line CL), in other embodiments, any of the bands can have any suitable cross-sectional shape. Moreover, each of the bands has a varying size along the longitudinal center line CL. Specifically, referring to the first band 7420 as an example, the proximal end portion 7421 of the first band 7420 has a first cross-sectional area taken in a first plane normal to the longitudinal center line CL. The distal end portion 7422 has a second cross-sectional area in a second plane normal to the longitudinal center line CL. Specifically, the second cross-sectional area is less than the first cross-sectional area. In this manner, the first band 7420 can have a larger (and therefore higher strength) portion within the shaft 7410 and a smaller, more flexible portion within the wrist assembly 7500 (and being coupled to the first tool member 7462). In this embodiment, the first band 7420 transitions between the different sized portions asymmetrically about the longitudinal center line CL.

The use of the bands can provide for a low-cost, disposable instrument that is suitable for surgical procedures (including minimally-invasive procedures). In use, the distal end portion of the instrument 7400 provides for up to three degrees of freedom, and can be moved between multiple different configurations to perform a variety of surgical operations.

Figure 37:
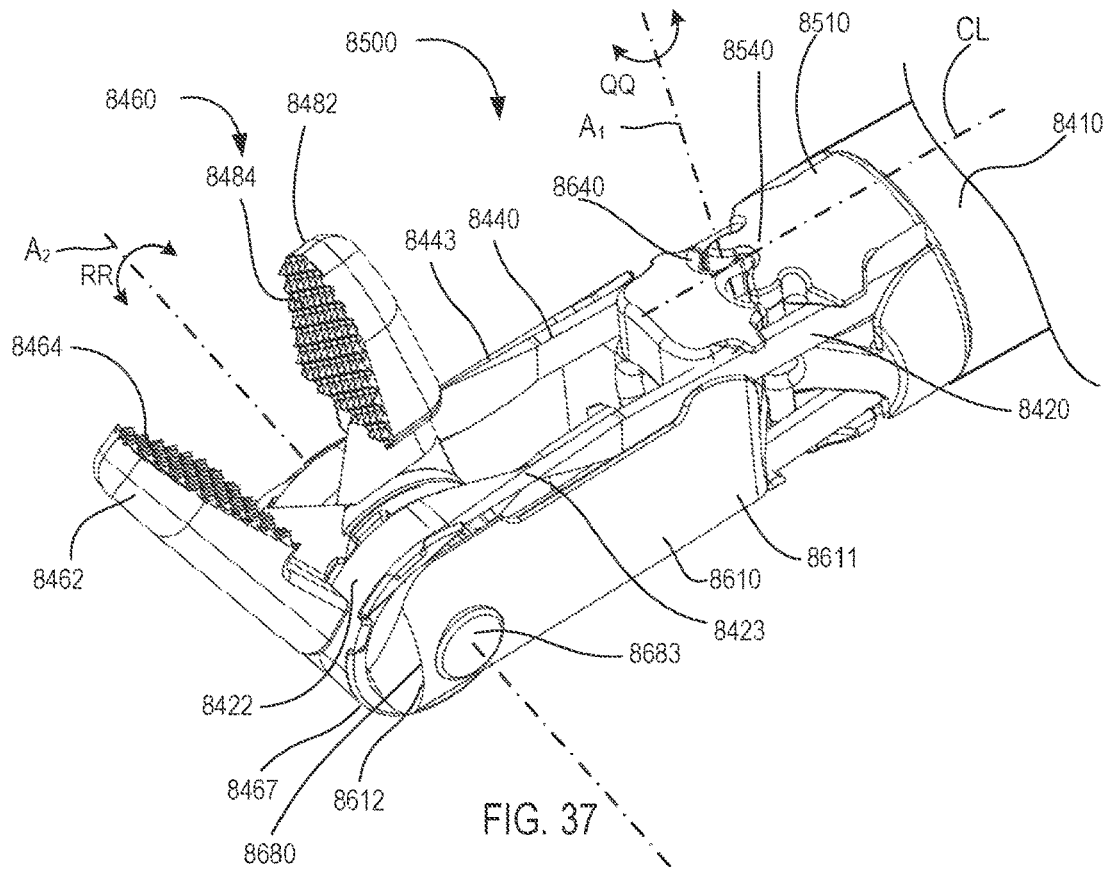
FIG. 37 is a perspective view of a distal end portion of an instrument of a surgery system, according to an embodiment.
Figure 38:
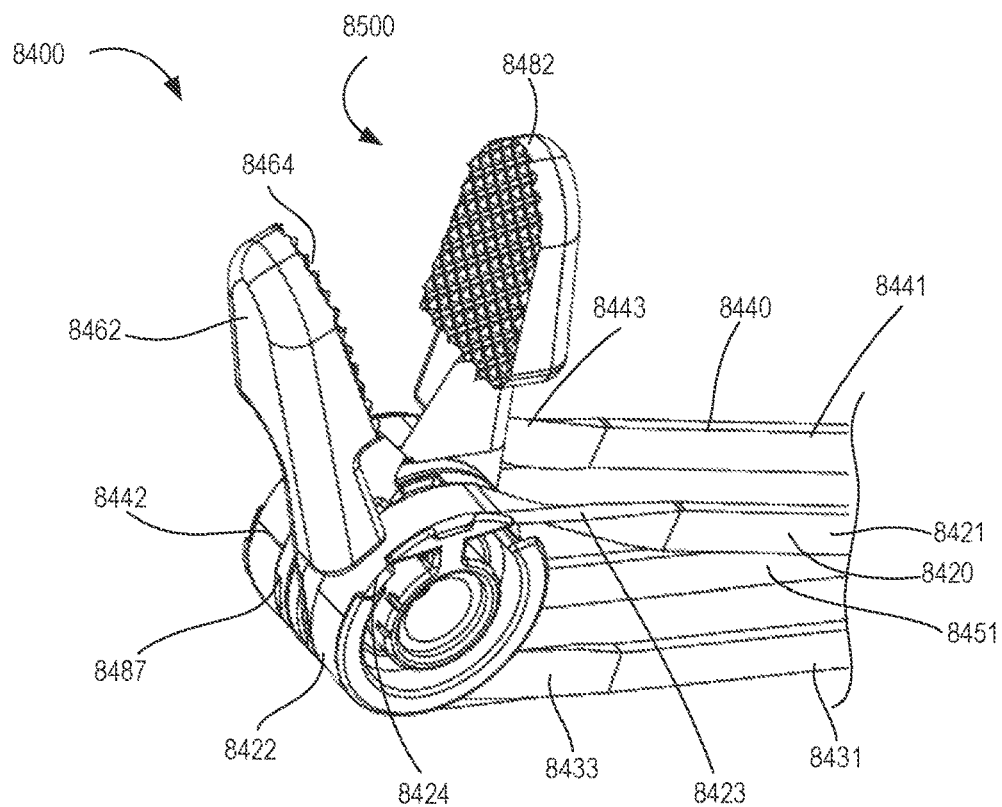
FIG. 38 is a perspective view of the end effector and the bands of the instrument shown in FIG. 37.
Figure 39:
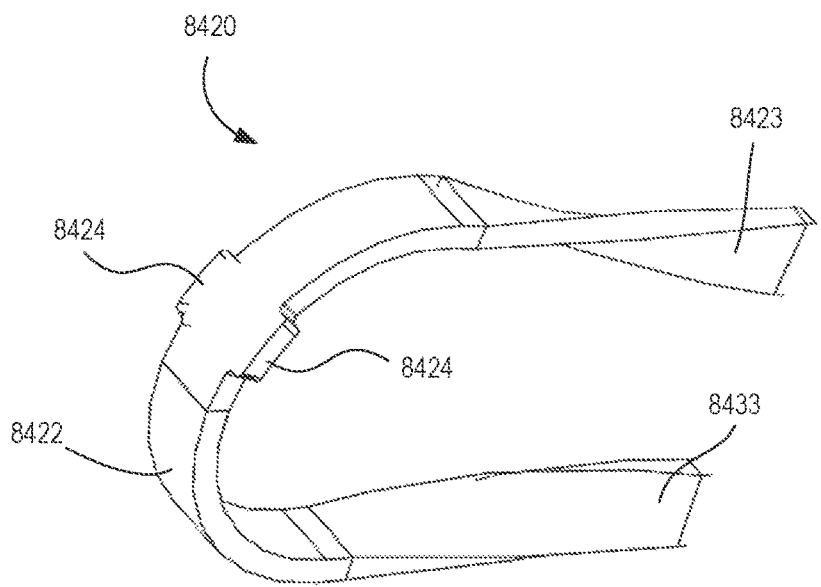
FIG. 39 is a perspective view of a portion of a band of the instrument shown in FIG. 37.

In some embodiments, an instrument can include a band that is twisted along its longitudinal center line such that the cross-sectional shape (at various positions along the longitudinal center line) is in a first orientation to produce a low area moment of inertia about a first axis and is in a second orientation to produce a low area moment of inertia about a second axis. This arrangement can allow a single band to be deformed to maintain the desired flexibility about two or more different axes (e.g., a pitch axis and a yaw axis). For example, FIGS. 37-45 are various views of a portion of an instrument 8400, according to an embodiment. In some embodiments, the instrument 8400 or any of the components therein are optionally parts of a surgical system that performs surgical procedures, and which can include a manipulator unit, a series of kinematic linkages, a series of cannulas, or the like. The instrument 8400 (and any of the instruments described herein) can be used in any suitable surgical system, such as the MIRS system 1000 shown and described above. The instrument 8400 includes an actuator assembly (not shown, but similar to the actuator assembly 7700), a shaft 8410, a wrist assembly 8500, and an end effector 8460. Referring to FIG. 37, the instrument 8400 also includes a first band 8420 and a second band 8440 that couple the backend mechanism to the wrist assembly 8500. The instrument 8400 is configured such that movement of the bands produces rotation of the wrist assembly 8500 (i.e., pitch rotation) about a first axis of rotation $A_1$ (see FIG. 37, which functions as the pitch axis, the term pitch is arbitrary), yaw rotation of the end effector 8460 about a second axis of rotation $A_2$ (see FIG. 37, which functions as the yaw axis), grip rotation of the tool members of the end effector 8460 about the yaw axis, or any combination of these movements. Changing the pitch, yaw, or grip of the instrument 8400 can be performed by manipulating the bands in similar manner as that described above for the instrument 6400. Thus, the specific movement of various portions of the first band 8420 and the second band 8440 to accomplish the desired motion is not described below.

Figure 40:
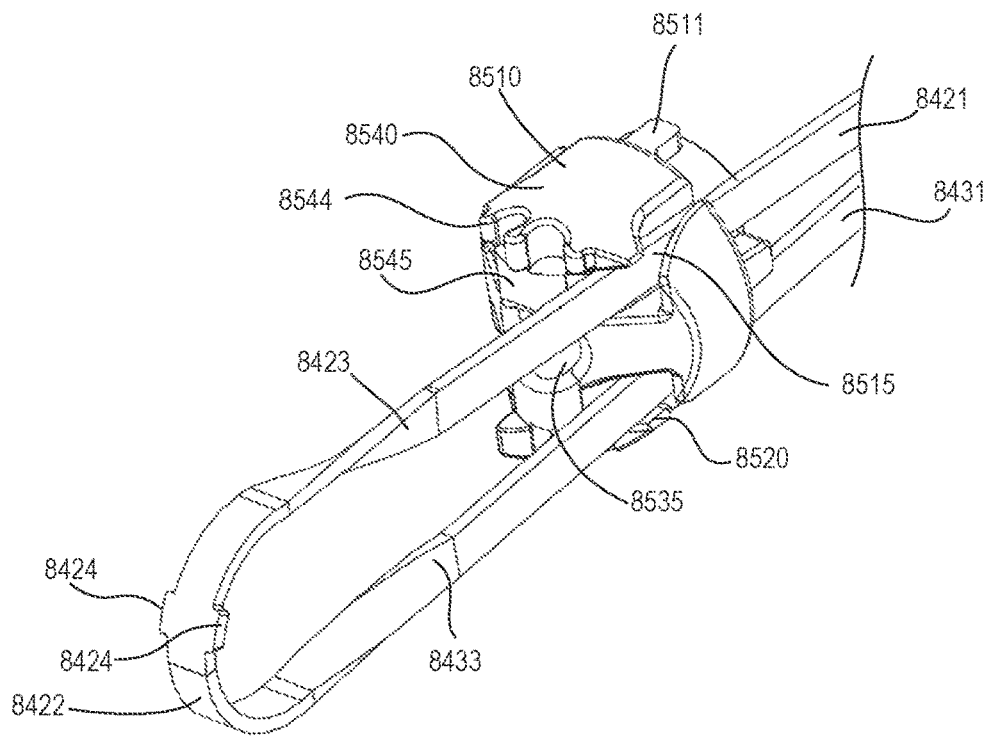
FIG. 40 is a perspective view of a portion of the band and a first link of the instrument shown in FIG. 37.
Figure 41:
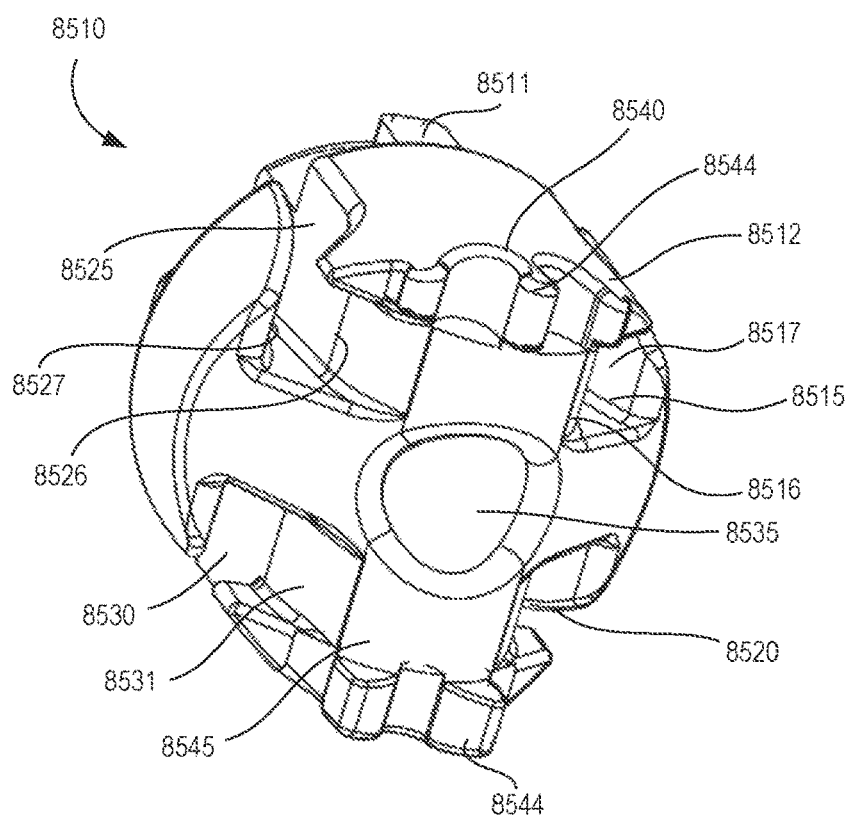
FIG. 41 is a left side perspective view of the first link of a wrist assembly of the instrument shown in FIG. 37.
Figure 43:
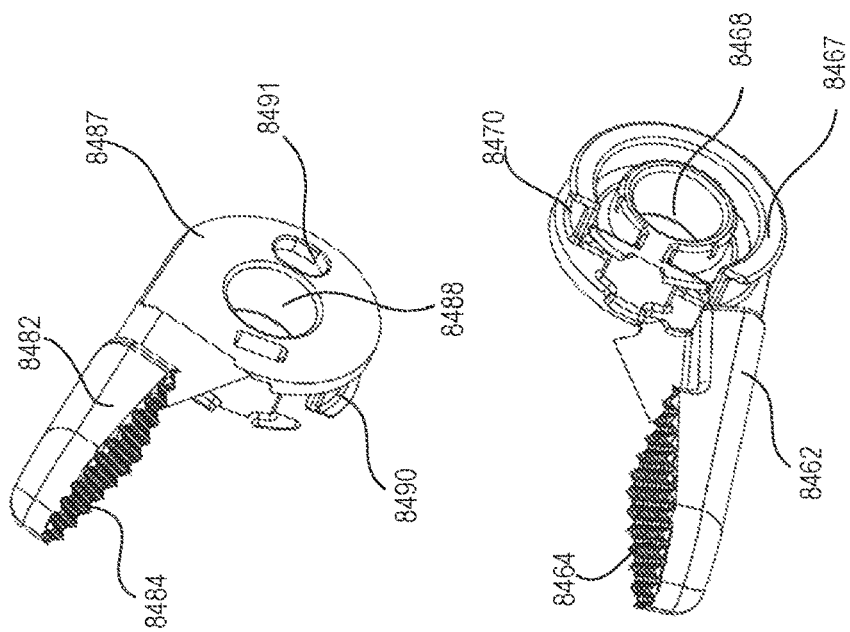
FIGS. 43 and 44 are perspective views of a first tool member and a second tool member of an end effector of the instrument shown in FIG. 37.

The wrist assembly 8500 includes a proximal first link 8510 and a distal second link 8610. As shown in FIGS. 37, 40, and 41, the first link 8510 has a proximal end portion 8511 and a distal end portion 8512. The proximal end portion 8511 is coupled to the distal end portion of the shaft 8410. The proximal end portion 8511 can be coupled to the shaft 8410 via any suitable mechanism, as described herein. The distal end portion 8512 includes a joint portion 8540 that is rotatably coupled to a mating joint portion 8640 of the second link 8610. In this manner, the first link 8510 and the second link 8610 form the wrist assembly 8500 having a first axis of rotation $A_1$ (which functions as the pitch axis, the term pitch is arbitrary) about which the second link 8610 rotates relative to the first link 8510. Specifically, the joint portion 8540 includes a series of teeth 8544 that are spaced apart by recesses, and two curved contact surfaces 8545. The series of teeth 8544 intermesh with the series of teeth 8644 (or pins) of the second link 8610, and the curved contact surfaces 8545 are in rolling contact with the corresponding contact surfaces 8645 of the second link 8610.

Referring to FIG. 41, a first guide channel 8515, a second guide channel 8520, a third guide channel 8525, a fourth guide channel 8530, and a central bore 8535 are defined in the first link 8510. The central bore 8535 can contain (or allow passage of) various components of the wrist assembly, such as, for example, electrical wires. The first guide channel 8515 is at least partially defined by an inner guide surface 8516 and an outer guide surface 8517. A first proximal end portion 8421 of the first band 8420 is movably disposed within the first guide channel 8515. The second guide channel 8520 is at least partially defined by an inner guide surface and an outer guide surface (not identified). A second proximal end portion 8431 of the first band 8420 is movably disposed within the second guide channel 8520. In this manner, the first link 8510 differs from the first link 7510 in that the band members (or portions) coupled to the first tool member 8462 are within guide channels that are separated. In some embodiments, however, the first guide channel 8515 can be combined with the second guide channel 8520 to form a single channel within which the first proximal end portion 8421 and the second proximal end portion 8431 are disposed. The third guide channel 8525 is at least partially defined by an inner guide surface 8526 and an outer guide surface 8527. A first proximal end portion 8441 of the second band 8440 is movably disposed within the third guide channel 8525. The fourth guide channel 8530 is at least partially defined by an inner guide surface 8531 and an outer guide surface (not identified). A second proximal end portion 8451 of the second band 8440 is movably disposed within the fourth guide channel 8530. In some embodiments, the third guide channel 8525 can be combined with the fourth guide channel 8530 to form a single channel within which the first proximal end portion 8441 and the second proximal end portion 8451 are disposed.

As shown in FIG. 37, the first link 8510 and the second link 8610 define a longitudinal center line CL that intersects the pitch axis $A_1$ when the instrument 8400 is in an initial (or "straight" configuration). Similar as described above with respect to the first link 7510, the guide channels of the first link 8510 are curved along the longitudinal center line CL. Specifically, the inner guide surfaces (e.g., the inner guide surfaces 8516, 8526, 8531) and the outer guide surfaces (e.g., the outer guide surfaces 8517, 8527) can define any suitable radius of curvature, and can have different curve shapes, similar to the shapes described above with respect to the instrument 3400. In this manner, when the second link 8610 rotates relative to the first link 8510 about the pitch axis $A_1$ (see the arrow QQ in FIG. 37) the first proximal end portion 8421 and the second proximal end portion 8431 of the first band 8420 and the first proximal end portion 8441 and the second proximal end portion 8451 of the second band 8440 can contact the curved portions of their respective inner guide surface and the outer guide surface to maintain the desired bend geometry, band tension, and the like during actuation of the instrument 8400. Moreover, as described above, the guide channels 8515, 8520, 8525, 8530 are offset from the longitudinal center line CL and the first axis of rotation $A_1$. In this manner, application of a force on the second link 8610 via the first band 8420 or the second band 8440 produces a torque about the first axis of rotation $A_1$. This results in rotation of the second link 8610 relative to the first link 8510, as shown by the arrow QQ in FIG. 37.

The second link 8610 has a proximal end portion 8611 and a distal end portion 8612. As described above, the proximal end portion 8611 includes a joint portion 8640 that is rotatably coupled to the joint portion 8540 of the first link 8510. Specifically, the joint portion 8640 includes a series of teeth 8644 that are spaced apart by recesses, and two curved contact surfaces 8645. The series of teeth 8644 intermesh with the series of teeth 8544 (or pins) of the first link 8510, and the curved contact surfaces 8645 are in rolling contact with the corresponding contact surfaces 8545 of the first link 8510. The distal end portion 8612 of the second link 8610 includes a connector 8680 that is coupled to the end effector 8460. In this manner, the first tool member 8462 and the second tool member 8482 rotate relative to the second link 8610 about a second axis of rotation $A_2$. The connector 8680 is a pin-type connector and includes the pin 8683 which is supported by (and placed within) the pin openings 8682. In some embodiments, the connector 8680 can include any of the structure and features of the pinned joints shown and described in U.S. Pat. No. 9,204,923 B2 (filed Jul. 16, 2008), entitled "Medical Instrument Electronically Energized Using Drive Cables," which is incorporated herein by reference in its entirety. As shown in FIG. 37, the second axis of rotation $A_2$ is non-parallel to the pitch axis $A_1$. Thus, the instrument 8400 provides for up to three degrees of freedom (i.e., a pitch motion about the first axis of rotation $A_1$, a yaw rotation about the second axis of rotation $A_2$, and a grip motion about the second axis of rotation $A_2$).

Figure 42:
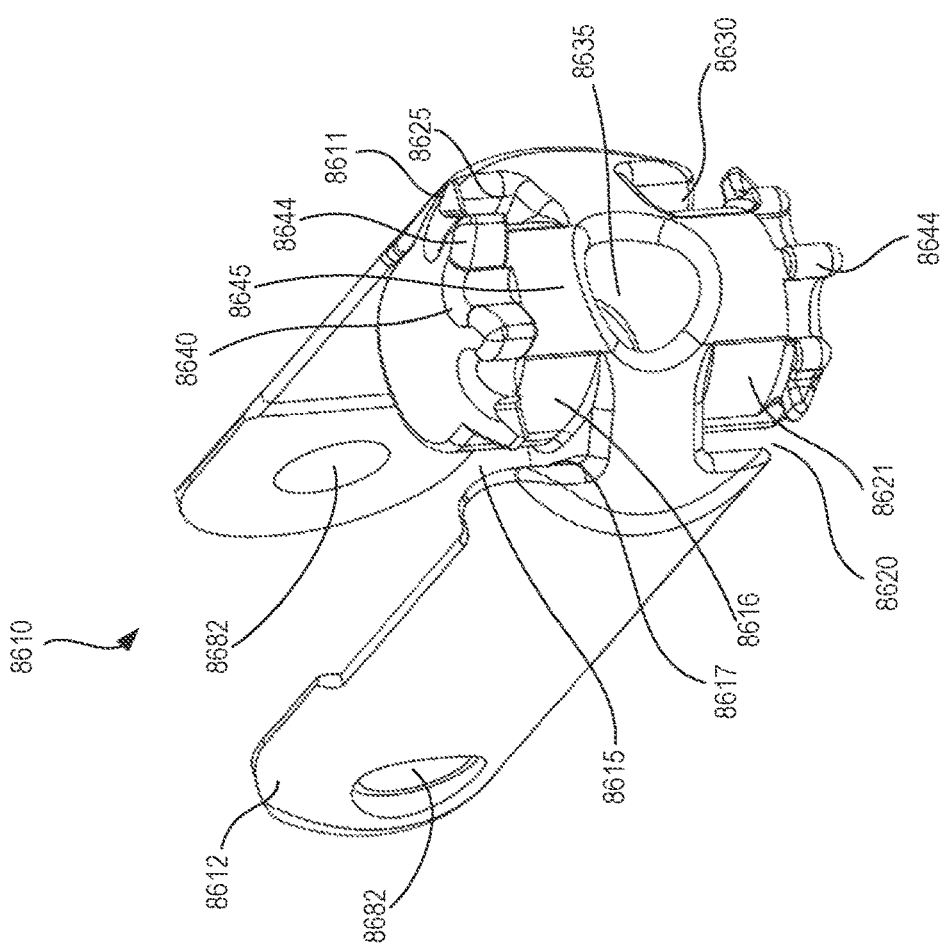
FIG. 42 is a perspective view of a second link of the wrist assembly of the instrument shown in FIG. 37.
Figure 44:
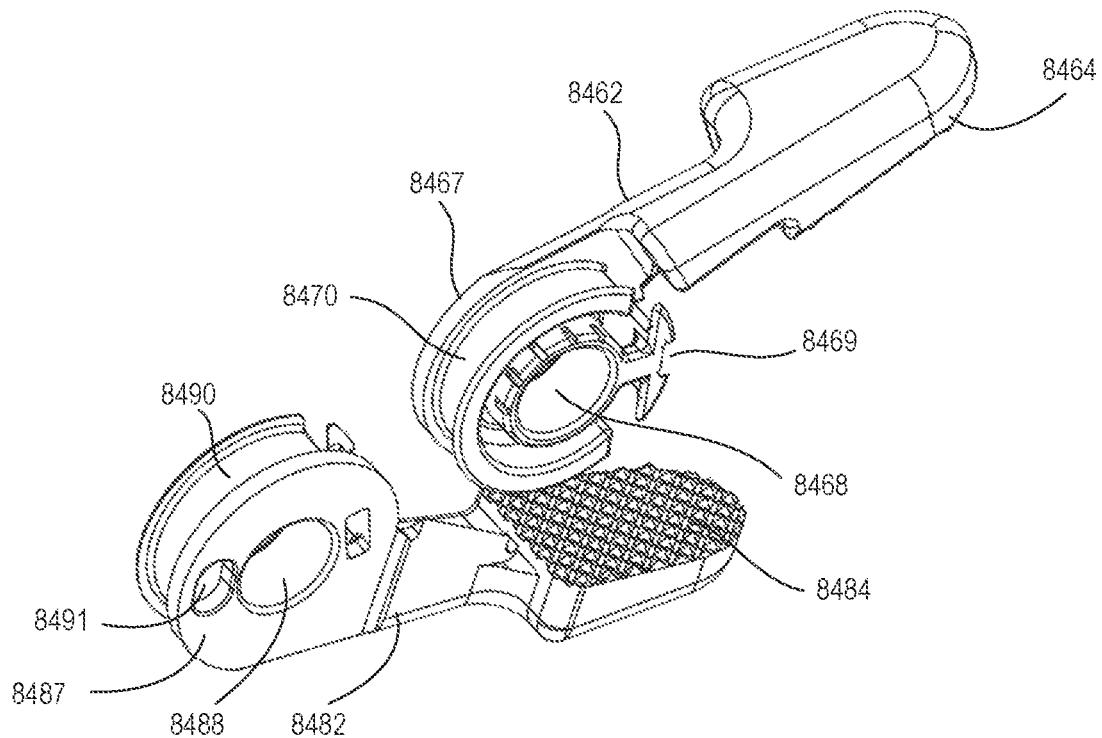

Referring to FIG. 42, a first guide channel 8615, a second guide channel 8620, a third guide channel 8625, a fourth guide channel 8630, and a central bore 8635 are defined in the second link 8610. The central bore 8635 is aligned with the central bore 8535 and can contain (or allow passage of) various components of the wrist assembly, such as, for example, electrical wires. In this manner, electrical current from the backend assembly can be supplied to the end effector 8460 via components routed through the central bores 8535, 8635. The first guide channel 8615 is at least partially defined by an inner guide surface 8616 and an outer guide surface 8617. The second guide channel 8620 is at least partially defined by an inner guide surface 8621 and an outer guide surface (not identified). The first guide channel 8615 is aligned with the first guide channel 8515 (of the first link 8510), and the second guide channel 8620 is aligned with the second guide channel 8520 (of the first link 8510). In this manner, a portion (e.g., the first proximal portion 8421) of the first band 8420 is routed from the shaft 8410 and through the first guide channel 8515 and the first guide channel 8615 to be coupled to the first tool member 8462. A portion (e.g., a second portion 8431) of the first band 8420 is routed from the first tool member 8462 and back through the second guide channel 8520 and the second guide channel 8620 to be returned to the backend mechanism (via the shaft). Similarly, the third guide channel 8625 is at least partially defined by an inner guide surface and an outer guide surface (not identified). The second guide channel 8620 is at least partially defined by an inner guide surface and an outer guide surface (not identified). The third guide channel 8625 is aligned with the third guide channel 8525 (of the first link 8510), and the fourth guide channel 8630 is aligned with the fourth guide channel 8530 (of the first link 8510). In this manner, a portion (e.g., the first proximal portion 8441) of the second band 8440 is routed from the shaft 8410 and through the third guide channel 8525 and the third guide channel 8625 to be coupled to the second tool member 8482. A portion (e.g., a second portion 8451) of the second band 8440 is routed from the second tool member 8482 and back through the fourth guide channel 8530 and the fourth guide channel 8630 to be returned to the backend mechanism (via the shaft).

In some embodiments, the first guide channel 8615 can be combined with the second guide channel 8620 to form a single channel within which the first proximal end portion 8421 and the second proximal end portion 8431 are disposed. In some embodiments, the third guide channel 8625 can be combined with the fourth guide channel 8630 to form a single channel within which the first proximal end portion 8441 and the second proximal end portion 8451 are disposed.

Similar as described above with respect to the second link 7610, the guide channels of the second link 8610 are curved along the longitudinal center line CL. Specifically, the inner guide surfaces (e.g., the inner guide surfaces 8616, 8621) and the outer guide surfaces (e.g., the outer guide surface 8617) can define any suitable radius of curvature, and can have different curve shapes, similar to the shapes described above with respect to the instrument 3400. In this manner, when the second link 8610 rotates relative to the first link 8510 about the pitch axis $A_1$ (see the arrow QQ in FIG. 37) portions of the first band 8420 and portions of the second band 8440 can contact the curved portions of their respective inner guide surface and the outer guide surface to maintain the desired bend geometry, band tension, and the like during actuation of the instrument 8400. Moreover, as described above, the guide channels 8615, 8620, 8625, 8630 are offset from the longitudinal center line CL and the first axis of rotation $A_1$. In this manner, application of a force on the second link 8610 via the first band 8420 or the second band 8440 produces a torque about the first axis of rotation $A_1$. This results in rotation of the second link 8610 relative to the first link 8510, as shown by the arrow QQ in FIG. 37.

Figure 45:
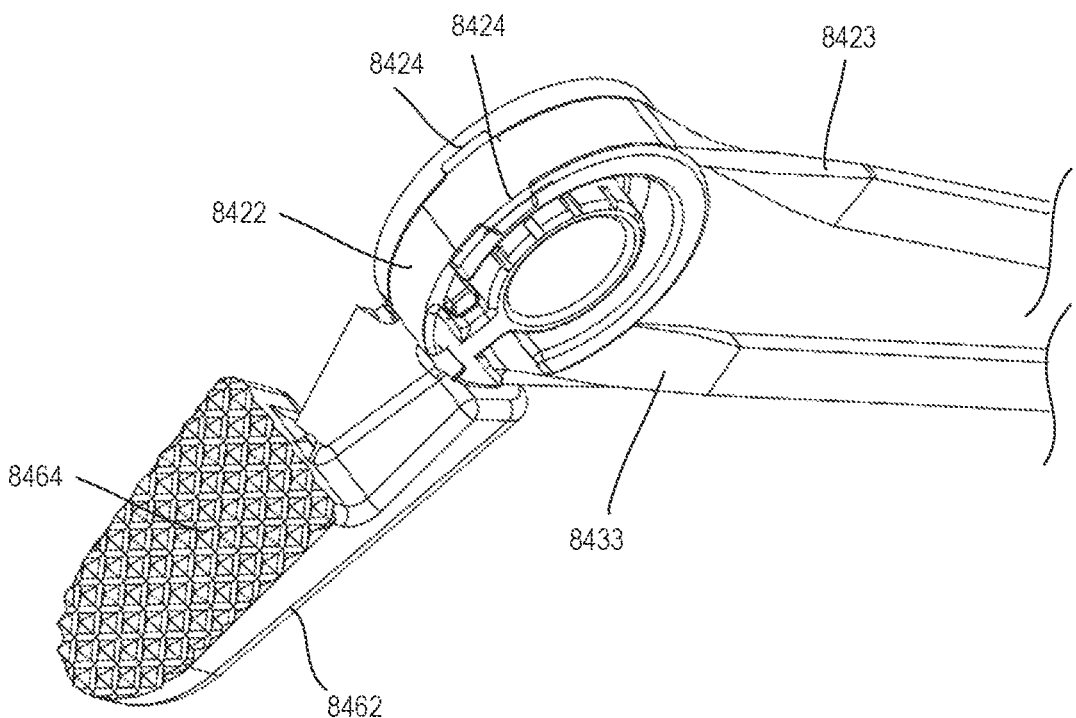
FIG. 45 is a perspective view of a portion of the band and the first tool member of the instrument shown in FIG. 37.

As shown in FIGS. 37, 38, 43, and 44, the end effector 8460 includes a first tool member 8462 and a second tool member 8482. The first tool member 8462 includes a contact portion 8464 and a pulley portion 8467. The contact portion 8464 is configured engage or manipulate a target tissue during a surgical procedure. Although shown as being a gripping surface, in other embodiments, the contact portion 8464 can be any suitable surface of the types shown and described herein (e.g., a cutter, a tissue manipulator, a cauterizing surface, or the like). The pulley portion 8467 includes a guide surface 8470, a central opening 8468, and a pair of connection slots 8469 (only one of the slots is identified in FIG. 44). In some embodiments, the pulley portion 8467 can include a guide slot (not shown, but similar to the guide slot 8491) or a guide pin (not shown). The guide surface 8470 is within a channel and is the surface about which the distal end portion 8422 of the first band 8420 is wrapped. As shown in FIG. 45, the distal end portion 8422 of the first band 8420 includes a pair of connection tabs 8424 that are coupled within the corresponding connection slots 8469. The pulley portion 8467 is rotatably coupled to the second link 8610 via the pin 8683, which is disposed within the central opening 8468. In this manner, the first tool member 8462 rotates about the pin 8683 and relative to the second link 8610 about the second axis of rotation $A_2$, as shown by the arrow RR in FIG. 37. Moreover, the guide surface 8470 is offset from the yaw axis $A_2$ (i.e., by the radius of the guide surface 8470). In this manner, application of a force by the first band 8420 on the pulley portion 8467 produces a torque on the first tool member 8462 about the yaw axis $A_2$, which results in rotation of the first tool member 8462 or the application of a gripping force.

The second tool member 8482 includes a contact portion 8484 and a pulley portion 8487. The contact portion 8484 is configured engage or manipulate a target tissue during a surgical procedure. Although shown as being a gripping surface, in other embodiments, the contact portion 8484 can be any suitable surface of the types shown and described herein (e.g., a cutter, a tissue manipulator, a cauterizing surface, or the like). The pulley portion 8487 includes a guide surface 8490, a central opening 8488, a pair of connection slots (not identified, but similar to the connection slots 8469), and a guide slot 8491. The guide surface 8490 is within a channel and is the surface about which the distal end portion 8442 of the second band 8440 is wrapped. The second band 8440 is coupled to the guide surface 8490 by a pair of connection tabs (similar to the tabs 8424) that are coupled within the corresponding connection slots. The guide slot 8491 receives a protrusion of the first tool member 8462 (not shown) or a protrusion of an intermediate component (e.g., an insulator, not shown) to limit the angle through which the first tool member 8462 rotates relative to the second tool member 8482.

The pulley portion 8487 is rotatably coupled to the second link 8610 via the pin 8683, which is disposed within the central opening 8488. In this manner, the second tool member 8482 rotates about the pin 8683 and relative to the second link 8610 via the yaw $A_2$, as shown by the arrow RR in FIG. 37. Moreover, the guide surface 8490 is offset from the yaw axis $A_2$ (i.e., by the radius of the guide surface 8490). In this manner, application of a force by the second band 8440 on the pulley portion 8487 produces a torque on the second tool member 8482 about the yaw axis $A_2$, which results in rotation of the second tool member 8482 or the application of a gripping force.

The first band 8420 (which acts as a tension member) has a first proximal end portion 8421, a second proximal end portion 8431, a distal end portion 8422, a first central portion 8423, and a second central portion 8433. As shown, the distal end portion 8422 is wrapped about and coupled to the pulley portion 8467 of the first tool member 8462. The first proximal end portion 8421 and the second proximal end portion 8431 each extend through the first link 8510 (i.e., the first guide channel 8515 and the second guide channel 8520, respectively) and into the shaft 8410. As described herein, the shape of the guide channels is such that the first band 8420 is routed through the wrist assembly 8500 in a manner that maintains the desired bend geometry, band tension, and the like during actuation of the instrument 8400. Additionally, the first proximal end portion 8421 and the second proximal end portion 8431 each extend through the shaft 8410 and are coupled to a backend mechanism (not shown, but similar to the actuator 7700 described above) that can move each of the proximal end portions to produce pitch, yaw, and gripping movements of the wrist assembly 8500.

The first central portion 8423 is between the first proximal end portion 8421 and the distal end portion 8422, and the second central portion 8433 is between the second proximal end portion 8431 and the distal end portion 8422. As shown, the first band 8420 is twisted along its longitudinal center line in two places: the first region of twist is along the first central portion 8423 and the second region of twist is along the second central portion 8433. In this manner, the orientation of the contact surfaces of the first band 8420 at the first proximal end portion 8421 and the second proximal end portion 8431 (i.e., the band surfaces that contact or are wrapped about the inner and outer guide surfaces) are different than an orientation of the contact surface of the first band 8420 at the distal end portion 8422 (i.e., the band surface that is wrapped about the contact surface 8470).

The second band 8440 (which also acts as a tension member) has a first proximal end portion 8441, a second proximal end portion 8451, a distal end portion 8442, a first central portion 8443, and a second central portion (not identified). As shown, the distal end portion 8442 is wrapped about and coupled to the pulley portion 8487 of the second tool member 8482. The first proximal end portion 8441 and the second proximal end portion 8451 each extend through the first link 8510 (i.e., the third guide channel 8525 and the fourth guide channel 8530, respectively) and into the shaft 8410. The shape of the guide channels is such that the second band 8440 is routed through the wrist assembly 8500 in a manner that maintains the desired bend geometry, band tension, and the like during actuation of the instrument 8400. Additionally, the first proximal end portion 8441 and the second proximal end portion 8451 each extend through the shaft 8410 and are coupled to a backend mechanism (not shown, but similar to the actuator 7700 described above) that can move each of the proximal end portions to produce pitch, yaw, and gripping movements of the wrist assembly 8500.

The first central portion 8443 is between the first proximal end portion 8421 and the distal end portion 8442, and the second central portion (not shown) is between the second proximal end portion 8451 and the distal end portion 8442. As shown, the second band 8440 is twisted along its longitudinal center line in two places: the first region of twist is along the first central portion 8443 and the second region of twist is along the second central portion. In this manner, the orientation of the contact surfaces of the second band 8440 at the first proximal end portion 8441 and the second proximal end portion 8451 (i.e., the band surfaces that contact or are wrapped about the inner and outer guide surfaces) are different than an orientation of the contact surface of the second band 8440 at the distal end portion 8442 (i.e., the band surface that is wrapped about the contact surface 8490).

As described above with reference to the instrument 4400, the twisted arrangement allows the area moment of inertia of the first band 8420 and the second band 8440 about the desired axis of deformation to minimized Thus, the flexibility of the first band 8420 and the second band 8440 is maximized at both the proximal end portions (to facilitate rotation of the second link member 8610 about the pitch axis $A_1$) and the distal end portions (to facilitate rotation of the first tool member 8462 and the second tool member 8482 about the yaw axis $A_2$). Although the first band 8420 and the second band 8440 are shown as being twisted by a twist angle of 90 degree (i.e., the same as the angle defined between the first axis of rotation $A_1$ and the second axis of rotation $A_2$), in other embodiments, the first band 8420 and the second band 8440 can be twisted by any suitable twist angle.

The first band 8420 and the second band 8440 can have any suitable shape. For example, although the bands are shown as having a rectangular cross-sectional shape (taken within a cross-sectional plane normal to the longitudinal center line CL), in other embodiments, any of the bands can have any suitable cross-sectional shape. Moreover, in some embodiments, each of the bands can have a varying size along the longitudinal center line CL. Specifically, referring to the first band 8420 as an example, the first proximal end portion 8421 can transition (e.g., within the shaft 8410) to have a larger cross-sectional area similar to that described for the first band 7420. In this manner, the first band 8420 can have a larger (and therefore higher strength) portion within the shaft 8410 and a smaller, more flexible portion within the wrist assembly 8500 (and being coupled to the first tool member 8462).

Figure 46:
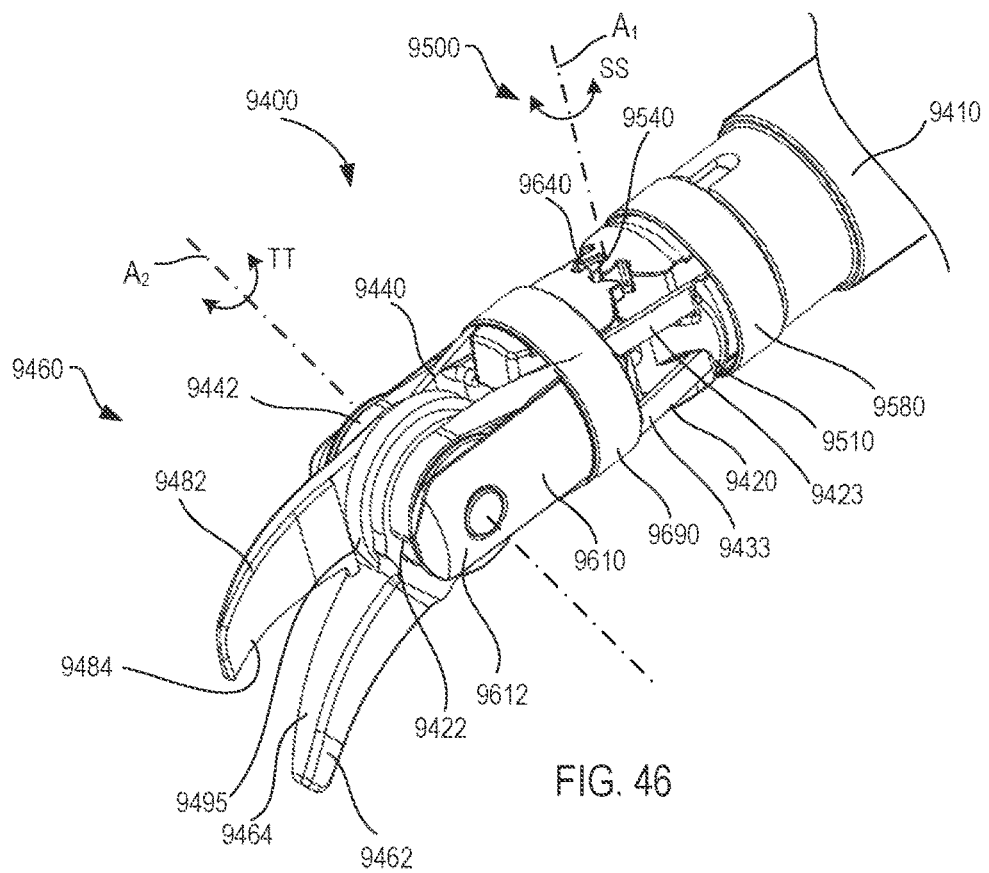
FIG. 46 is a perspective view of a distal end portion of an instrument of a surgery system, according to an embodiment.
Figure 47:
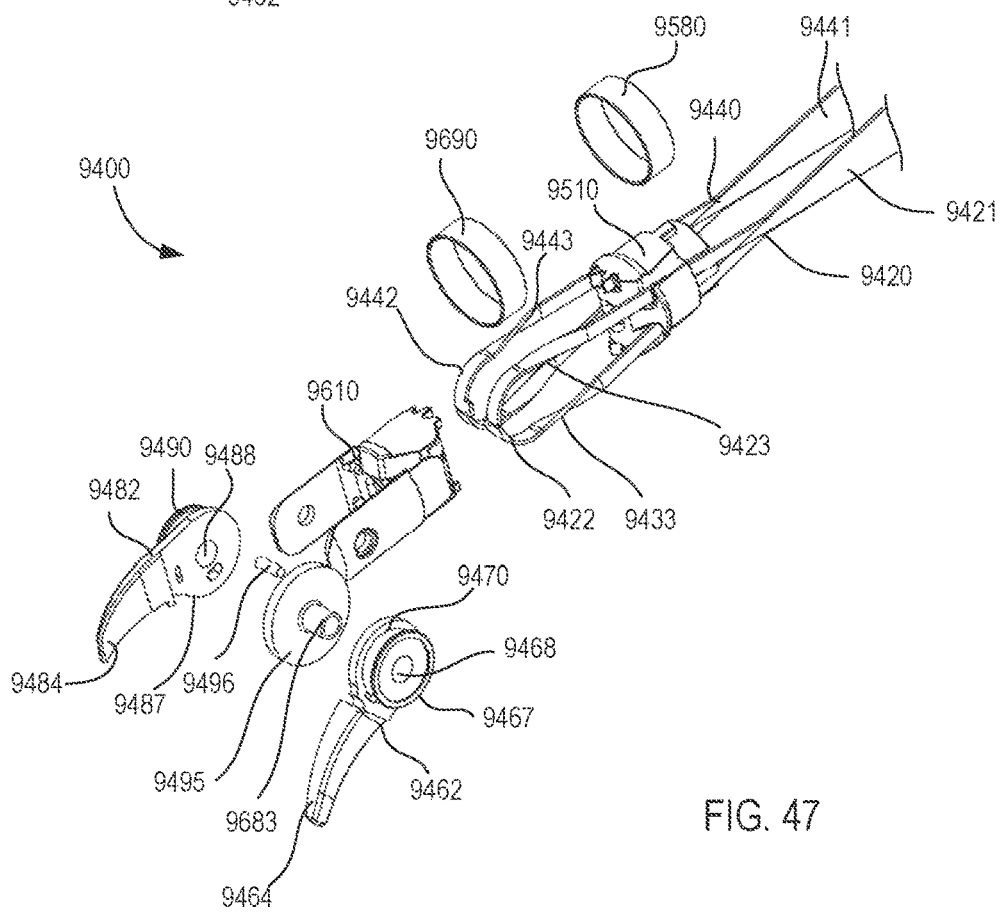
FIG. 47 is an exploded perspective view of the distal end portion of the instrument shown in FIG. 46.
Figure 48:
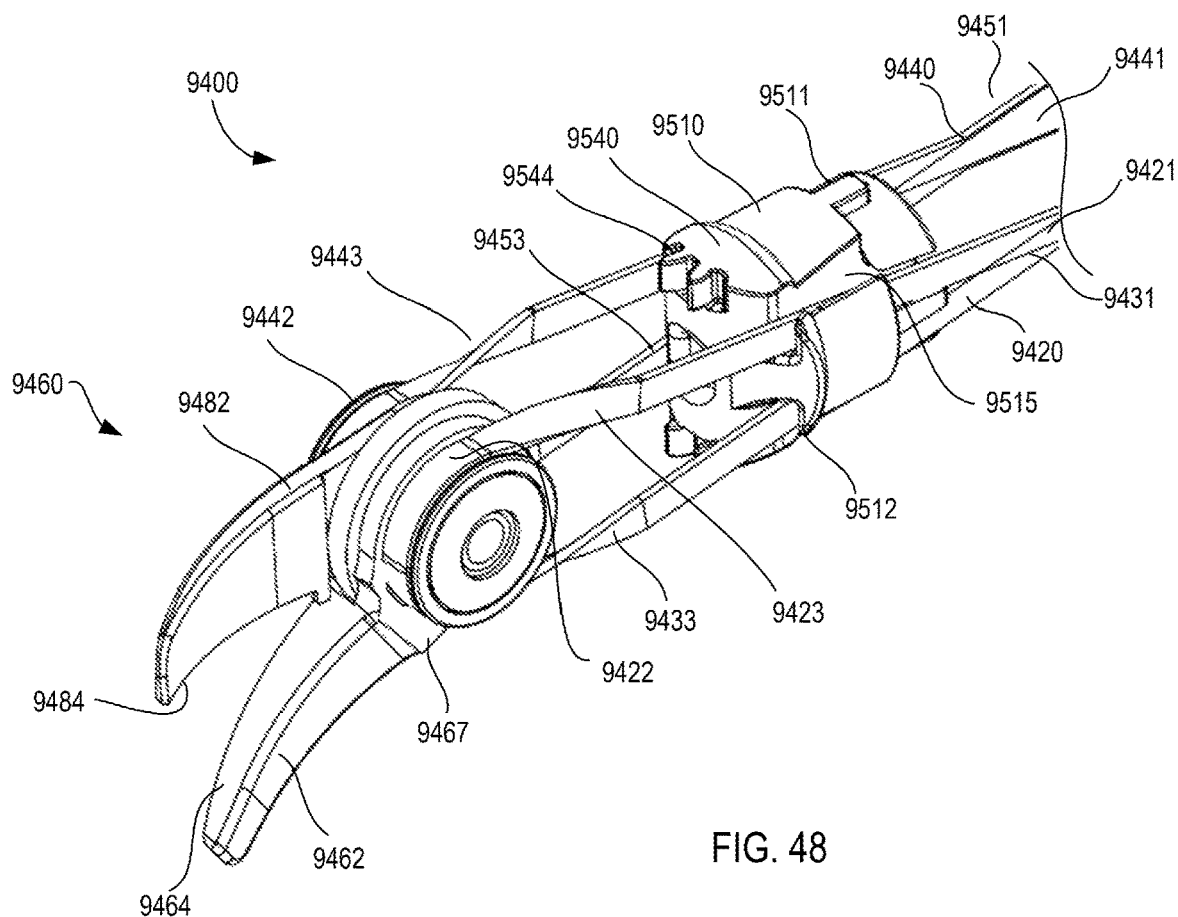
FIG. 48 is a perspective view of the distal end portion of the instrument shown in FIG. 46 with the shaft and the second link removed to show the end effector, the bands and the first link.

The guide channels of the first link 8510 and the second link 8610 are shown and described above as including side openings into the respective guide channel. In this manner, portions of the bands can be easily placed into the desired guide channel during assembly. For example, the side opening into the first guide channel 8515 allows the first proximal end portion 8421 of the band to be placed into the guide channel 8515. Although not shown in the instrument 8400, in some embodiments, any of the instruments described herein can include one or more covers or lock rings that cover the side openings. The use of such covers or lock rings maintains the band within its guide channel, and also limits the likelihood that the narrow side edges of the band will inadvertently contact bodily tissue. For example, FIGS. 46-52 are various views of a portion of an instrument 9400, according to an embodiment. In some embodiments, the instrument 9400 or any of the components therein are optionally parts of a surgical system that performs surgical procedures, and which can include a manipulator unit, a series of kinematic linkages, a series of cannulas, or the like. The instrument 9400 (and any of the instruments described herein) can be used in any suitable surgical system, such as the MIRS system 1000 shown and described above. The instrument 9400 includes an actuator assembly (not shown, but similar to the actuator 7700), a shaft 9410, a wrist assembly 9500, and an end effector 9460. Referring to FIG. 47, the instrument 9400 also includes a first band 9420 and a second band 9440 that couple the backend mechanism to the wrist assembly 9500. The instrument 9400 is configured such that movement of the bands produces rotation of the wrist assembly 9500 (i.e., pitch rotation) about a first axis of rotation $A_1$ (see FIG. 46, which functions as the pitch axis, the term pitch is arbitrary), yaw rotation of the end effector 9460 about a second axis of rotation $A_2$ (see FIG. 46, which functions as the yaw axis), grip rotation of the tool members of the end effector 9460 about the yaw axis, or any combination of these movements. Changing the pitch, yaw, or grip of the instrument 9400 can be performed by manipulating the bands in similar manner as that described above for the instrument 6400. Thus, the specific movement of various portions of the first band 9420 and the second band 9440 to accomplish the desired motion is not described below.

Figure 49:
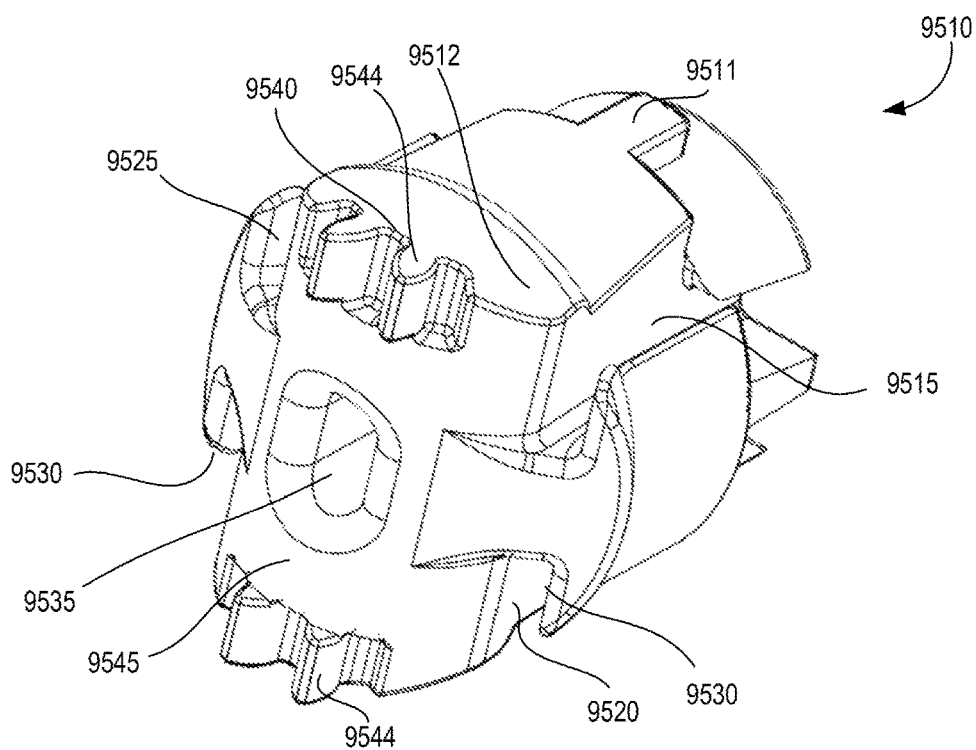
FIG. 49 is a left side perspective view.
Figure 50:
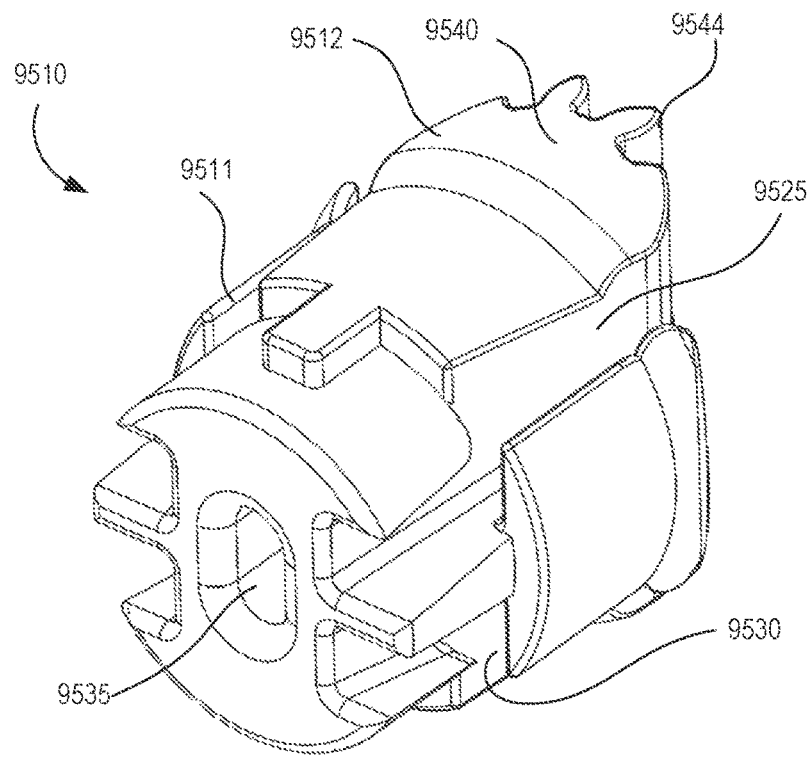
FIG. 50 is a right side perspective view of the first link of a wrist assembly of the instrument shown in FIG. 46.

The wrist assembly 9500 includes a first link 9510, a second link 9610, a first lock ring 9580, and a second lock ring 9690. As shown in FIGS. 49 and 50, the first link 9510 has a proximal end portion 9511 and a distal end portion 9512. The proximal end portion 9511 is coupled to the distal end portion of the shaft 9410. The proximal end portion 9511 can be coupled to the shaft 9410 via any suitable mechanism, as described herein. The distal end portion 9512 includes a joint portion 9540 that is rotatably coupled to a mating joint portion 9640 of the second link 9610. In this manner, the first link 9510 and the second link 9610 form the wrist assembly 9500 having a first axis of rotation $A_1$ (which functions as the pitch axis, the term pitch is arbitrary) about which the second link 9610 rotates relative to the first link 9510. Specifically, the joint portion 9540 includes a series of teeth 9544 that are spaced apart by recesses, and two curved contact surfaces 9545. The series of teeth 9544 intermesh with the series of teeth 9644 (or pins) of the second link 9610, and the curved contact surfaces 9545 are in rolling contact with the corresponding contact surfaces 9645 of the second link 9610.

A first guide channel 9515, a second guide channel 9520, a third guide channel 9525, a fourth guide channel 9530, and a central bore 9535 are defined in the first link 9510. The central bore 9535 can contain (or allow passage of) various components of the wrist assembly, such as, for example, electrical wires. A first proximal end portion 9421 of the first band 9420 is movably disposed within the first guide channel 9515. A second proximal end portion 9431 of the first band 9420 is movably disposed within the second guide channel 9520. A first proximal end portion 9441 of the second band 9440 is movably disposed within the third guide channel 9525. A second proximal end portion 9451 of the second band 9440 is movably disposed within the fourth guide channel 9530. Similar to the guide channels described above for the first link 8510 (and for the instrument 3400), the guide channels 9515, 9520, 9525, 9530 are curved along a longitudinal center line of the first link 9510 (or wrist assembly 9500). Specifically, the inner guide surfaces and the outer guide surfaces that define the guide channels 9515, 9520, 9525, 9530 can have any suitable radius of curvature, and can have different curve shapes, similar to the shapes described above with respect to the instrument 3400. In this manner, when the second link 9610 rotates relative to the first link 9510 about the pitch axis $A_1$ (see the arrow SS in FIG. 46) the respective portions of the first band 9420 and the second band 9440 can contact the curved portions of their respective inner guide surfaces and the outer guide surfaces to maintain the desired bend geometry, band tension, and the like during actuation of the instrument 9400. Moreover, as described above, the guide channels 9515, 9520, 9525, 9530 are offset from the first axis of rotation $A_1$. In this manner, application of a force on the second link 9610 via the first band 9420 or the second band 9440 produces a torque about the first axis of rotation $A_1$.

The first lock ring 9580 is disposed about the first link 9510 and covers the side openings into the guide channels 9515, 9520, 9525, 9530. The first lock ring 9580 can be coupled about the first link 9510 after the portions of the first band 9420 and the second band 9440 have been placed within their respective guide channels. The first lock ring 9580 can be coupled to the first link 9510 by any suitable mechanism (e.g., via an adhesive, an interference fit, a weld or the like).

The second link 9610 has a proximal end portion 9611 and a distal end portion 9612. As described above, the proximal end portion 9611 includes a joint portion 9640 that is rotatably coupled to the joint portion 9540 of the first link 9510. Specifically, the joint portion 9640 includes a series of teeth 9644 that are spaced apart by recesses, and two curved contact surfaces 9645. The series of teeth 9644 intermesh with the series of teeth 9544 (or pins) of the first link 9510, and the curved contact surfaces 9645 are in rolling contact with the corresponding contact surfaces 9545 of the first link 9510. The distal end portion 9612 of the second link 9610 includes a connector that is coupled to the end effector 9460. In this manner, the first tool member 9462 and the second tool member 9482 rotate relative to the second link 9610 about a second axis of rotation) Az. The connector is a pin-type connector and includes the pin 9683 which is supported by (and placed within) the pin openings 9682. As shown in FIG. 46, the second axis of rotation $A_2$ is non-parallel to the pitch axis $A_1$. Thus, the instrument 9400 provides for up to three degrees of freedom (i.e., a pitch motion about the first axis of rotation $A_1$, a yaw rotation about the second axis of rotation $A_2$, and a grip motion about the second axis of rotation $A_2$). As shown in FIG. 47, a pin 9496 is within corresponding guide slots of the first tool member 9462 and the second tool member 9482 to limit the angle through which the first tool member 9462 rotates relative to the second tool member 9482.

Figure 51:
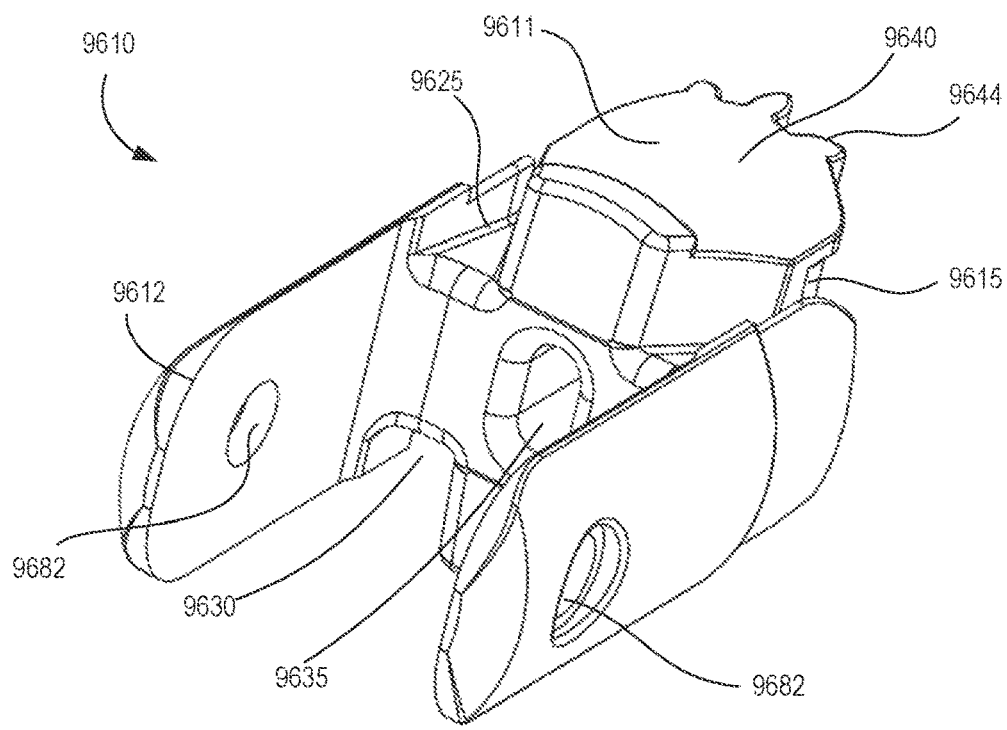
FIG. 51 is a left side perspective view.
Figure 52:
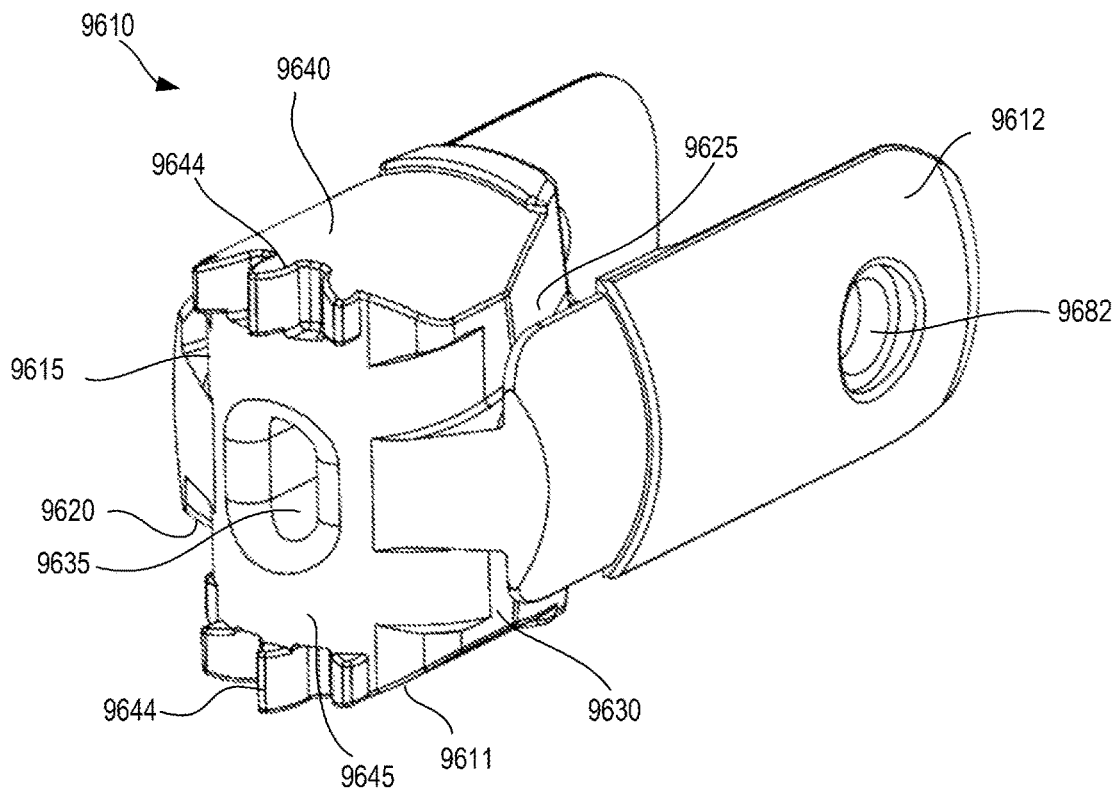
FIG. 52 is a right side perspective view of a second link of the wrist assembly of the instrument shown in FIG. 46.
Figure 53:
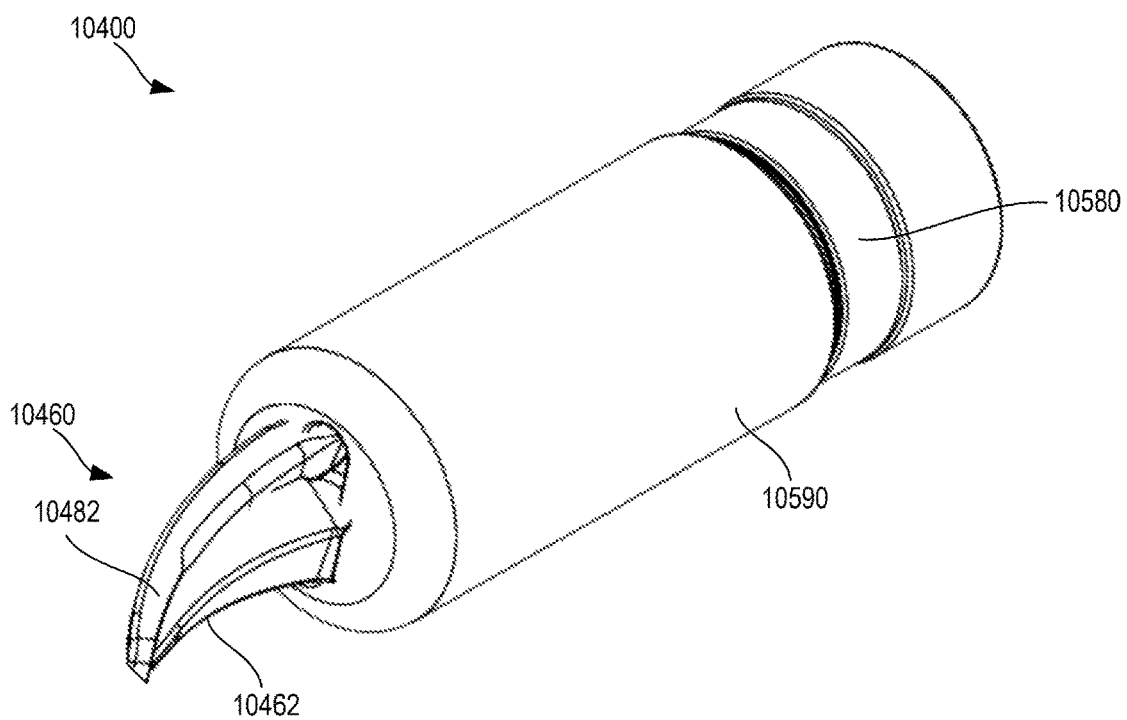
FIG. 53 is a perspective view of a distal end portion of an instrument of a surgery system, according to an embodiment.

Referring to FIGS. 51 and 52, a first guide channel 9615, a second guide channel 9620, a third guide channel 9625, a fourth guide channel 9630, and a central bore 9635 are defined in the second link 9610. The central bore 9635 is aligned with the central bore 9535 and can contain (or allow passage of) various components of the wrist assembly, such as, for example, electrical wires. In this manner, electrical current from the backend assembly can be supplied to the end effector 9460 via components routed through the central bores 9535, 9635. The first guide channel 9615 is aligned with the first guide channel 9515 (of the first link 9510), and the second guide channel 9620 is aligned with the second guide channel 9520 (of the first link 9510). In this manner, a portion (e.g., the first proximal portion 9421) of the first band 9420 is routed from the shaft 9410 and through the first guide channel 9515 and the first guide channel 9615 to be coupled to the first tool member 9462. A portion (e.g., a second portion 9431) of the first band 9420 is routed from the first tool member 9462 and back through the second guide channel 9520 and the second guide channel 9620 to be returned to the backend mechanism (via the shaft). The third guide channel 9625 is aligned with the third guide channel 9525 (of the first link 9510), and the fourth guide channel 9630 is aligned with the fourth guide channel 9530 (of the first link 9510). In this manner, a portion (e.g., the first proximal portion 9441) of the second band 9440 is routed from the shaft 9410 and through the third guide channel 9525 and the third guide channel 9625 to be coupled to the second tool member 9482. A portion (e.g., a second portion 9451) of the second band 9440 is routed from the second tool member 9482 and back through the fourth guide channel 9530 and the fourth guide channel 9630 to be returned to the backend mechanism (via the shaft).

Similar to the guide channels described above for the second link 8610 (and for the instrument 3400), the guide channels 9615, 9620, 9625, 9630 are curved along a longitudinal center line of the second link 9610 (or wrist assembly 9500). Specifically, the inner guide surfaces and the outer guide surfaces that define the guide channels 9615, 9620, 9625, 9630 can have any suitable radius of curvature, and can have different curve shapes, similar to the shapes described above with respect to the instrument 3400. In this manner, when the second link 9610 rotates relative to the first link 9510 about the pitch axis $A_1$ (see the arrow SS in FIG. 46) the respective portions of the first band 9420 and the second band 9440 can contact the curved portions of their respective inner guide surfaces and the outer guide surfaces to maintain the desired bend geometry, band tension, and the like during actuation of the instrument 9400. Moreover, as described above, the guide channels 9615, 9620, 9625, 9630 are offset from the first axis of rotation $A_1$. In this manner, application of a force on the second link 9610 via the first band 9420 or the second band 9440 produces a torque about the first axis of rotation $A_1$.

The second lock ring 9690 is disposed about the second link 9610 and covers the side openings into the guide channels 9615, 9620, 9625, 9630. The second lock ring 9690 can be coupled about the second link 9610 after the portions of the first band 9420 and the second band 9440 have been placed within their respective guide channels. The second lock ring 9690 can be coupled to the second link 9610 by any suitable mechanism (e.g., via an adhesive, an interference fit, a weld or the like).

The end effector 9460 includes a first tool member 9462, a second tool member 9482, and an insulator 9495. The first tool member 9462 includes a contact portion 9464 and a pulley portion 9467. The contact portion 9464 is configured engage or manipulate or cut a target tissue during a surgical procedure. The pulley portion 9467 includes a guide surface 9470, a central opening 9468, and a connection slot (similar to one of the connection slots 8469). The guide surface 9470 is within a channel and is the surface about which the distal end portion 9422 of the first band 9420 is wrapped. The distal end portion 9422 of the first band 9420 includes a connection tab (similar to one of the connection tabs 8424) that are coupled within the corresponding connection slots of the pulley portion 9487. The pulley portion 9467 is rotatably coupled to the second link 9610 via the pin 9683, which is disposed within the central opening 9468. In this manner, the first tool member 9462 rotates about the pin 9683 and relative to the second link 9610 via the second axis of rotation $A_2$, as shown by the arrow TT in FIG. 46. Moreover, the guide surface 9470 is offset from the yaw axis $A_2$ (i.e., by the radius of the guide surface 9470). In this manner, application of a force by the first band 9420 on the pulley portion 9467 produces a torque on the first tool member 9462 about the yaw axis $A_2$, which results in rotation of the first tool member 9462 or the application of a gripping force.

The second tool member 9482 includes a contact portion 9484 and a pulley portion 9487. The contact portion 9484 is configured engage or manipulate or cut a target tissue during a surgical procedure. The pulley portion 9487 includes a guide surface 9490, a central opening 9488, and a connection slot (not identified, but similar to one of the connection slots 8469). The guide surface 9490 is within a channel and is the surface about which the distal end portion 9442 of the second band 9440 is wrapped. The second band 9440 is coupled to the guide surface 9490 by a connection tab (similar to one of the tabs 8424) that are coupled within a corresponding connection slot. The pulley portion 9487 is rotatably coupled to the second link 9610 via the pin 9683, which is disposed within the central opening 9488. In this manner, the second tool member 9482 rotates about the pin 9683 and relative to the second link 9610 via the yaw $A_2$, as shown by the arrow TT in FIG. 46. Moreover, the guide surface 9490 is offset from the yaw axis $A_2$ (i.e., by the radius of the guide surface 9490). In this manner, application of a force by the second band 9440 on the pulley portion 9487 produces a torque on the second tool member 9482 about the yaw axis $A_2$, which results in rotation of the second tool member 9482 or the application of a gripping force.

The first band 9420 has a first proximal end portion 9421, a second proximal end portion 9431, a distal end portion 9422, a first central portion 9423, and a second central portion 9433. As shown, the distal end portion 9422 is wrapped about and coupled to the pulley portion 9467 of the first tool member 9462. The first proximal end portion 9421 and the second proximal end portion 9431 each extend through the first link 9510 (i.e., the first guide channel 9515 and the second guide channel 9520, respectively) and into the shaft 9410. Additionally, the first proximal end portion 9421 and the second proximal end portion 9431 each extend through the shaft 9410 and are coupled to a backend mechanism (not shown, but similar to the actuator 7700 described above) that can move each of the proximal end portions to produce pitch, yaw, and gripping movements of the wrist assembly 9500. The first central portion 9423 is between the first proximal end portion 9421 and the distal end portion 9422, and the second central portion 9433 is between the second proximal end portion 9431 and the distal end portion 9422. As shown, the first band 9420 is twisted along its longitudinal center line in two places: the first region of twist is along the first central portion 9423 and the second region of twist is along the second central portion 9433. In this manner, the orientation of the contact surfaces of the first band 9420 at the first proximal end portion 9421 and the second proximal end portion 9431 (i.e., the band surfaces that contact or are wrapped about the inner and outer guide surfaces) are different than an orientation of the contact surface of the first band 9420 at the distal end portion 9422 (i.e., the band surface that is wrapped about the contact surface 9470).

The second band 9440 has a first proximal end portion 9441, a second proximal end portion 9451, a distal end portion 9442, a first central portion 9443, and a second central portion 9453. As shown, the distal end portion 9442 is wrapped about and coupled to the pulley portion 9487 of the second tool member 9482. The first proximal end portion 9441 and the second proximal end portion 9451 each extend through the first link 9510 (i.e., the third guide channel 9525 and the fourth guide channel 9530, respectively) and into the shaft 9410. Additionally, the first proximal end portion 9441 and the second proximal end portion 9451 each extend through the shaft 9410 and are coupled to a backend mechanism (not shown, but similar to the actuator 7700 described above) that can move each of the proximal end portions to produce pitch, yaw, and gripping movements of the wrist assembly 9500. The first central portion 9443 is between the first proximal end portion 9441 and the distal end portion 9442, and the second central portion 9453 is between the second proximal end portion 9451 and the distal end portion 9442. As shown, the second band 9440 is twisted along its longitudinal center line in two places: the first region of twist is along the first central portion 9443 and the second region of twist is along the second central portion 9453. In this manner, the orientation of the contact surfaces of the second band 9440 at the first proximal end portion 9441 and the second proximal end portion 9451 (i.e., the band surfaces that contact or are wrapped about the inner and outer guide surfaces) are different than an orientation of the contact surface of the second band 9440 at the distal end portion 9442 (i.e., the band surface that is wrapped about the contact surface 9490).

Figure 54:
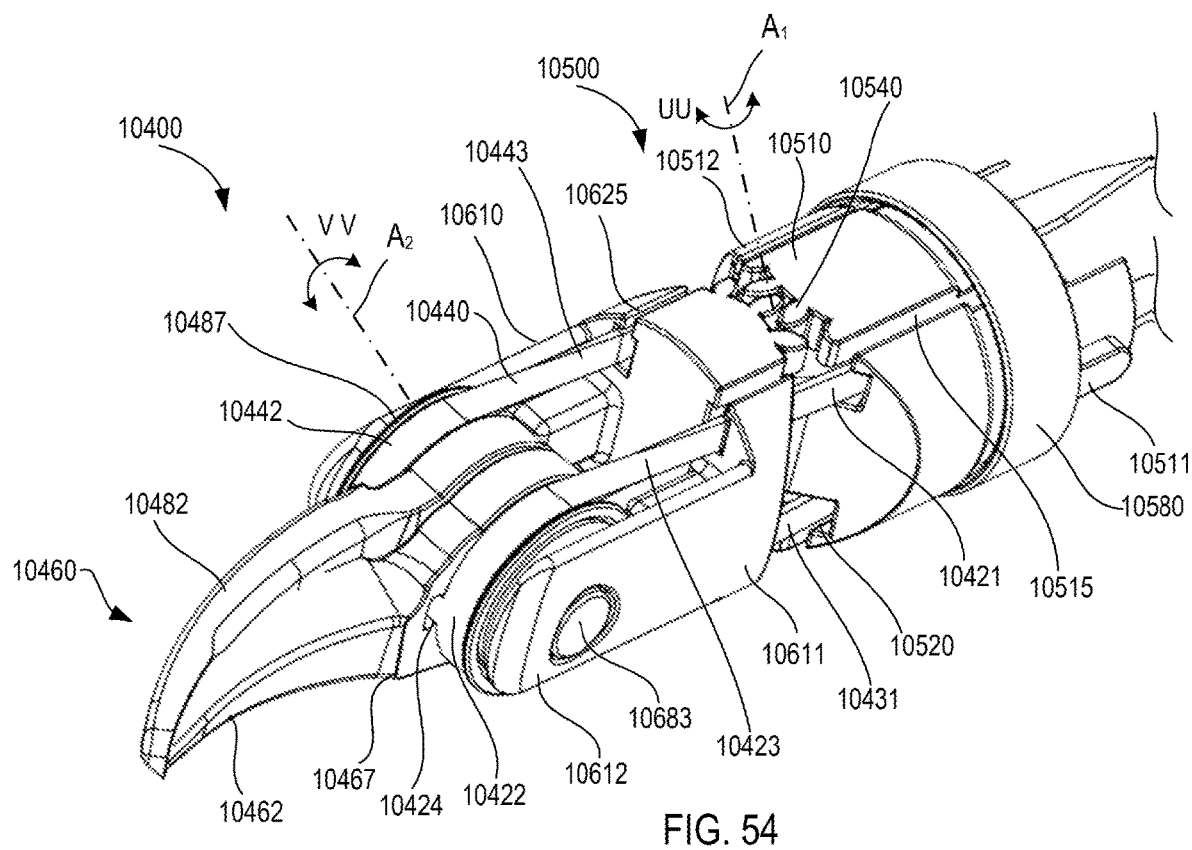
FIG. 54 is a perspective view of the distal end portion of the instrument shown in FIG. 53 with the cover removed to show the components of the instrument shown in FIG. 53.
Figure 55:
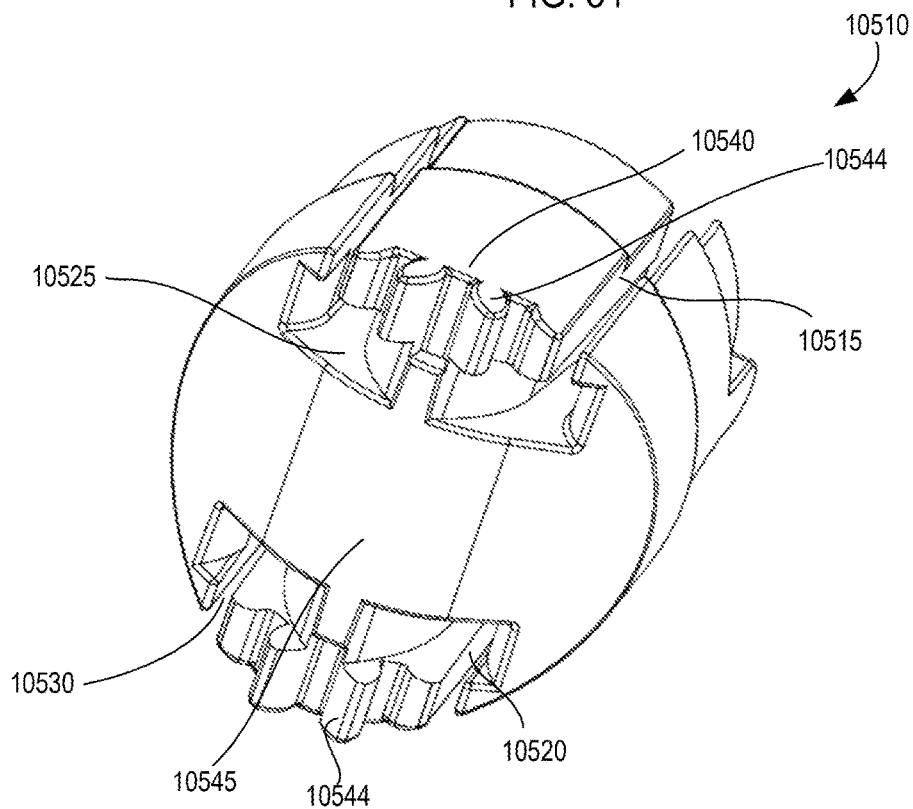
FIG. 55 is a left side perspective view of a first link of a wrist assembly of the instrument shown in FIG. 54.
Figure 56:
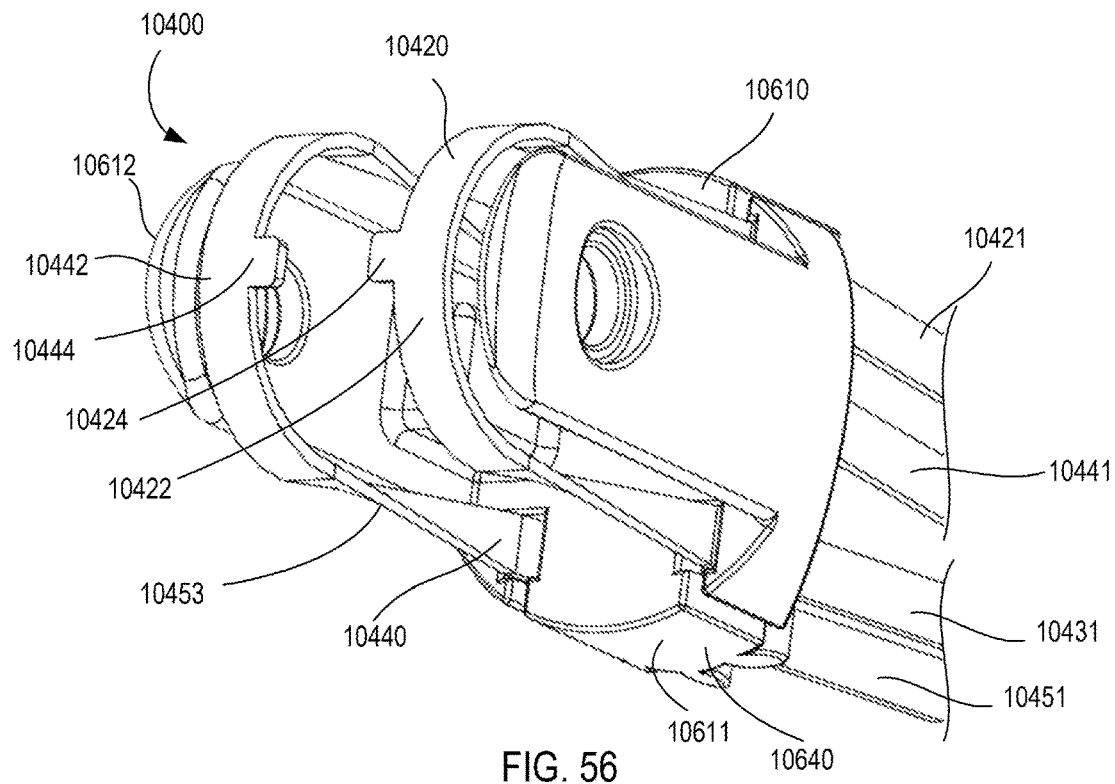
FIG. 56 is a perspective view of a portion of the bands and a second link of the instrument shown in FIG. 54.

FIGS. 53-57 are various views of a portion of an instrument 10400, according to an embodiment. In some embodiments, the instrument 10400 or any of the components therein are optionally parts of a surgical system that performs surgical procedures, and which can include a manipulator unit, a series of kinematic linkages, a series of cannulas, or the like. The instrument 10400 (and any of the instruments described herein) can be used in any suitable surgical system, such as the MIRS system 1000 shown and described above. The instrument 10400 includes an actuator assembly (not shown, but similar to the actuator 7700), a shaft (not shown), a wrist assembly 10500, a cover 10590, and an end effector 10460. Referring to FIGS. 54 and 56, the instrument 10400 also includes a first band 10420 and a second band 10440 that couple the backend mechanism to the wrist assembly 10500. The instrument 10400 is configured such that movement of the bands produces rotation of the wrist assembly 10500 (i.e., pitch rotation) about a first axis of rotation $A_1$ (see FIG. 54, which functions as the pitch axis, the term pitch is arbitrary), yaw rotation of the end effector 10460 about a second axis of rotation $A_2$ (see FIG. 54, which functions as the yaw axis), grip rotation of the tool members of the end effector 10460 about the yaw axis, or any combination of these movements. Changing the pitch, yaw, or grip of the instrument 10400 can be performed by manipulating the bands in similar manner as that described above for the instrument 6400. Thus, the specific movement of various portions of the first band 10420 and the second band 10440 to accomplish the desired motion is not described below.

The wrist assembly 10500 includes a first link 10510, a second link 10610, and a first lock ring 10580. As shown in FIGS. 54 and 55, the first link 10510 has a proximal end portion 10511 and a distal end portion 10512. The proximal end portion 10511 is coupled to the distal end portion of the shaft. The proximal end portion 10511 can be coupled to the shaft via any suitable mechanism, as described herein. The distal end portion 10512 includes a joint portion 10540 that is rotatably coupled to a mating joint portion 10640 of the second link 10610. In this manner, the first link 10510 and the second link 10610 form the wrist assembly 10500 having a first axis of rotation $A_1$ about which the second link 10610 rotates relative to the first link 10510. Specifically, the joint portion 10540 includes a series of teeth 10544 that are spaced apart by recesses, and a curved contact surface 10545. The series of teeth 10544 intermesh with the series of teeth 10644 (or pins) of the second link 10610, and the curved contact surface 10545 is in rolling contact with the corresponding contact surface 10645 of the second link 10610.

A first guide channel 10515, a second guide channel 10520, a third guide channel 10525, and a fourth guide channel 10530 are defined in the first link 10510. Unlike the first link 9510, the first link 10510 does not define a central bore. A first proximal end portion 10421 of the first band 10420 is movably disposed within the first guide channel 10515. A second proximal end portion 10431 of the first band 10420 is movably disposed within the second guide channel 10520. A first proximal end portion 10441 of the second band 10440 is movably disposed within the third guide channel 10525. A second proximal end portion 10451 of the second band 10440 is movably disposed within the fourth guide channel 10530. Similar to the guide channels described above for the first link 8510 (and for the instrument 3400), the guide channels 10515, 10520, 10525, 10530 are curved along a longitudinal center line of the first link 10510 (or wrist assembly 10500). Specifically, the inner guide surfaces and the outer guide surfaces that define the guide channels 10515, 10520, 10525, 10530 can have any suitable radius of curvature, and can have different curve shapes, similar to the shapes described above with respect to the instrument 3400. In this manner, when the second link 10610 rotates relative to the first link 10510 about the pitch axis $A_1$ (see the arrow UU in FIG. 54) the respective portions of the first band 10420 and the second band 10440 can contact the curved portions of their respective inner guide surfaces and the outer guide surfaces to maintain the desired bend geometry, band tension, and the like during actuation of the instrument 10400. In particular, the inner guide surfaces of the first link 10510 have a smaller radius of curvature (i.e., are more sharply curved) than the corresponding inner guide surfaces of the first link 9510. Moreover, as described above, the guide channels 10515, 10520, 10525, 10530 are offset from the first axis of rotation $A_1$. In this manner, application of a force on the second link 10610 via the first band 10420 or the second band 10440 produces a torque about the first axis of rotation $A_1$.

The first lock ring 10580 is disposed about the first link 10510 and covers the side openings into the guide channels 10515, 10520, 10525, 10530. The first lock ring 10580 can be coupled about the first link 10510 after the portions of the first band 10420 and the second band 10440 have been placed within their respective guide channels. The first lock ring 10580 can be coupled to the first link 10510 by any suitable mechanism (e.g., via an adhesive, an interference fit, a weld or the like).

Figure 57:
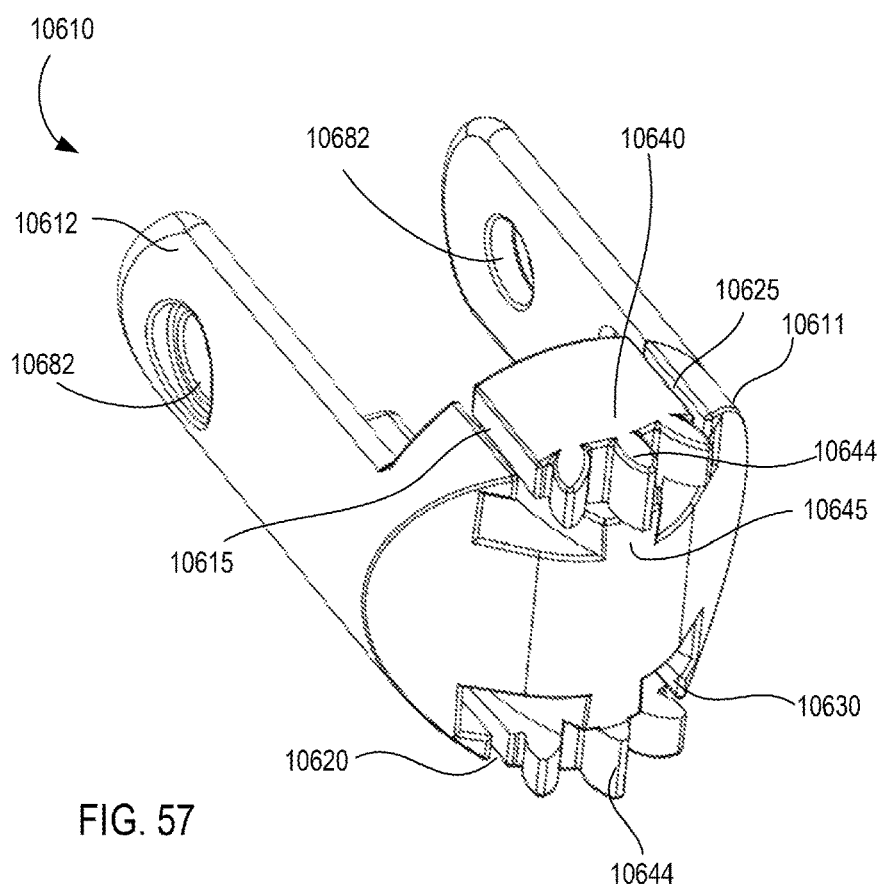
FIG. 57 is a perspective view of the second link of the wrist assembly of the instrument shown in FIG. 54.
Figure 58:
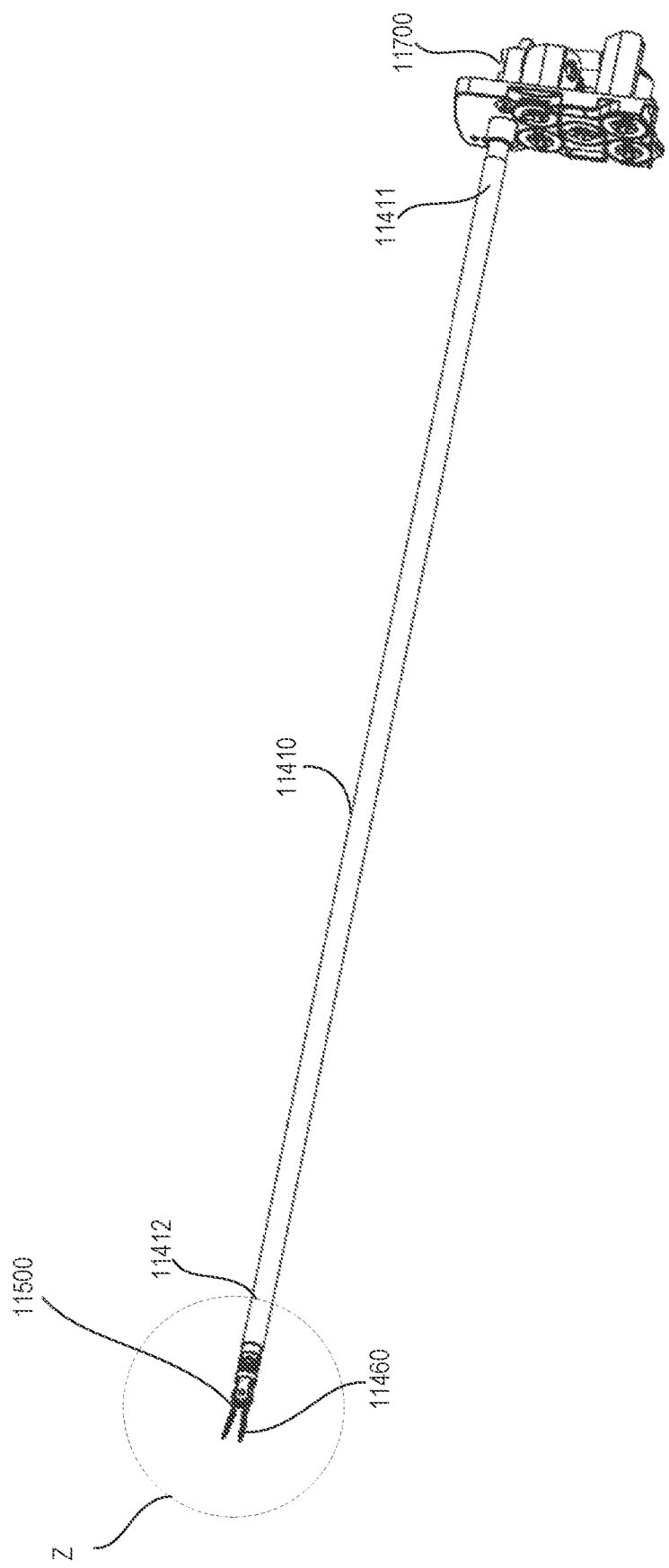
FIG. 58 is a perspective view of an instrument of a surgery system, according to an embodiment.

Referring to FIG. 57, the second link 10610 has a proximal end portion 10611 and a distal end portion 10612. As described above, the proximal end portion 10611 includes a joint portion 10640 that is rotatably coupled to the joint portion 10540 of the first link 10510. Specifically, the joint portion 10640 includes a series of teeth 10644 that are spaced apart by recesses, and a curved contact surface 10645. The series of teeth 10644 intermesh with the series of teeth 10544 (or pins) of the first link 10510, and the curved contact surface 10645 are in rolling contact with the corresponding contact surface 10545 of the first link 10510. The distal end portion 10612 of the second link 10610 includes a connector that is coupled to the end effector 10460. In this manner, the first tool member 10462 and the second tool member 10482 rotate relative to the second link 10610 about a second axis of rotation $A_2$. The connector is a pin-type connector and includes the pin 10683 which is supported by (and placed within) the pin openings 10682. As shown in FIG. 54, the second axis of rotation $A_2$ is non-parallel to the pitch axis $A_1$. Thus, the instrument 10400 provides for up to three degrees of freedom (i.e., a pitch motion about the first axis of rotation $A_1$, a yaw rotation about the second axis of rotation $A_2$, and a grip motion about the second axis of rotation $A_2$).

A first guide channel 10615, a second guide channel 10620, a third guide channel 10625, and a fourth guide channel 10630 are defined in the second link 10610. Unlike the second link 9610, the second link 10610 does not define a central bore. The first guide channel 10615 is aligned with the first guide channel 10515 (of the first link 10510), and the second guide channel 10620 is aligned with the second guide channel 10520 (of the first link 10510). In this manner, a portion (e.g., the first proximal portion 10421) of the first band 10420 is routed from the shaft and through the first guide channel 10515 and the first guide channel 10615 to be coupled to the first tool member 10462. A portion (e.g., a second portion 10431) of the first band 10420 is routed from the first tool member 10462 and back through the second guide channel 10520 and the second guide channel 10620 to be returned to the backend mechanism (via the shaft). The third guide channel 10625 is aligned with the third guide channel 10525 (of the first link 10510), and the fourth guide channel 10630 is aligned with the fourth guide channel 10530 (of the first link 10510). In this manner, a portion (e.g., the first proximal portion 10441) of the second band 10440 is routed from the shaft and through the third guide channel 10525 and the third guide channel 10625 to be coupled to the second tool member 10482. A portion (e.g., a second portion 10451) of the second band 10440 is routed from the second tool member 10482 and back through the fourth guide channel 10530 and the fourth guide channel 10630 to be returned to the backend mechanism (via the shaft).

Similar to the guide channels described above for the second link 8610 (and for the instrument 3400), the guide channels 10615, 10620, 10625, 10630 are curved along a longitudinal center line of the second link 10610 (or wrist assembly 10500). Specifically, the inner guide surfaces and the outer guide surfaces that define the guide channels 10615, 10620, 10625, 10630 can have any suitable radius of curvature, and can have different curve shapes, similar to the shapes described above with respect to the instrument 3400. In this manner, when the second link 10610 rotates relative to the first link 10510 about the pitch axis $A_1$ (see the arrow SS in FIG. 46) the respective portions of the first band 10420 and the second band 10440 can contact the curved portions of their respective inner guide surfaces and the outer guide surfaces to maintain the desired bend geometry, band tension, and the like during actuation of the instrument 10400. In particular, the outer guide surfaces of the second link 10610 have a smaller radius of curvature (i.e., are more sharply curved) than the corresponding outer guide surfaces of the second link 9610. Moreover, as described above, the guide channels 10615, 10620, 10625, 10630 are offset from the first axis of rotation $A_1$. In this manner, application of a force on the second link 10610 via the first band 10420 or the second band 10440 produces a torque about the first axis of rotation $A_1$.

The end effector 10460 includes a first tool member 10462 and a second tool member 10482. The first tool member 10462 includes a contact portion (not identified) and a pulley portion 10467. The contact portion and the pulley portion 10467 are similar to the contact portion 9464 and the pulley portion 9467, respectively, and are therefore not described in detail herein. The second tool member 10482 includes a contact portion (not identified) and a pulley portion 10487. The contact portion and the pulley portion 10487 are similar to the contact portion 9484 and the pulley portion 9487, respectively, and are therefore not described in detail herein. The pulley portions 10467, 10487 are each rotatably coupled to the second link 10610 via the pin 10683. In this manner, the first tool member 10462 and the second tool member 10482 can each rotate about the pin 10683 and relative to the second link 10610 about the second axis of rotation $A_2$, as shown by the arrow VV in FIG. 54.

The first band 10420 has a first proximal end portion 10421, a second proximal end portion 10431, a distal end portion 10422, a first central portion 10423, and a second central portion (not shown). As shown, the distal end portion 10422 is wrapped about and coupled to the pulley portion 10467 of the first tool member 10462 via the tab 10424. The first proximal end portion 10421 and the second proximal end portion 10431 each extend through the first link 10510 (i.e., the first guide channel 10515 and the second guide channel 10520, respectively) and into the shaft. Additionally, the first proximal end portion 10421 and the second proximal end portion 10431 each extend through the shaft and are coupled to a backend mechanism (not shown, but similar to the actuator 7700 described above) that can move each of the proximal end portions to produce pitch, yaw, and gripping movements of the wrist assembly 10500. The first central portion 10423 is between the first proximal end portion 10421 and the distal end portion 10422, and the second central portion is between the second proximal end portion 10431 and the distal end portion 10422. As shown, the first band 10420 is twisted along its longitudinal center line in two places: the first region of twist is along the first central portion 10423 and the second region of twist is along the second central portion (not shown, but opposite the first central portion 10423). In this manner, the orientation of the contact surfaces of the first band 10420 at the first proximal end portion 10421 and the second proximal end portion 10431 (i.e., the band surfaces that contact or are wrapped about the inner and outer guide surfaces) are different than an orientation of the contact surface of the first band 10420 at the distal end portion 10422 (i.e., the band surface that is wrapped about pulley portion 10467).

The second band 10440 has a first proximal end portion 10441, a second proximal end portion 10451, a distal end portion 10442, a first central portion 10443, and a second central portion 10453. As shown, the distal end portion 10442 is wrapped about and coupled to the pulley portion 10487 of the second tool member 10482 by the tab 10444. The first proximal end portion 10441 and the second proximal end portion 10451 each extend through the first link 10510 (i.e., the first guide channel 10525 and the second guide channel 10530, respectively) and into the shaft. Additionally, the first proximal end portion 10441 and the second proximal end portion 10451 each extend through the shaft and are coupled to a backend mechanism (not shown, but similar to the actuator 7700 described above) that can move each of the proximal end portions to produce pitch, yaw, and gripping movements of the wrist assembly 10500. The first central portion 10443 is between the first proximal end portion 10421 and the distal end portion 10442, and the second central portion 10453 is between the second proximal end portion 10451 and the distal end portion 10442. As shown, the second band 10440 is twisted along its longitudinal center line in two places: the first region of twist is along the first central portion 10443 and the second region of twist is along the second central portion. In this manner, the orientation of the contact surfaces of the second band 10440 at the first proximal end portion 10441 and the second proximal end portion 10451 (i.e., the band surfaces that contact or are wrapped about the inner and outer guide surfaces) are different than an orientation of the contact surface of the second band 10440 at the distal end portion 10442 (i.e., the band surface that is wrapped about the pulley portion 10487).

In some embodiments, any of the end effectors described herein can be a cauterizing tool that can manipulate or cut, and then cauterize tissue. Accordingly, in some embodiments any of the instruments described herein can include any number of wires, insulators, or the like, and can define any suitable channels to accommodate these electrical components. In such embodiments, the use of bands, which can be thinner in a width dimension that cables, can allow the size of wrist components (e.g., a first link or a second link) to be minimized. For example, FIGS. 58-63 are various views of an instrument 11400, according to an embodiment. In some embodiments, the instrument 11400 or any of the components therein are optionally parts of a surgical system that performs surgical procedures, and which can include a manipulator unit, a series of kinematic linkages, a series of cannulas, or the like. The instrument 11400 (and any of the instruments described herein) can be used in any suitable surgical system, such as the MIRS system 1000 shown and described above. The instrument 11400 includes an actuator assembly 11700, a shaft 11410, a wrist assembly 11500, and an end effector 11460. Referring to FIG. 63, the instrument 11400 also includes a first band 11420 and a second band 11440 that couple the backend mechanism 11700 to the wrist assembly 11500. The instrument 11400 is configured such that movement of the bands produces rotation of the wrist assembly 11500 (i.e., pitch rotation) about a first axis of rotation $A_1$ (see FIG. 59, which functions as the pitch axis, the term pitch is arbitrary), yaw rotation of the end effector 11460 about a second axis of rotation $A_2$ (see FIG. 59, which functions as the yaw axis), grip rotation of the tool members of the end effector 11460 about the yaw axis, or any combination of these movements. Changing the pitch, yaw, or grip of the instrument 11400 can be performed by manipulating the bands in similar manner as that described above for the instrument 6400. Thus, the specific movement of various portions of the first band 11420 and the second band 11440 to accomplish the desired motion is not described below.

In some embodiments, the backend mechanism 11700 can include one or more linear actuators that produce translation (linear motion) of a portion of the bands. Such backend mechanisms can include, for example, a gimbal, a lever, or any other suitable mechanism to directly pull (or release) an end portion of any of the bands. For example, in some embodiments, the backend mechanism 11700 can include any of the backend assemblies or components described in U.S. Patent Application Pub. No. US 20157/0047454 A1 (filed Aug. 15, 2014), entitled "Lever Actuated Gimbal Plate," or U.S. Pat. No. 6,817,974 B2 (filed Jun. 28, 2001), entitled "Surgical Tool Having Positively Positionable Tendon-Actuated Multi-Disk Wrist Joint," each of which is incorporated herein by reference in its entirety. In other embodiments, however, the backend mechanism 11700 can include a capstan or other motor-driven roller that rotates or "winds" a portion of any of the bands to produce the desired band movement. For example, in some embodiments, the backend mechanism 11700 can include any of the backend assemblies or components described in U.S. Pat. No. 9,204,923 B2 (filed Jul. 16, 2008), entitled "Medical Instrument Electronically Energized Using Drive Cables," which is incorporated herein by reference in its entirety.

The shaft 11410 can be any suitable elongated shaft that couples the wrist assembly 11500 to the backend mechanism 11700. Specifically, the shaft 11410 includes a proximal end portion 11411 that is coupled to a housing of the backend mechanism 11700, and a distal end portion 11412 that is coupled to the wrist assembly 11500. The shaft 11410 defines a passageway or series of passageways through which the bands and other components (e.g., electrical wires 11401, 11405, ground wires, or the like) can be routed from the backend mechanism 11700 to the wrist assembly 11500. Although shown as being cylindrical, in other embodiments, the shaft 11410 can have any suitable shape.

Figure 60:
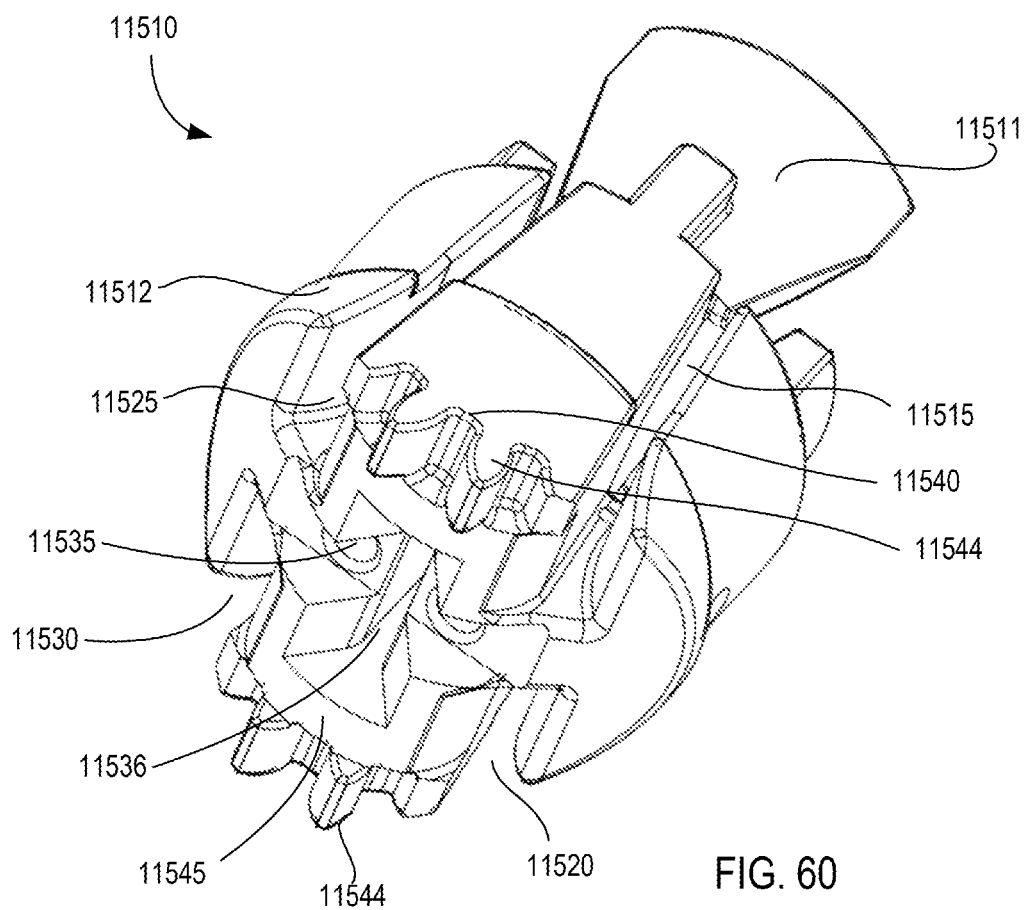
FIG. 60 is a perspective view of a first link of a wrist assembly of the instrument shown in FIG. 59.

The wrist assembly 11500 includes a first link 11510 and a second link 11610. As shown in FIG. 60, the first link 11510 has a proximal end portion 11511 and a distal end portion 11512. The proximal end portion 11511 is coupled to the distal end portion of the shaft 11410. The proximal end portion 11511 can be coupled to the shaft 11410 via any suitable mechanism, as described herein. The distal end portion 11512 includes a joint portion 11540 that is rotatably coupled to a mating joint portion 11640 of the second link 11610. In this manner, the first link 11510 and the second link 11610 form the wrist assembly 11500 having a first axis of rotation $A_1$ about which the second link 11610 rotates relative to the first link 11510. Specifically, the joint portion 11540 includes a series of teeth 11544 that are spaced apart by recesses, and a two curved contact surfaces 11545. The series of teeth 11544 intermesh with the series of teeth 11644 (or pins) of the second link 11610, and the curved contact surfaces 11545 is in rolling contact with the corresponding contact surfaces 11645 of the second link 11610.

The first link 11510 defines two central bores 11535 and a central slot 11536. The central bores 11535 contain (or allow passage of) the electrical wires 11401, 11405. The central slot 11536 contains a portion of a retention strip (not shown) that is coupled to the insulator 11495. The retention strip retains the second link 11610 to the first link 11510 when tension within the bands is reduced, or during assembly before the bands are secured. The first link 11510 also defines a first guide channel 11515, a second guide channel 11520, a third guide channel 11525, and a fourth guide channel 11535. A first proximal end portion 11421 of the first band 11420 is movably disposed within the first guide channel 11515. A second proximal end portion 11431 of the first band 11420 is movably disposed within the second guide channel 11520. A first proximal end portion 11441 of the second band 11440 is movably disposed within the third guide channel 11525. A second proximal end portion 11451 of the second band 11440 is movably disposed within the fourth guide channel 11530. Similar to the guide channels described above for the first link 8510 (and for the instrument 3400), the guide channels 11515, 11520, 11525, 11530 are curved along a longitudinal center line of the first link 11510 (or wrist assembly 11500). Specifically, the inner guide surfaces and the outer guide surfaces that define the guide channels 11515, 11520, 11525, 11530 can have any suitable radius of curvature, and can have different curve shapes, similar to the shapes described above with respect to the instrument 3400. In this manner, when the second link 11610 rotates relative to the first link 11510 about the pitch axis $A_1$ (see the arrow WW in FIG. 59) the respective portions of the first band 11420 and the second band 11440 can contact the curved portions of their respective inner guide surfaces and the outer guide surfaces to maintain the desired bend geometry, band tension, and the like during actuation of the instrument 11400. Moreover, as described above, the guide channels 11515, 11520, 11525, 11530 are offset from the first axis of rotation $A_1$. In this manner, application of a force on the second link 11610 via the first band 11420 or the second band 11440 produces a torque about the first axis of rotation $A_1$.

Figure 59:
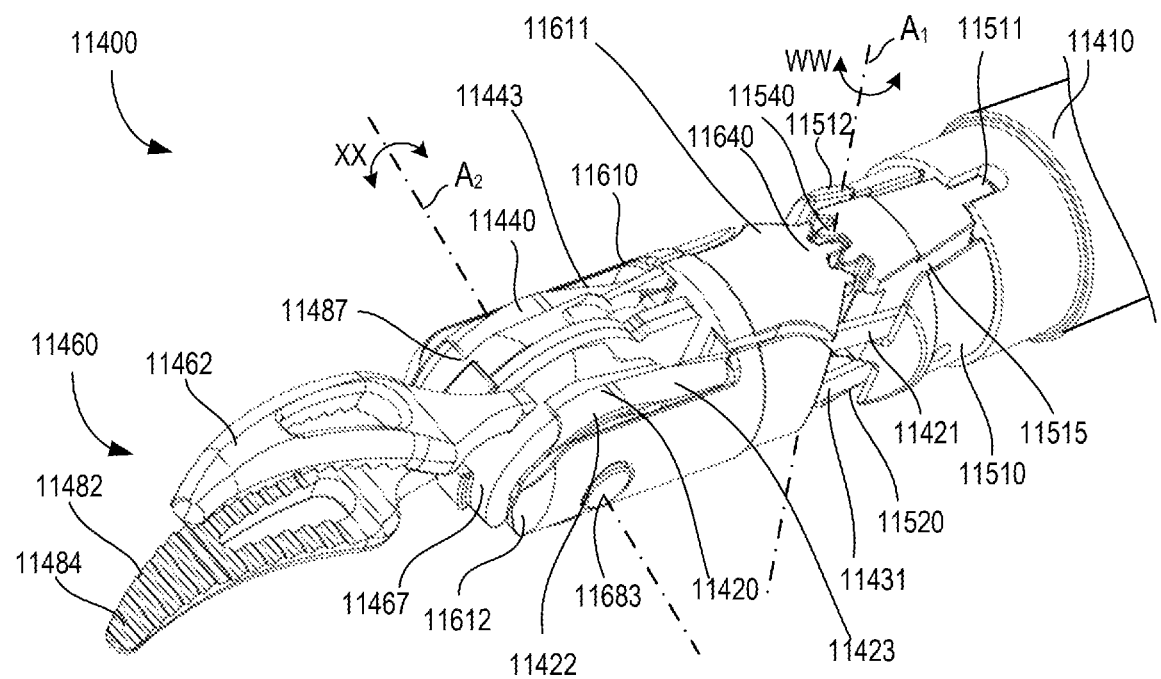
FIG. 59 is an enlarged perspective view of a distal end portion of the instrument indicated by the region Z shown in FIG. 58.
Figure 61:
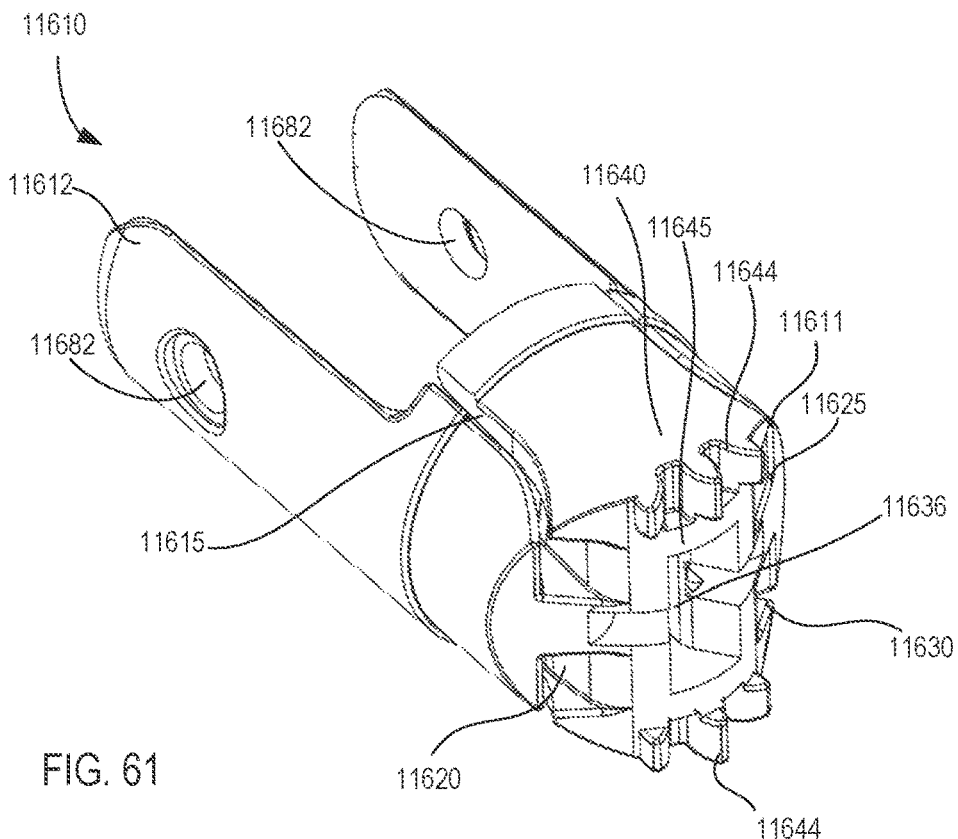
FIGS. 61 and 62 are perspective views of a second link of the wrist assembly of the instrument shown in FIG. 59.
Figure 62:
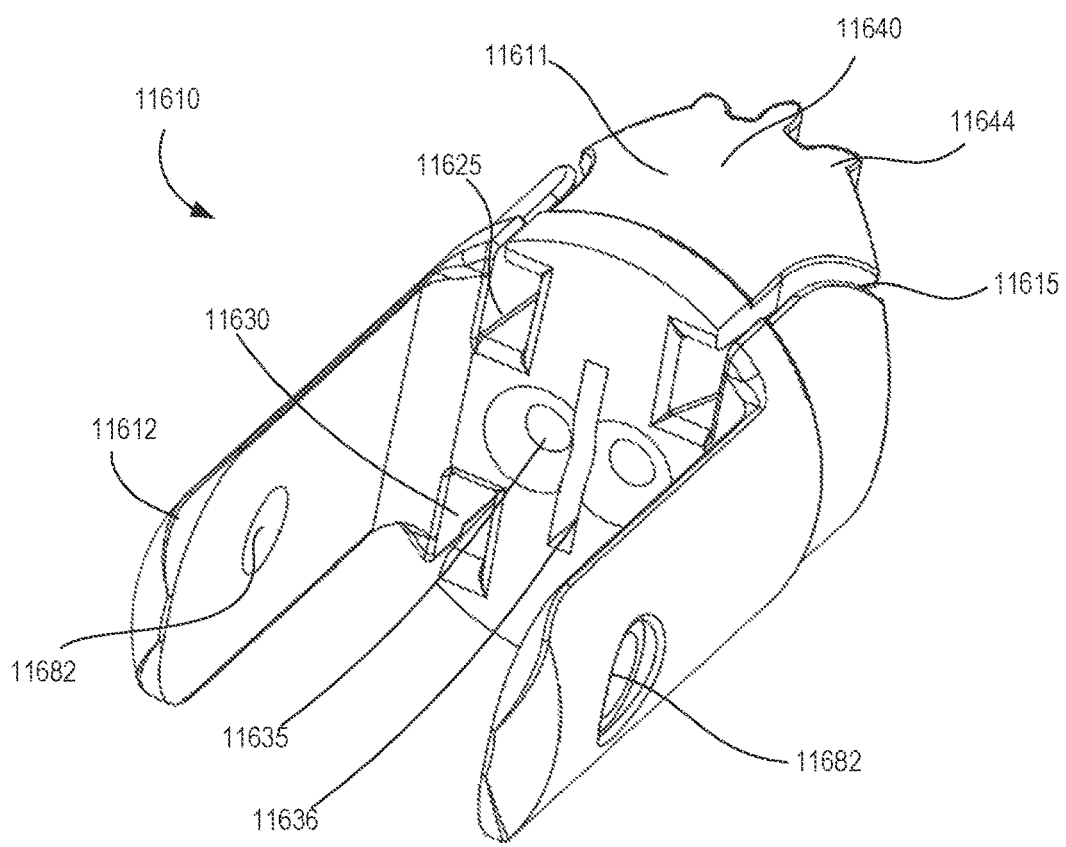
Figure 63:
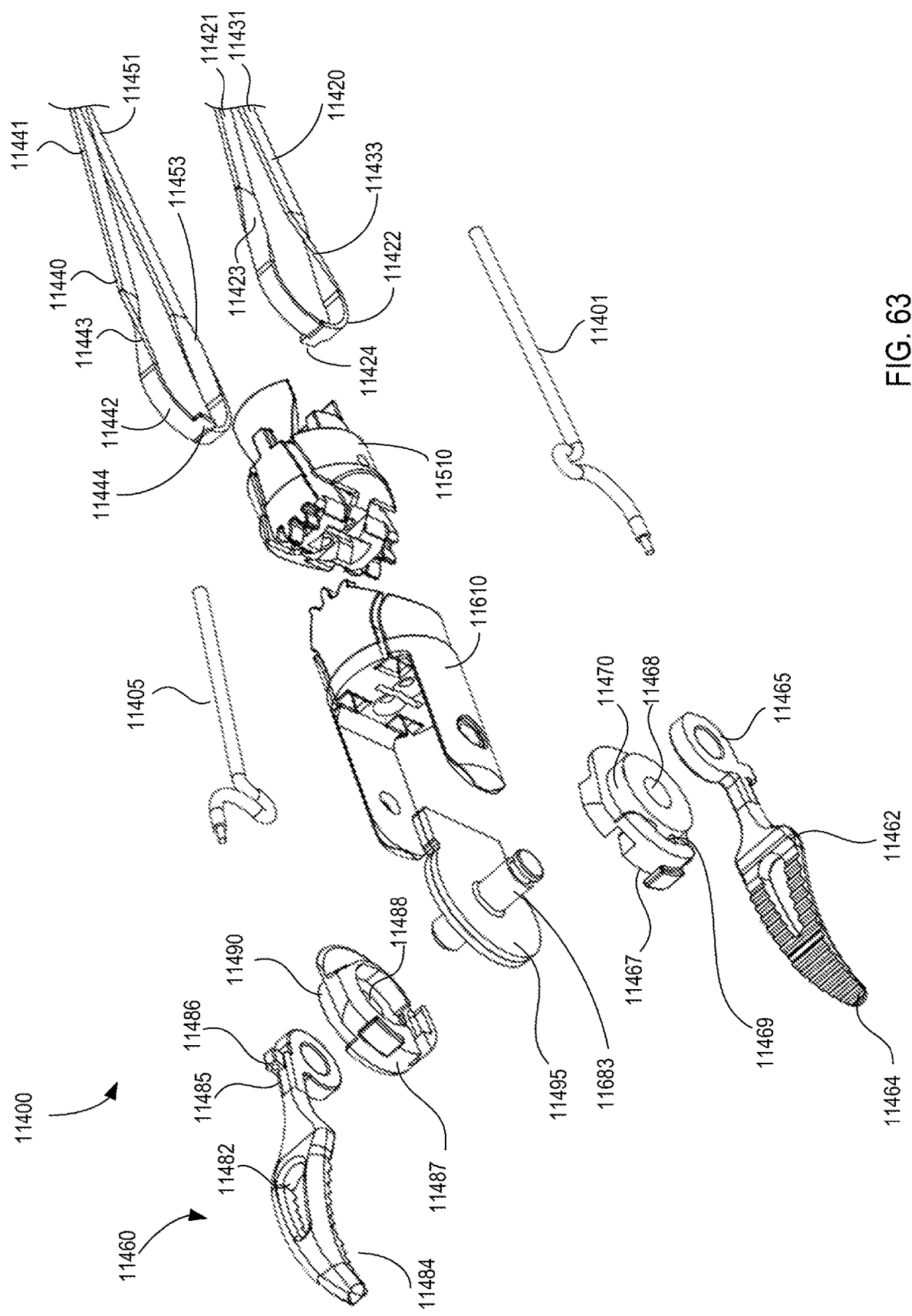
FIG. 63 is an exploded perspective view of the distal end portion of the instrument shown in FIG. 59.

Referring to FIGS. 61 and 62, the second link 11610 has a proximal end portion 11611 and a distal end portion 11612. As described above, the proximal end portion 11611 includes a joint portion 11640 that is rotatably coupled to the joint portion 11540 of the first link 11510. Specifically, the joint portion 11640 includes a series of teeth 11644 that are spaced apart by recesses, and two curved contact surfaces 11645. The series of teeth 11644 intermesh with the series of teeth 11544 (or pins) of the first link 11510, and the curved contact surfaces 11645 are in rolling contact with the corresponding contact surfaces 11545 of the first link 11510. The distal end portion 11612 of the second link 11610 includes a connector that is coupled to the end effector 11460. In this manner, the first tool member 11462 and the second tool member 11482 rotate relative to the second link 11610 about a second axis of rotation $A_2$. The connector is a pin-type connector and includes the pin 11683 which is supported by (and placed within) the pin openings 11682. As shown in FIG. 59, the second axis of rotation $A_2$ is nonparallel to the pitch axis $A_1$. Thus, the instrument 11400 provides for up to three degrees of freedom (i.e., a pitch motion about the first axis of rotation $A_1$, a yaw rotation about the second axis of rotation $A_2$, and a grip motion about the second axis of rotation $A_2$).

The second link 11610 defines two central bores 11635 and a central slot 11636. The central bores 11635 are aligned with the central bore 11535 and contain (or allow passage of) the electrical wires 11401, 11405. The central slot 11636 is aligned with the central slot 11536 and contains (or allows passage of) a ground strip (not shown) that is coupled to the insulator 11495. The second link 11610 also defines a first guide channel 11615, a second guide channel 11620, a third guide channel 11625, and a fourth guide channel 11635. The first guide channel 11615 is aligned with the first guide channel 11515 (of the first link 11510), and the second guide channel 11620 is aligned with the second guide channel 11520 (of the first link 11510). In this manner, a portion (e.g., the first proximal portion 11421) of the first band 11420 is routed from the shaft 11410 and through the first guide channel 11515 and the first guide channel 11615 to be coupled to the first tool member 11462. A portion (e.g., a second portion 11431) of the first band 11420 is routed from the first tool member 11462 and back through the second guide channel 11520 and the second guide channel 11620 to be returned to the backend mechanism 11700 (via the shaft). The third guide channel 11625 is aligned with the third guide channel 11525 (of the first link 11510), and the fourth guide channel 11630 is aligned with the fourth guide channel 11530 (of the first link 11510). In this manner, a portion (e.g., the first proximal portion 11441) of the second band 11440 is routed from the shaft 11410 and through the third guide channel 11525 and the third guide channel 11625 to be coupled to the second tool member 11482. A portion (e.g., a second portion 11451) of the second band 11440 is routed from the second tool member 11482 and back through the fourth guide channel 11530 and the fourth guide channel 11630 to be returned to the backend mechanism (via the shaft).

Similar to the guide channels described above for the second link 8610 (and for the instrument 3400), the guide channels 11615, 11620, 11625, 11630 are curved along a longitudinal center line of the second link 11610 (or wrist assembly 11500). Specifically, the inner guide surfaces and the outer guide surfaces that define the guide channels 11615, 11620, 11625, 11630 can have any suitable radius of curvature, and can have different curve shapes, similar to the shapes described above with respect to the instrument 3400. In this manner, when the second link 11610 rotates relative to the first link 11510 about the pitch axis $A_1$ (see the arrow SS in FIG. 46) the respective portions of the first band 11420 and the second band 11440 can contact the curved portions of their respective inner guide surfaces and the outer guide surfaces to maintain the desired bend geometry, band tension, and the like during actuation of the instrument 11400. Moreover, as described above, the guide channels 11615, 11620, 11625, 11630 are offset from the first axis of rotation $A_1$. In this manner, application of a force on the second link 11610 via the first band 11420 or the second band 11440 produces a torque about the first axis of rotation $A_1$.

The end effector 11460 includes a first tool member 11462 and a second tool member 11482. The first tool member 11462 includes a contact member 11464 and a pulley member 11467. Unlike the first tool member 10462, the contact member 11464 and the pulley member 11467 are separate components that are coupled together to form the first tool member 11462. The contact member 11464 is configured to engage or manipulate or cut a target tissue during a surgical procedure. The contact member 11464 includes a coupling portion 11465 that is coupled to the pulley member 11467 and is disposed about the pin 11683. The contact member 11464 also includes a connector to which the wire 11401 is coupled. In this manner, electrical current from the backend mechanism 11700 can be conveyed to the contact member 11462 to perform cauterization or other procedures. The pulley member 11467 includes a guide surface 11470, a central opening 11468, and a connection slot 11469. The guide surface 11470 is within a channel and is the surface about which the distal end portion 11422 of the first band 11420 is wrapped. The distal end portion 11422 of the first band 11420 includes a connection tab 11424 that is coupled within the connection slot 11469 of the pulley member 11487. The pulley member 11467 is rotatably coupled to the second link 11610 via the pin 11683, which is disposed within the central opening 11468. In this manner, the first tool member 11462 (both the contact member 11464 and the pulley member 11467) rotate about the pin 11683 and relative to the second link 11610 about the second axis of rotation $A_2$, as shown by the arrow XX in FIG. 59. Moreover, the guide surface 11470 is offset from the yaw axis $A_2$ (i.e., by the radius of the guide surface 11470). In this manner, application of a force by the first band 11420 on the pulley member 11467 produces a torque on the first tool member 11462 about the yaw axis $A_2$, which results in rotation of the first tool member 11462 or the application of a gripping force.

The second tool member 11482 includes a contact member 11484 and a pulley member 11487. Like the first tool member 11462, the contact member 11484 and the pulley member 11487 are separate components that are coupled together to form the second tool member 11482. The contact member 11484 is configured to engage or manipulate or cut a target tissue during a surgical procedure. The contact member 11484 includes a coupling portion 11485 that is coupled to the pulley member 11487 and is disposed about the pin 11683. The contact member 11484 also includes a connector 11486 to which the wire 11405 is coupled. In this manner, electrical current from the backend mechanism 11700 can be conveyed to the contact member 11482 to perform cauterization or other procedures. The pulley member 11487 includes a guide surface 11490, a central opening 11488, and a connection slot (not shown, but similar to the connection slot 11469). The guide surface 11490 is within a channel and is the surface about which the distal end portion 11442 of the second band 11440 is wrapped. The distal end portion 11442 of the second band 11440 includes a connection tab 11444 that is coupled within the connection slot of the pulley member 11487. The pulley member 11487 is rotatably coupled to the second link 11610 via the pin 11683, which is disposed within the central opening 11488. In this manner, the second tool member 11482 (both the contact member 11484 and the pulley member 11487) rotates about the pin 11683 and relative to the second link 11610 about the second axis of rotation Az, as shown by the arrow XX in FIG. 59.

The first band 11420 has a first proximal end portion 11421, a second proximal end portion 11431, a distal end portion 11422, a first central portion 11423, and a second central portion 11433. As shown, the distal end portion 11422 is wrapped about and coupled to the pulley portion 11467 of the first tool member 11462 via the tab 11424. The first proximal end portion 11421 and the second proximal end portion 11431 each extend through the first link 11510 (i.e., the first guide channel 11515 and the second guide channel 11520, respectively) and into the shaft 11410. Additionally, the first proximal end portion 11421 and the second proximal end portion 11431 each extend through the shaft 11410 and are coupled to the backend mechanism 11700. The backend mechanism 11700 can move each of the proximal end portions to produce pitch, yaw, and gripping movements of the wrist assembly 11500. The first central portion 11423 is between the first proximal end portion 11421 and the distal end portion 11422, and the second central portion 11433 is between the second proximal end portion 11431 and the distal end portion 11422. As shown, the first band 11420 is twisted along its longitudinal center line in two places: the first region of twist is along the first central portion 11423 and the second region of twist is along the second central portion 11433. In this manner, the orientation of the contact surfaces of the first band 11420 at the first proximal end portion 11421 and the second proximal end portion 11431 (i.e., the band surfaces that contact or are wrapped about the inner and outer guide surfaces) are different than an orientation of the contact surface of the first band 11420 at the distal end portion 11422 (i.e., the band surface that is wrapped about pulley portion 11467).

The second band 11440 has a first proximal end portion 11441, a second proximal end portion 11451, a distal end portion 11442, a first central portion 11443, and a second central portion 11453. As shown, the distal end portion 11442 is wrapped about and coupled to the pulley portion 11487 of the second tool member 11482 by the tab 11444. The first proximal end portion 11441 and the second proximal end portion 11451 each extend through the first link 11510 (i.e., the first guide channel 11525 and the second guide channel 11530, respectively) and into the shaft 11410. Additionally, the first proximal end portion 11441 and the second proximal end portion 11451 each extend through the shaft 11410 and are coupled to the backend mechanism 11700. The backend mechanism 11700 can move each of the proximal end portions to produce pitch, yaw, and gripping movements of the wrist assembly 11500. The first central portion 11443 is between the first proximal end portion 11421 and the distal end portion 11442, and the second central portion 11453 is between the second proximal end portion 11451 and the distal end portion 11442. As shown, the second band 11440 is twisted along its longitudinal center line in two places: the first region of twist is along the first central portion 11443 and the second region of twist is along the second central portion. In this manner, the orientation of the contact surfaces of the second band 11440 at the first proximal end portion 11441 and the second proximal end portion 11451 (i.e., the band surfaces that contact or are wrapped about the inner and outer guide surfaces) are different than an orientation of the contact surface of the second band 11440 at the distal end portion 11442 (i.e., the band surface that is wrapped about the pulley portion 11487).

Figure 64:
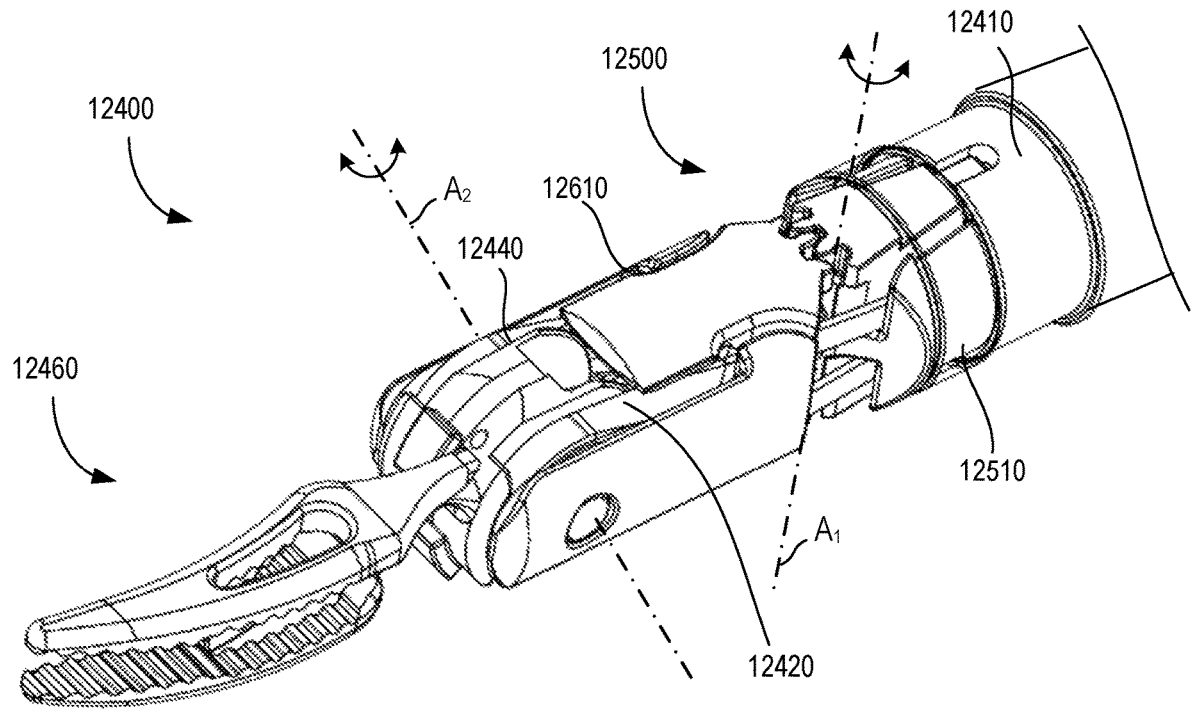
FIG. 64 is a perspective view of a distal end portion of an instrument of a surgery system, according to an embodiment.
Figure 65:
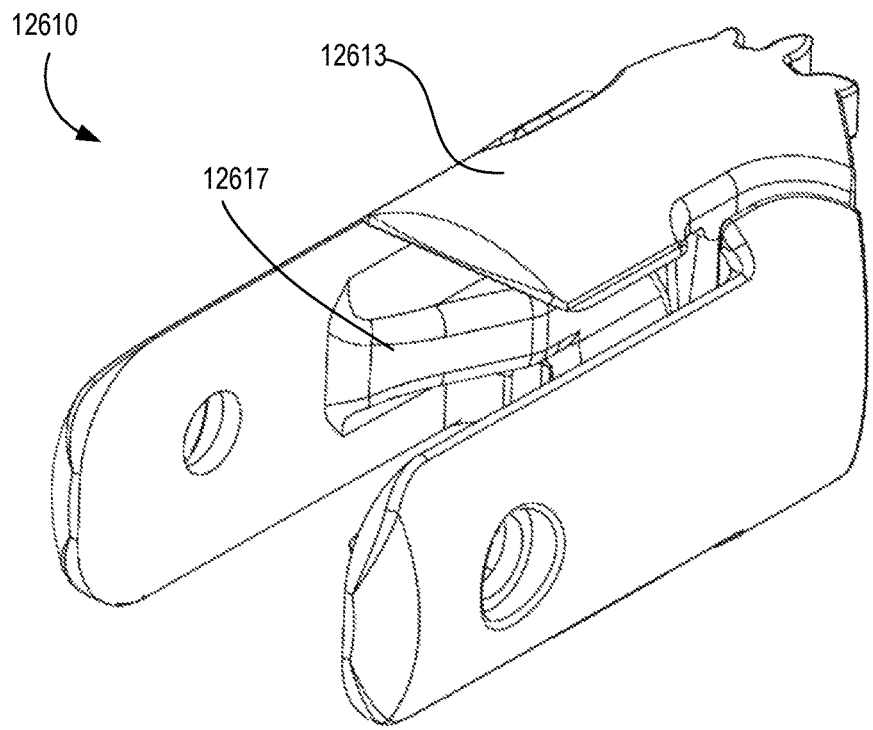
FIG. 65 is a perspective view of a second link of the wrist assembly of the instrument shown in FIG. 64.

Any of the instruments described herein can include any suitable first link design or second link design to ensure that the bands therein are maintained at the desired bend geometry, band tension, and the like during actuation of the instrument. Thus, any of the first links described herein can include any number of guide channels having any suitable geometry (e.g., radii of curvature, offset distance from one or more axes, or the like). Similarly, any of the second links described herein can include any number of guide channels having any suitable geometry (e.g., radii of curvature, offset distance from one or more axes, or the like). FIGS. 64 and 65 are various views of a portion of an instrument 12400, according to an embodiment. In some embodiments, the instrument 12400 or any of the components therein are optionally parts of a surgical system that performs surgical procedures, and which can include a manipulator unit, a series of kinematic linkages, a series of cannulas, or the like. The instrument 12400 (and any of the instruments described herein) can be used in any suitable surgical system, such as the MIRS system 1000 shown and described above. The instrument 12400 includes a backend mechanism (not shown), a shaft 12410, a first link 12510, a second link 12610, a wrist assembly 12500, and an end effector 12460. Referring to FIG. 63, the instrument 12400 also includes a first band 12420 and a second band 12440 that couple the backend mechanism to the wrist assembly 12500. The instrument 12400 is configured such that movement of the bands produces rotation of the wrist assembly 12500 (i.e., pitch rotation) about a first axis of rotation $A_1$ (see FIG. 64, which functions as the pitch axis, the term pitch is arbitrary), yaw rotation of the end effector 12460 about a second axis of rotation $A_2$ (see FIG. 64, which functions as the yaw axis), grip rotation of the tool members of the end effector 12460 about the yaw axis, or any combination of these movements. Changing the pitch, yaw, or grip of the instrument 12400 can be performed by manipulating the bands in similar manner as that described above for the instrument 6400. FIG. 65 shows a perspective view of the second link 12610. As shown, the second link 12610 includes additional guide surfaces 12617 and covering surfaces 12613 that are not present in some of the second links described herein.

Figure 66:
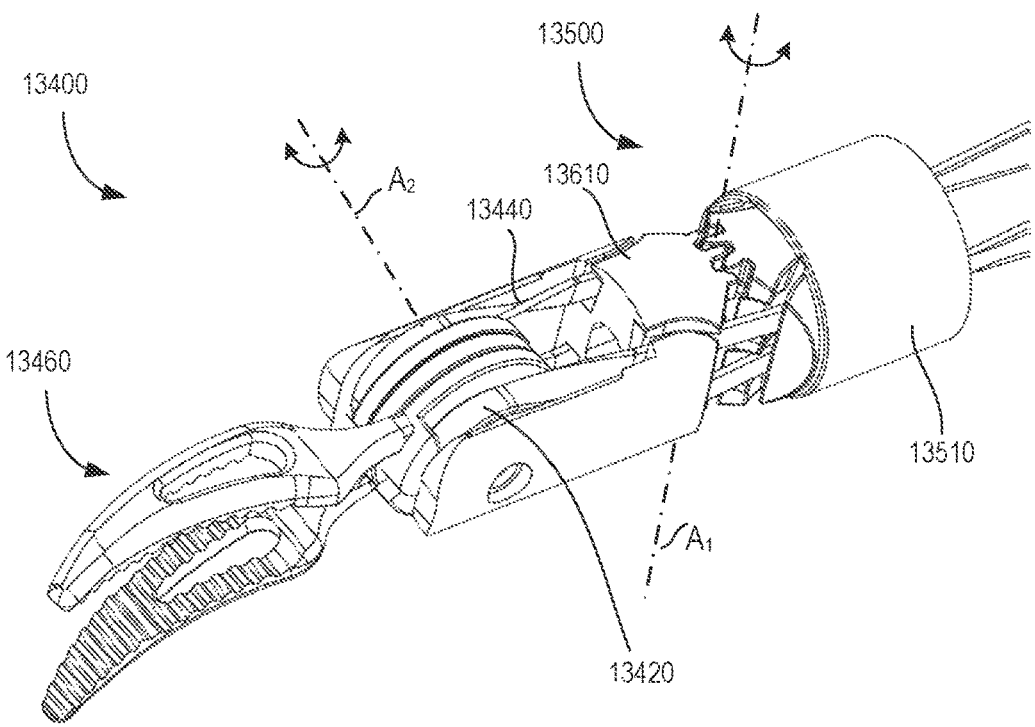
FIG. 66 is a perspective view of a distal end portion of an instrument of a surgery system, according to an embodiment.
Figure 67:
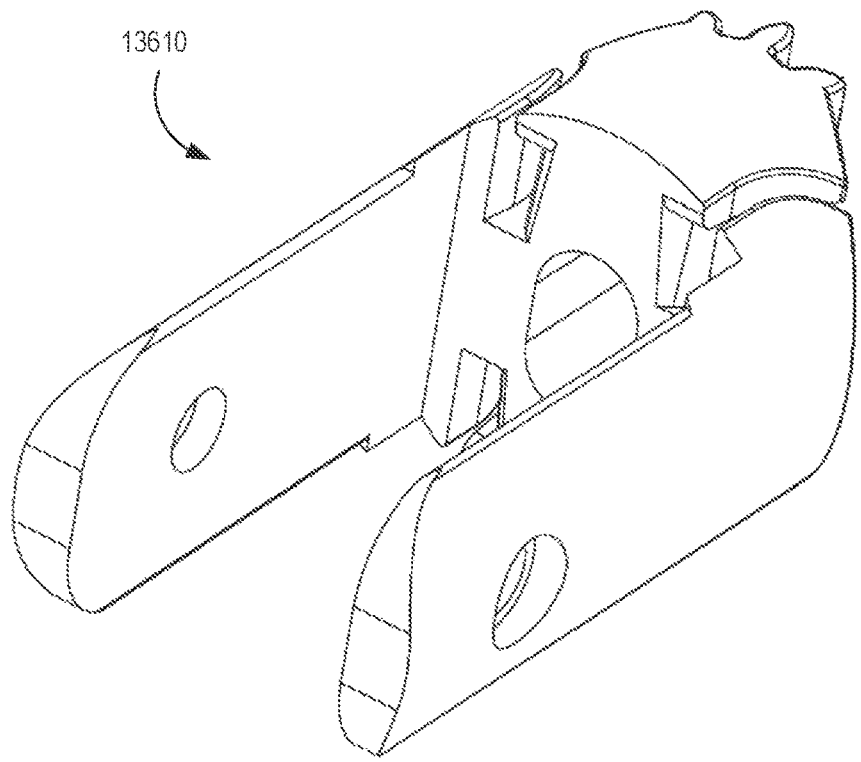
FIG. 67 is a perspective view of a second link of the wrist assembly of the instrument shown in FIG. 66.

FIGS. 66 and 67 are various views of a portion of an instrument 13400, according to an embodiment. In some embodiments, the instrument 13400 or any of the components therein are optionally parts of a surgical system that performs surgical procedures, and which can include a manipulator unit, a series of kinematic linkages, a series of cannulas, or the like. The instrument 13400 (and any of the instruments described herein) can be used in any suitable surgical system, such as the MIRS system 1000 shown and described above. The instrument 13400 includes a backend mechanism (not shown), a shaft (not shown), a first link 13510, a second link 13610, a wrist assembly 13500, and an end effector 13460. Referring to FIG. 63, the instrument 13400 also includes a first band 13420 and a second band 13440 that couple the backend mechanism to the wrist assembly 13500. The instrument 13400 is configured such that movement of the bands produces rotation of the wrist assembly 13500 (i.e., pitch rotation) about a first axis of rotation $A_1$ (see FIG. 66 which functions as the pitch axis), yaw rotation of the end effector 13460 about a second axis of rotation $A_2$ (see FIG. 66, which functions as the yaw axis), grip rotation of the tool members of the end effector 13460 about the yaw axis, or any combination of these movements. Changing the pitch, yaw, or grip of the instrument 13400 can be performed by manipulating the bands in similar manner as that described above for the instrument 6400. FIG. 67 shows a perspective view of the second link 13610.

While various embodiments have been described above, it should be understood that they have been presented by way of example only, and not limitation. Where methods and/or diagrammatic drawings described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a surgical system that performs surgical procedures, and which can include a manipulator unit, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, any of the tool members can be constructed from any material, such as medical grade stainless steel, nickel alloys, titanium alloys or the like. Further, any of the links, tool members, bands, or components described herein can be constructed from multiple pieces that are later joined together. For example, in some embodiments, a link can be constructed by joining together separately constructed components. In other embodiments, however, any of the links, tool members, bands, or components described herein can be monolithically constructed.

Any of the bands described herein can have any suitable shape. For example, although FIG. 10 shows the band 2420 as having a rectangular cross-sectional shape (taken within a cross-sectional plane normal to the longitudinal center line of the band 2420), in other embodiments, any of the bands described herein can have any suitable cross-sectional shape. For example, in some embodiments, any of the bands described can have a trapezoidal shape (see e.g., FIG. 24). In other embodiments, any of the bands described herein can include slightly curved surfaces. For example, although the inner contact surface 2425 and the outer contact surface 2426 are shown as being linear (within a cross-sectional plane normal to the longitudinal center line of the band 2420), in other embodiments, any of the inner contact surfaces or outer contact surfaces can be curved or "crowned." Moreover, any of the bands described herein) can be constructed from any suitable materials. For example, in some embodiments, any of the bands described herein can be constructed from a series of laminates that are bonded together (e.g., via an adhesive). In other embodiments, the laminates can be joined by any other suitable method. The laminates can be constructed from any suitable material, including tungsten, steel, or any suitable polymer.

Although the instruments are generally shown as having a second axis of rotation $A_2$ that is normal to the first axis of rotation $A_1$, in other embodiments, any of the instruments described herein can include a second axis of rotation $A_2$ that is offset from the first axis of rotation $A_1$ by any suitable angle.

Although the instruments are generally described as being disposable, in other embodiments, any of the instruments described herein can be reusable.

Although the bands are described herein as being coupled to the tool members by a tab placed within a corresponding slot, in other embodiments, any of the bands described herein can be coupled to any of the tool members by any suitable mechanism, such as welding, adhesive, or a mechanical fastener.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

For example, in some embodiments an instrument can include a band that is twisted as described above with reference to the instrument 4400 and that also has one or more links (e.g., a first link or a second link) that include and inner guide surface or an outer guide surface as described above with reference to the instrument 3400. Thus, in some embodiments, the instrument can include a wrist assembly that defines a guide surface that can be curved along a longitudinal center line and that can have a linear surface along a cross-section normal to the longitudinal center line.

What is claimed is:

1. A medical device, comprising:
a shaft, a first link, a second link, a tool member, and a band;
the first link being coupled to the shaft;
the second link comprising a proximal end portion and distal end portion, the proximal end portion being coupled to the first link, the second link being rotatable relative to the first link about a first axis, and a guide channel being defined with the second link;
the tool member comprising a contact portion and a pulley portion, the contact portion being configured to contact a target tissue, the pulley portion being rotatably coupled to the distal end portion of the second link, the tool member being rotatable relative to the second link about a second axis, and the second axis being non-parallel to the first axis;

the band comprising a first planar band portion and a second planar band portion, a longitudinal center line of the band being defined between the first planar band portion and the second planar band portion, the first planar band portion being within the guide channel, the second planar band portion being coupled to the tool member, and the band being twisted along the longitudinal center line of the band between the first planar band portion and the second planar band portion; and the tool member being rotatable relative to the second link about the second axis as the band is moved along the longitudinal center line of the band.

2. The medical device of claim 1, wherein:
the first axis and the second axis define a rotation axis offset angle;
the band is twisted through a twist angle between the first planar band portion and the second planar band portion; and
the twist angle is the same as the rotation axis offset angle.

3. The medical device of claim 2, wherein the twist angle is about 90 degrees.

4. The medical device of claim 1, wherein:
the second link comprises a guide surface;
the guide surface defines a portion of the guide channel;
the pulley portion of the tool member comprises a coupling surface; and
the band comprises a contact surface, the contact surface of the first planar band portion being in sliding contact with the guide surface, and the contact surface of the second planar band portion being coupled to the coupling surface of the tool member.

5. The medical device of claim 4, wherein:
a portion of the guide surface taken within a cross-sectional plane normal to the longitudinal center line of the band is a linear portion; and
the contact surface of the first planar band portion contacting the linear portion of the guide surface as the second link rotates relative to the first link about the first axis.

6. The medical device of claim 1, wherein:
the band is constructed from a plurality of laminates; and
the band has a rectangular cross-sectional shape taken along the longitudinal center line of the band.

7. The medical device of claim 1, wherein:
a center line of the second link is defined between the proximal end portion and the distal end portion of the second link; and
the guide channel is offset from the center line of the second link such that the second link rotates relative to the first link about the first axis as the band is moved along the longitudinal center line of the band.

8. The medical device of claim 1, wherein:
the guide channel is a first guide channel, and the band is a first band;
a second guide channel is defined within the second link;
the medical device further comprises a second band;
the second band comprises a third band portion, a fourth band portion, and a longitudinal center line defined between the third band portion and the fourth band portion;
the third band portion is within the second guide channel;
the fourth band portion is coupled to the tool member;
the second band is twisted along the longitudinal center line of the second band;

the second link rotates relative to the first link about the first axis as the first band and the second band are each moved in a proximal direction; and
the tool member rotates relative to the second link about the second axis as the first band is moved in the proximal direction and the second band is moved in a distal direction.

9. The medical device of claim 8, wherein the first band and the second band are monolithically constructed.

10. The medical device of claim 9, wherein the second planar band portion and the fourth band portion are wrapped about the pulley portion of the tool member.

11. The medical device of claim 1, wherein:
the guide channel is a first guide channel, the tool member is a first tool member, and the band is a first band;
a second guide channel is defined within the second link;
the medical device further comprises a second tool member and a second band;
the second tool member comprises a pulley portion rotatably coupled to the distal end portion of the second link;
the second tool member is rotatable relative to the second link about the second axis;
the second band comprises a third band portion, a fourth band portion, and a longitudinal center line of the second band defined between the third band portion and the fourth band portion;
the third band portion is within the second guide channel;
the fourth band portion is coupled to the second tool member;
the second band is twisted along the longitudinal center line of the second band and
the second tool member rotates relative to the second link about the second axis as the second band is moved along the longitudinal center line of the second band.

12. The medical device of claim 1, wherein:
the guide channel is a first guide channel;
a second guide channel is defined within the second link;
the band comprises a third band portion, the second planar band portion being between the first planar band portion and the third band portion, the third band portion being disposed within the second guide channel, and the second planar band portion being at least partially wrapped about the pulley portion; and
the tool member rotates relative to the second link about the second axis as the band is moved along the longitudinal center line of the band.

13. A medical device, comprising:
a shaft, a first link coupled to the shaft, a second link, a band, and a tool member;
the second link comprising a proximal end portion and distal end portion, the proximal end portion being coupled to the first link, the second link being rotatable relative to the first link about a first axis, and the second link comprising a guide surface;
the tool member having a contact portion and a pulley portion, the contact portion being configured to contact a target tissue, the pulley portion being rotatably coupled to the distal end portion of the second link, the tool member being rotatable relative to the second link about a second axis, and the second axis being non-parallel to the first axis;
the band comprising a planar contact surface and a longitudinal center line, the planar contact surface comprising a first portion and a second portion, the first portion of the planar contact surface being in sliding contact with the guide surface at a first band location along the longitudinal center line of the band, the second portion of the planar contact surface being coupled to the pulley portion at a second band location along the longitudinal center line of the band, and the first portion of the planar contact surface being non-parallel to the second portion of the planar contact surface; and the tool member being rotatable relative to the second link about the second axis as the band is moved along the longitudinal center line of the band.

14. The medical device of claim 13, wherein a twist angle between the first portion of the planar contact surface and the second portion of the planar contact surface is about 90 degrees.

15. The medical device of claim 13, wherein:
the first axis and the second axis define a rotation axis offset angle;
the band is twisted through a twist angle between the first portion of the planar contact surface and the second portion of the planar contact surface; and
the twist angle is the same as the rotation axis offset angle.

16. The medical device of claim 13, wherein:
the guide surface of the second link defines at least a portion of a guide channel; and
the first portion of the planar contact surface is disposed within the guide channel.

17. The medical device of claim 13, wherein:
the band is constructed from a plurality of laminates; and
the band has a rectangular cross-sectional shape taken within a plane normal to the longitudinal center line of the band.

18. The medical device of claim 13, wherein the guide surface is offset from a center line of the second link such that the second link rotates relative to the first link about the first axis as the band is moved along the longitudinal center line of the band.

19. The medical device of claim 13, wherein:
the guide surface is a first guide surface, and the band is a first band;
the second link comprises a second guide surface;
the medical device further comprises a second band comprising a second planar contact surface and a longitudinal center line;
the second planar contact surface comprises a first portion and a second portion;

the first portion of the second planar contact surface is non-parallel to the second portion of the second planar contact surface;
the first portion of the second planar contact surface in sliding contact with the second guide surface at a third band location along a longitudinal center line of the second band;
the second portion of the second planar contact surface is coupled to the tool member at a fourth band location along the longitudinal center line of the second band;
the second link rotates relative to the first link about the first axis as the first band and the second band are each moved in a proximal direction; and
the tool member rotates relative to the second link about the second axis as the first band is moved in the proximal direction and the second band is moved in a distal direction.

20. A medical device, comprising:
a shaft, a first link coupled to the shaft, a second link, a band, and tool member for contacting a target tissue;
the second link comprising a proximal end portion and distal end portion, the proximal end portion being coupled to the first link, the second link being rotatable relative to the first link about a first axis, and a first guide channel and a second guide channel each being defined with the second link;
the tool member for contacting the target tissue and being rotatably coupled to the second link to rotate relative to the second link about a second axis, and the second axis being non-parallel to the first axis;
the band comprising a first planar band portion, a second planar band portion, and a third planar band portion, the second planar band portion being between the first planar band portion and the third planar band portion, a longitudinal center line of the band being defined between the first planar band portion and the second planar band portion, the first planar band portion being within the first guide channel, the third planar band portion being within the second guide channel, the second planar band portion being at least partially wrapped about the tool member, and the band being twisted along the longitudinal center line of the band; and
the tool member being rotatable relative to the second link about the second axis as the band is moved along the longitudinal center line of the band.

* * * * *